Figure 3A:

United States Patent [19]
Ullrich et al.

[11] Patent Number: 5,851,999
[45] Date of Patent: Dec. 22, 1998

[54] FLK-1 IS A RECEPTOR FOR VASCULAR ENDOTHELIAL GROWTH FACTOR

[75] Inventors: Axel Ullrich, München; Werner Risau, Grafelfing; Birgit Millauer, München, all of Germany; Aviv Gazit; Alex Levitzki, both of Jerusalem, Israel

[73] Assignees: Max-Planck-Gesellschaft zur Förderung der Wissenschaften ev., Martinsried, Germany; Yissum Research, Development Company of the Hebrew University of Jerusalem, Jerusalem, Israel

[21] Appl. No.: 443,861

[22] Filed: May 22, 1995

Related U.S. Application Data

[60] Division of Ser. No. 193,829, Feb. 9, 1994, which is a continuation-in-part of Ser. No. 38,596, Mar. 26, 1993, abandoned, which is a continuation-in-part of Ser. No. 975,750, Nov. 13, 1992, abandoned.

[51] Int. Cl.$^6$ .............................. A61K 48/00; C12N 5/00; C12N 15/00
[52] U.S. Cl. ...................... 514/44; 424/93.2; 435/320.1
[58] Field of Search .............................. 514/44; 435/69.1, 435/172.3, 320.1, 252–3, 361, 375; 424/93.2; 935/57, 70, 71, 32

[56] References Cited

PUBLICATIONS

Ueno et al (1991) Science 252: 844–848.
Ueno et al (1992) J. Biol. Chem. 267: 1470–1476.

*Primary Examiner*—Bruce R. Campell
*Attorney, Agent, or Firm*—Pennie & Edmonds LLP

[57] ABSTRACT

The present invention relates to the use of ligands for the FLK-1 receptor for the modulation of angiogenesis and vasculogenesis. The invention is based, in part, on the demonstration that Flk-1 tyrosine kinase receptor expression is associated with endothelial cells and the identification of vascular endothelial growth factor (VEGF) as the high affinity ligand of Flk-1. These results indicate a major role for Flk-1 in the signaling system during vasculogenesis and angiogenesis. Engineering of host cells that express Flk-1 and the uses of expressed Flk-1 to evaluate and screen for drugs and analogs of VEGF involved in Flk-1 modulation by either agonist or antagonist activities is described. The invention also relates to the use of FLK-1 ligands, including VEGF agonists and antagonists, in the treatment of disorders, including cancer, by modulating vasculogenesis and angiogenesis.

32 Claims, 25 Drawing Sheets

FIG. 1

```
FLK-1  866  ILIHIGHHLNVVNLLGACTKPGGPLMVIVEFSKFGNLSTYLRGKRNEFVPYKSKGARFRQ
KDR         ------------------------------C--D-------S---------T-------
TKR-C       ------------------------------C--------------------------S

FLK-1  926  GKDYVGELSVDLKRRLDSITSSQSSASSGFVEEKSLSDVEEEEASEELYKDFLTLEHLIC
KDR         ------AIP-----------------------------------P-D-------------
TKR-C       ------------------------------------------------------------

FLK-1  986  YSFQVAKGMEFLASRKCIHRDLAARNILLSEKNVVKICDFGLARDIYKDPDYVRKGDARL
KDR         ------------------------------------------------------------
TKR-C       ------------------------------------------------------------
```

FIG. 2A
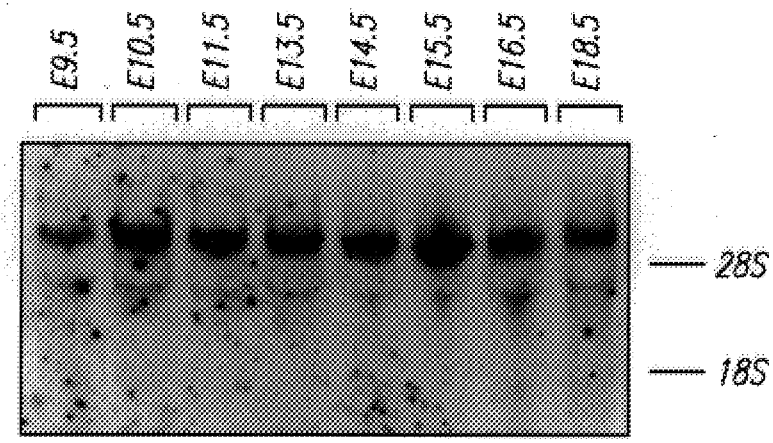
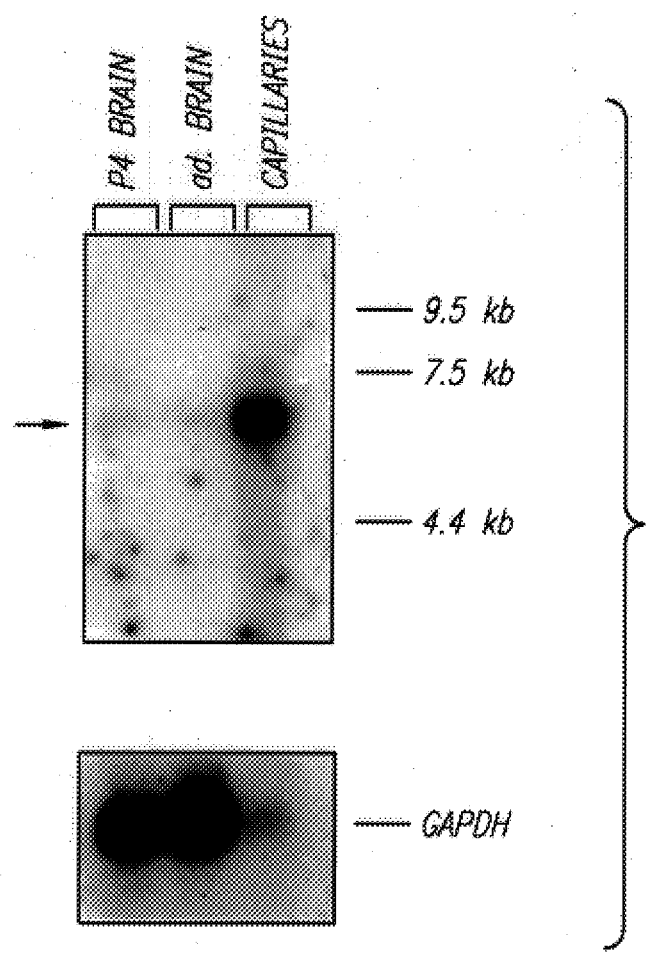
FIG. 2B

FIG. 4A
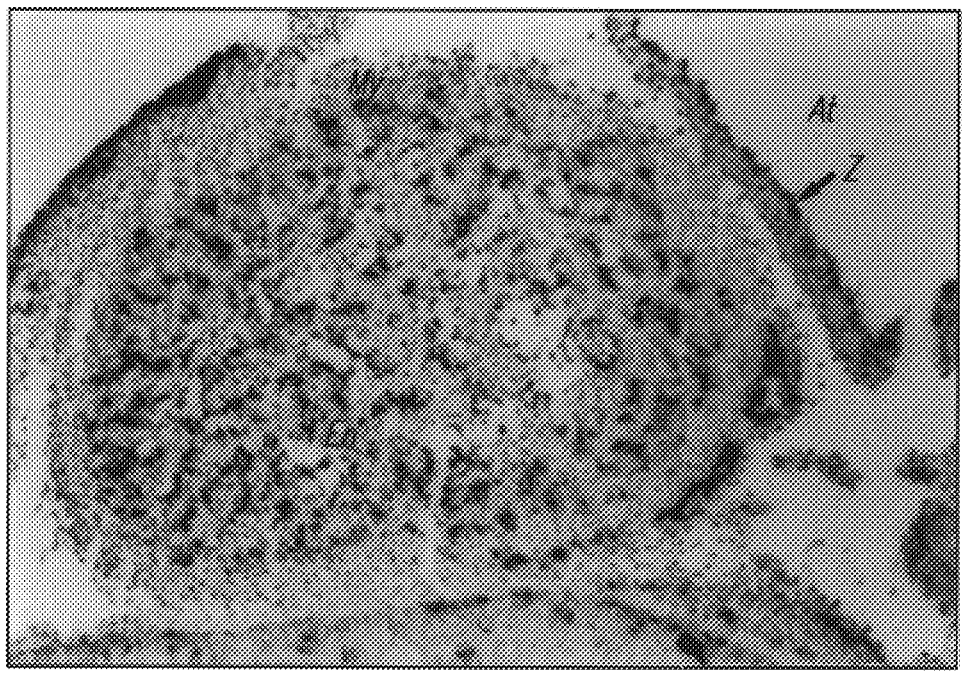
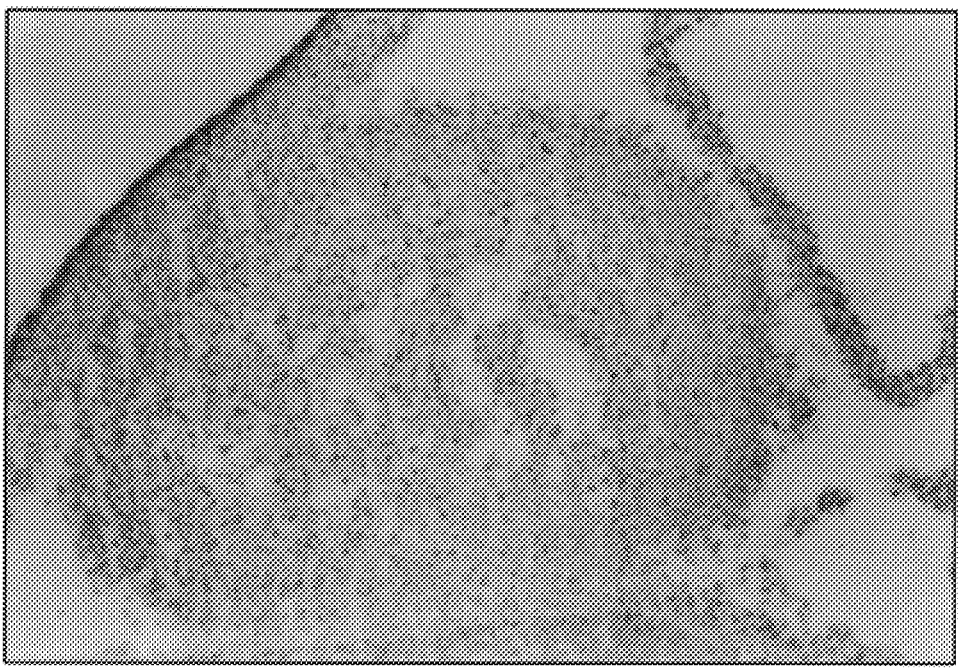
FIG. 4B

FIG. 5A
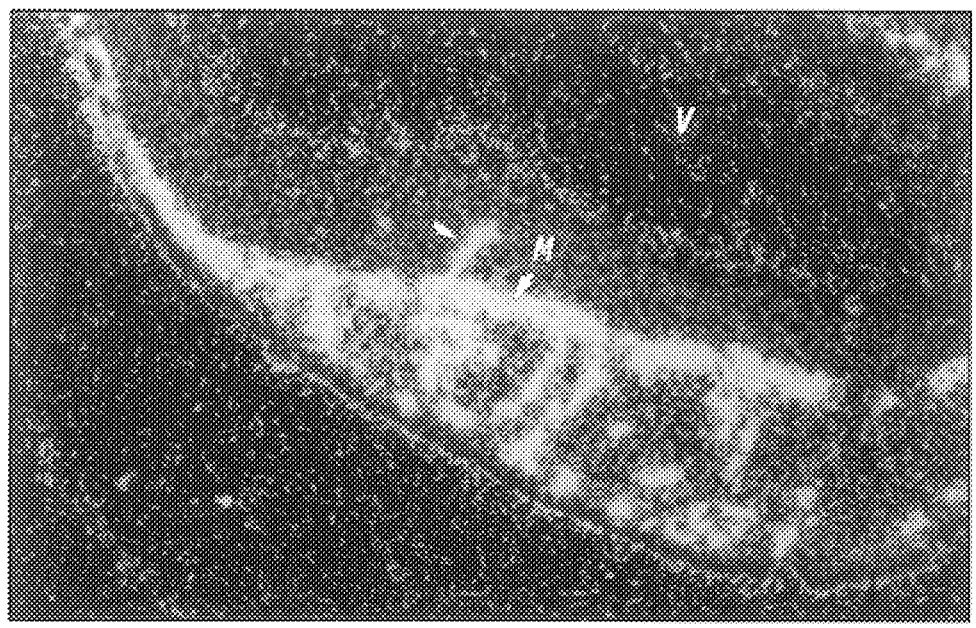
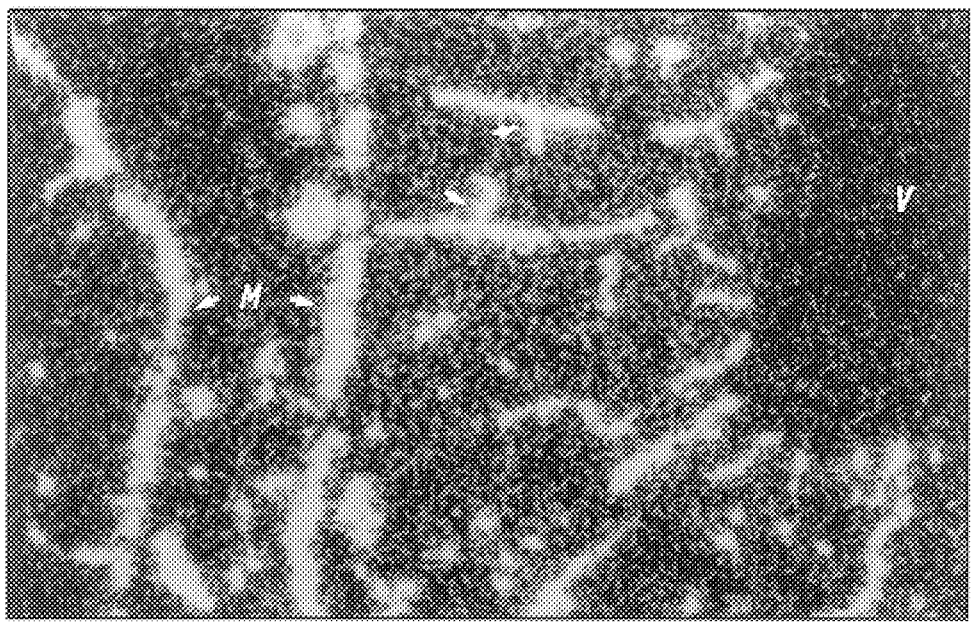
FIG. 5B

FIG. 6A
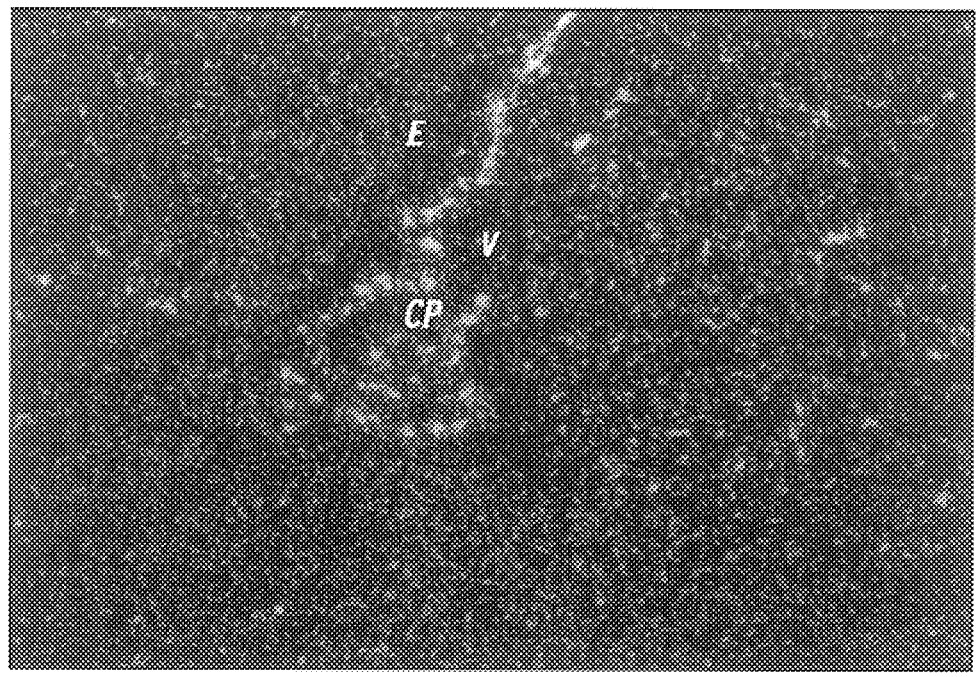
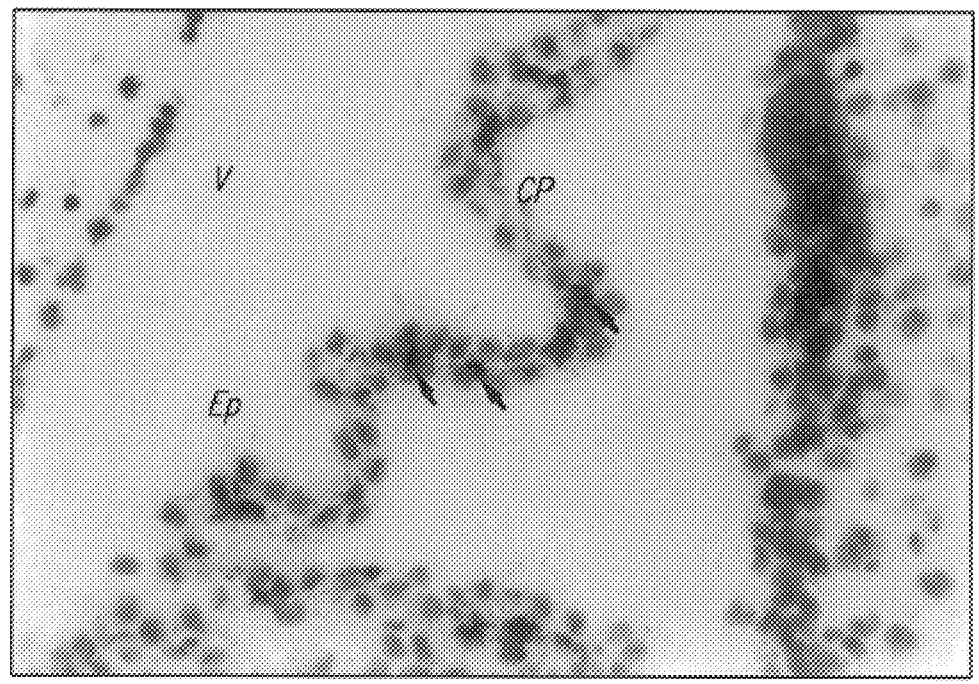
FIG. 6B

FIG. 7A
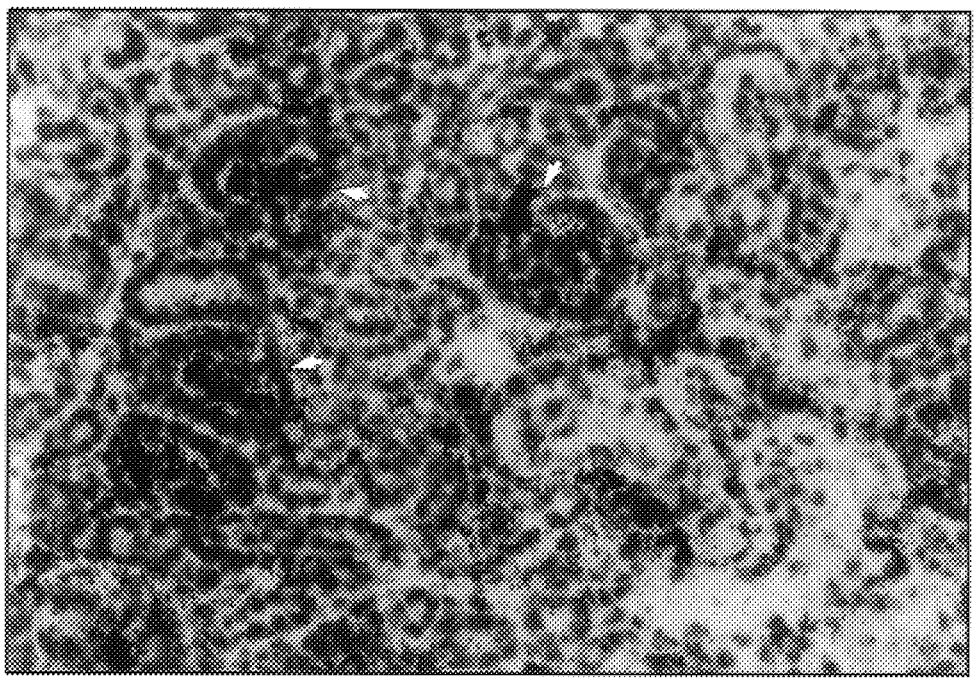
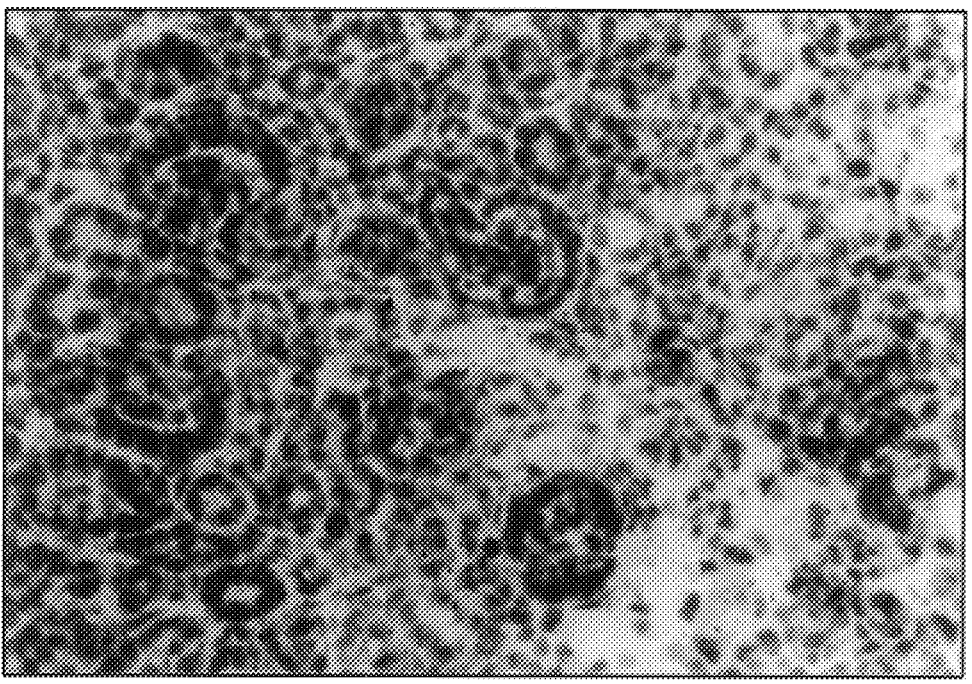
FIG. 7B

FIG. 7C
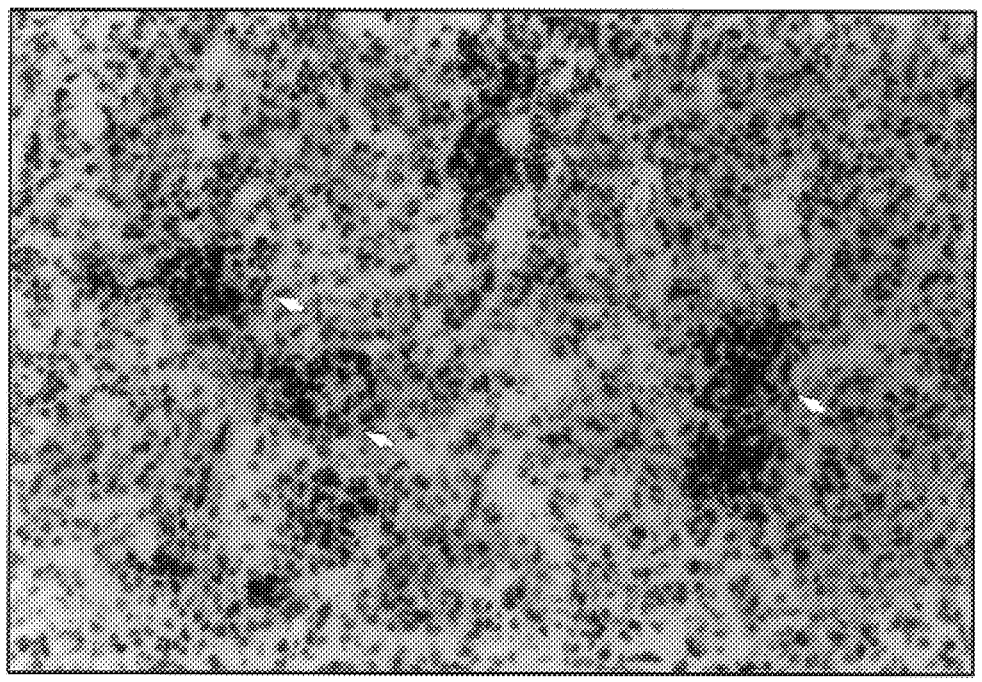
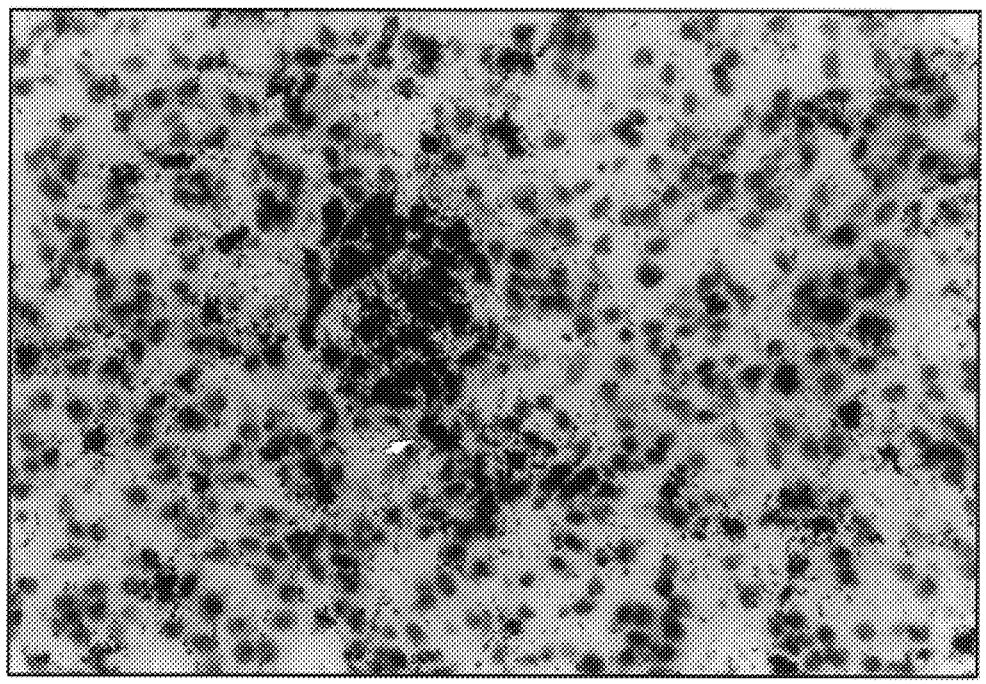
FIG. 7D

FIG. 11-1

```
CTGTGTCCCGCAGCCGGGATAACCTGGCTGACCCGATTCCGCGGACACCGCTGACAGCCGCGGCTGGAGCCAGGG    75
CGCCGGTGCCCCGCGCTCTCCCCGGTCTTGCGCTGCGGGGGCCATACCGCCTCTGTGACTTCTTTGCGGGCCAGG   150
GACGGAGAAGGAGTCTGTGCCTGAGAAACTGGGCTCTGTGCCCAGGCGCGAGGTGCAGGATGGAGAGCAAGGCGC   225
                                                            M  E  S  K  A  L

TGCTAGCTGTCGCTCTGTGGTTCTGCGTGGAGACCCGAGCCGCCTCTGTGGGTTTGACTGGCGATTTTCTCCATC   300
 L  A  V  A  L  W  F  C  V  E  T  R  A  A  S  V  G  L  T  G  D  F  L  H  P

CCCCCAAGCTCAGCACACAGAAAGACATACTGACAATTTTGGCAAATACAACCCTTCAGATTACTTGCAGGGGAC   375
 P  K  L  S  T  Q  K  D  I  L  T  I  L  A  N  T  T  L  Q  I  T  C  R  G  Q

AGCGGGACCTGGACTGGCTTTGGCCCAATGCTCAGCGTGATTCTGAGGAAAGGGTATTGGTGACTGAATGCGGCG   450
 R  D  L  D  W  L  W  P  N  A  Q  R  D  S  E  E  R  V  L  V  T  E  C  G  G

GTGGTGACAGTATCTTCTGCAAAACACTCACCATTCCCAGGGTGGTTGGAAATGATACTGGAGCCTACAAGTGCT   525
 G  D  S  I  F  C  K  T  L  T  I  P  R  V  V  G  N  D  T  G  A  Y  K  C  S

CGTACCGGGACGTCGACATAGCCTCCACTGTTTATGTCTATGTTCGAGATTACAGATCACCATTCATCGCCTCTG   600
 Y  R  D  V  D  I  A  S  T  V  Y  V  Y  V  R  D  Y  R  S  P  F  I  A  S  V

TCAGTGACCAGCATGGCATCGTGTACATCACCGAGAACAAGAACAAAACTGTGGTGATCCCCTGCCGAGGGTCGA   675
 S  D  Q  H  G  I  V  Y  I  T  E  N  K  N  K  T  V  V  I  P  C  R  G  S  I

TTTCAAACCTCAATGTGTCTCTTTGCGCTAGGTATCCAGAAAAGAGATTTGTTCCGGATGGAAACAGAATTTCCT   750
 S  N  L  N  V  S  L  C  A  R  Y  P  E  K  R  F  V  P  D  G  N  R  I  S  W

GGGACAGCGAGATAGGCTTTACTCTCCCCAGTTACATGATCAGCTATGCCGGCATGGTCTTCTGTGAGGCAAAGA   825
 D  S  E  I  G  F  T  L  P  S  Y  M  I  S  Y  A  G  M  V  F  C  E  A  K  I

TCAATGATGAAACCTATCAGTCTATCATGTACATAGTTGTGGTTGTAGGATATAGGATTTATGATGTGATTCTGA   900
 N  D  E  T  Y  Q  S  I  M  Y  I  V  V  V  G  Y  R  I  Y  D  V  I  L  S

GCCCCCCGCATGAAATTGAGCTATCTGCCGGAGAAAAACTTGTCTTAAATTGTACAGCGAGAACAGAGCTCAATG   975
 P  P  H  E  I  E  L  S  A  G  E  K  L  V  L  N  C  T  A  R  T  E  L  N  V

TGGGGCTTGATTTCACCTGGCACTCTCCACCTTCAAAGTCTCATCATAAGAAGATTGTAAACCGGGATGTGAAAC  1050
 G  L  D  F  T  W  H  S  P  P  S  K  S  H  H  K  K  I  V  N  R  D  V  K  P

CCTTTCCTGGGACTGTGGCGAAGATGTTTTTGAGCACCTTGACAATAGAAAGTGTGACCAAGAGTGACCAAGGGG  1125
 F  P  G  T  V  A  K  M  F  L  S  T  L  T  I  E  S  V  T  K  S  D  Q  G  E

AATACACCTGTGTAGCGTCCAGTGGACGGATGATCAAGAGAAATAGAACATTTGTCCGAGTTCACACAAAGCCTT  1200
 Y  T  C  V  A  S  S  G  R  M  I  K  R  N  R  T  F  V  R  V  H  T  K  P  F

TTATTGCTTTCGGTAGTGGGATGAAATCTTTGGTGGAAGCCACAGTGGGCAGTCAAGTCCGAATCCCTGTGAAGT  1275
 I  A  F  G  S  G  M  K  S  L  V  E  A  T  V  G  S  Q  V  R  I  P  V  K  Y

ATCTCAGTTACCCAGCTCCTGATATCAAATGGTACAGAAATGGAAGGCCCATTGAGTCCAACTACACAATGATTG  1350
 L  S  Y  P  A  P  D  I  K  W  Y  R  N  G  R  P  I  E  S  N  Y  T  M  I  V
```

FIG. 11-2

```
TTGGCGATGAACTCACCATCATGGAAGTGACTGAAAGAGATGCAGGAAACTACACGGTCATCCTCACCAACCCCA 1425
 G  D  E  L  T  I  M  E  V  T  E  R  D  A  G  N  Y  T  V  I  L  T  N  P  I

TTTCAATGGAGAAACAGAGCCACATGGTCTCTCTGGTTGTGAATGTCCCACCCCAGATCGGTGAGAAAGCCTTGA 1500
 S  M  E  K  Q  S  H  M  V  S  L  V  V  N  V  P  P  Q  I  G  E  K  A  L  I

TCTCGCCTATGGATTCCTACCAGTATGGGACCATGCAGACATTGACATGCACAGTCTACGCCAACCCTCCCCTGC 1575
 S  P  M  D  S  Y  Q  Y  G  T  M  Q  T  L  T  C  T  V  Y  A  N  P  P  L  H

ACCACATCCAGTGGTACTGGCAGCTAGAAGAAGCCTGCTCCTACAGACCCGGCCAAACAAGCCCGTATGCTTGTA 1650
 H  I  Q  W  Y  W  Q  L  E  E  A  C  S  Y  R  P  G  Q  T  S  P  Y  A  C  K

AAGAATGGAGACACGTGGAGGATTTCCAGGGGGGAAACAAGATCGAAGTCACCAAAAACCAATATGCCCTGATTG 1725
 E  W  R  H  V  E  D  F  Q  G  G  N  K  I  E  V  T  K  N  Q  Y  A  L  I  E

AAGGAAAAAACAAAACTGTAAGTACGCTGGTCATCCAAGCTGCCAACGTGTCAGCGTTGTACAAATGTGAAGCCA 1800
 G  K  N  K  T  V  S  T  L  V  I  Q  A  A  N  V  S  A  L  Y  K  C  E  A  I

TCAACAAAGCGGGACGAGGAGAGAGGGTCATCTCCTTCCATGTGATCAGGGGTCCTGAAATTACTGTGCAACCTG 1875
 N  K  A  G  R  G  E  R  V  I  S  F  H  V  I  R  G  P  E  I  T  V  Q  P  A

CTGCCCAGCCAACTGAGCAGGAGAGTGTGTCCCTGTTGTGCACTGCAGACAGAAATACGTTTGAGAACCTCACGT 1950
 A  Q  P  T  E  Q  E  S  V  S  L  L  C  T  A  D  R  N  T  F  E  N  L  T  W

GGTACAAGCTTGGCTCACAGGCAACATCGGTCCACATGGGCGAATCACTCACACCAGTTTGCAAGAACTTGGATG 2025
 Y  K  L  G  S  Q  A  T  S  V  H  M  G  E  S  L  T  P  V  C  K  N  L  D  A

CTCTTTGGAAACTGAATGGCACCATGTTTTCTAACAGCACAAATGACATCTTGATTGTGGCATTTCAGAATGCCT 2100
 L  W  K  L  N  G  T  M  F  S  N  S  T  N  D  I  L  I  V  A  F  Q  N  A  S

CTCTGCAGGACCAAGGCGACTATGTTTGCTCTGCTCAAGATAAGAAGACCAAGAAAAGACATTGCCTGGTCAAAC 2175
 L  Q  D  Q  G  D  Y  V  C  S  A  Q  D  K  K  T  K  K  R  H  C  L  V  K  Q

AGCTCATCATCCTAGAGCGCATGGCACCCATGATCACCGGAAATCTGGAGAATCAGACAACAACCATTGGCGAGA 2250
 L  I  I  L  E  R  M  A  P  M  I  T  G  N  L  E  N  Q  T  T  T  I  G  E  T

CCATTGAAGTGACTTGCCCAGCATCTGGAAATCCTACCCCACACATTACATGGTTCAAAGACAACGAGACCCTGG 2325
 I  E  V  T  C  P  A  S  G  N  P  T  P  H  I  T  W  F  K  D  N  E  T  L  V

TAGAAGATTCAGGCATTGTACTGAGAGATGGGAACCGGAACCTGACTATCCGCAGGGTGAGGAAGGAGGATGGAG 2400
 E  D  S  G  I  V  L  R  D  G  N  R  N  L  T  I  R  R  V  R  K  E  D  G  G

GCCTCTACACCTGCCAGGCCTGCAATGTCCTTGGCTGTGCAAGAGCGGAGACGCTCTTCATAATAGAAGGTGCCC 2575
 L  Y  T  C  Q  A  C  N  V  L  G  C  A  R  A  E  T  L  F  I  I  E  G  A  Q

AGGAAAAGACCAACTTGGAAGTCATTATCCTCGTCGGCACTGCAGTGATTGCCATGTTCTTCTGGCTCCTTCTTG 2550
 E  K  T  N  L  E  V  I  I  L  V  G  T  A  V  I  A  M  F  F  W  L  L  L  V

TCATTGTCCTACGGACCGTTAAGCGGGCCAATGAAGGGGAACTGAAGACAGGCTACTTGTCTATTGTCATGGATC 2625
 I  V  L  R  T  V  K  R  A  N  E  G  E  L  K  T  G  Y  L  S  I  V  M  D  P
```

FIG. 11-3

```
CAGATGAATTGCCCTTGGATGAGCGCTGTGAACGCTTGCCTTATGATGCCAGCAAGTGGGAATTCCCCAGGGACC 2700
  D   E   L   P   L   D   E   R   C   E   R   L   P   Y   D   A   S   K   W   E   F   P   R   D   R

GGCTGAAACTAGGAAAACCTCTTGGCCGCGGTGCCTTCGGCCAAGTGATTGAGGCAGACGCTTTTGGAATTGACA 2775
  L   K   L   G   K   P   L   G   R   G   A   F   G   Q   V   I   E   A   D   A   F   G   I   D   K

AGACAGCGACTTGCAAAACAGTAGCCGTCAAGATGTTGAAAGAAGGAGCAACACACAGCGAGCATCGAGCCCTCA 2850
  T   A   T   C   K   T   V   A   V   K   M   L   K   E   G   A   T   H   S   E   H   R   A   L   M

TGTCTGAACTCAAGATCCTCATCCACATTGGTCACCATCTCAATGTGGTGAACCTCCTAGGCGCCTGCACCAAGC 2925
  S   E   L   K   I   L   I   H   I   G   H   H   L   N   V   V   N   L   L   G   A   C   T   K   P

CGGGAGGGCCTCTCATGGTGATTCTGCAATTCTCGAAGTTTGGAAACCTATCAACTTACTTACGGGGCAAGAGAA 3000
  G   G   P   L   M   V   I   L   Q   F   S   K   F   G   N   L   S   T   Y   L   R   G   K   R   N

ATGAATTTGTTCCCTATAAGAGCAAAGGGGCACGCTTCCGCCAGGGCAAGGACTACGTTGGGGAGCTCTCCGTGG 3075
  E   F   V   P   Y   K   S   K   G   A   R   F   R   Q   G   K   D   Y   V   G   E   L   S   V   D

ATCTGAAAAGACGCTTGGACAGCATCACCAGCAGCCAGAGCTCTGCCAGCTCAGGCTTTGTTGAGGAGAAATCGC 3150
  L   K   R   R   L   D   S   I   T   S   S   Q   S   S   A   S   S   G   F   V   E   E   K   S   L

TCAGTGATGTAGAGGAAGAAGAAGCTTCTGAAGAACTGTACAAGGACTTCCTGACCTTGGAGCATCTCATCTGTT 3225
  S   D   V   E   E   E   E   A   S   E   E   L   Y   K   D   F   L   T   L   E   H   L   I   C   Y

ACAGCTTCCAAGTGGCTAAGGGCATGGAGTTCTTGGCATCAAGGAAGTGTATCCACAGGGACCTGGCAGCACGAA 3300
  S   F   Q   V   A   K   G   M   E   F   L   A   S   R   K   C   I   H   R   D   L   A   A   R   N

ACATTCTCCTATCGGAGAAGAATGTGGTTAAGATCTGTGACTTCGGCTTGGCCCGGGACATTTATAAAGACCCGG 3375
  I   L   L   S   E   K   N   V   V   K   I   C   D   F   G   L   A   R   D   I   Y   K   D   P   D

ATTATGTCAGAAAAGGAGATGCCCGACTCCCTTTGAAGTGGATGGCCCCGGAAACCATTTTTGACAGAGTATACA 3450
  Y   V   R   K   G   D   A   R   L   P   L   K   W   M   A   P   E   T   I   F   D   R   V   Y   T

CAATTCAGAGCGATGTGTGGTCTTTCGGTGTGTTGCTCTGGGAAATATTTTCCTTAGGTGCCTCCCCATACCCTG 3525
  I   Q   S   D   V   W   S   F   G   V   L   L   W   E   I   F   S   L   G   A   S   P   Y   P   G

GGGTCAAGATTGATGAAGAATTTTGTAGGAGATTGAAAGAAGGAACTAGAATGCGGGCTCCTGACTACACTACCC 3600
  V   K   I   D   E   E   F   C   R   R   L   K   E   G   T   R   M   R   A   P   D   Y   T   T   P

CAGAAATGTACCAGACCATGCTGGACTGCTGGCATGAGGACCCCAACCAGAGACCCTCGTTTTCAGAGTTGGTGG 3675
  E   M   Y   Q   T   M   L   D   C   W   H   E   D   P   N   Q   R   P   S   F   S   E   L   V   E

AGCATTTGGGAAACCTCCTGCAAGCAAATGCGCAGCAGGATGGCAAAGACTATATTGTTCTTCCAATGTCAGAGA 3750
  H   L   G   N   L   L   Q   A   N   A   Q   Q   D   G   K   D   Y   I   V   L   P   M   S   E   T

CACTGAGCATGGAAGAGGATTCTGGACTCTCCCTGCCTACCTCACCTGTTTCCTGTATGGAGGAAGAGGAAGTGT 3825
  L   S   M   E   E   D   S   G   L   S   L   P   T   S   P   V   S   C   M   E   E   E   E   V   C

GCGACCCCAAATTCCATTATGACAACACAGCAGGAATCAGTCATTATCTCCAGAACAGTAAGCGAAAGAGCCGGC 3900
  D   P   K   F   H   Y   D   N   T   A   G   I   S   H   Y   L   Q   N   S   K   R   K   S   R   P
```

FIG. 11-4

```
CAGTGAGTGTAAAAACATTTGAAGATATCCCATTGGAGGAACCAGAAGTAAAAGTGATCCCAGATGACAGCCAGA 3975
 V  S  V  K  T  F  E  D  I  P  L  E  E  P  E  V  K  V  I  P  D  D  S  Q  T

CAGACAGTGGGATGGTCCTTGCATCAGAAGAGCTGAAAACTCTGGAAGACAGGAACAAATTATCTCCATCTTTTG 4050
 D  S  G  M  V  L  A  S  E  E  L  K  T  L  E  D  R  N  K  L  S  P  S  F  G

GTGGAATGATGCCCAGTAAAAGCAGGGAGTCTGTGGCCTCGGAAGGCTCCAACCAGACCAGTGGCTACCAGTCTG 4125
 G  M  M  P  S  K  S  R  E  S  V  A  S  E  G  S  N  Q  T  S  G  Y  Q  S  G

GGTATCACTCAGATGACACAGACACCACCGTGTACTCCAGCGACGAGGCAGGACTTTTAAAGATGGTGGATGCTG 4200
 Y  H  S  D  D  T  D  T  T  V  Y  S  S  D  E  A  G  L  L  K  M  V  D  A  A

CAGTTCACGCTGACTCAGGGACCACACTGAGCTCACCTCCTGTTTAAATGGAAGTGGTCCTGTCCCGGCTCCGCC 4275
 V  H  A  D  S  G  T  T  L  S  S  P  P  V

CCCAACTCCTGGAAATCACGAGAGAGGTGCTGCTTAGATTTTCAAGTGTTGTTCTTTCCACCACCCGGAAGTAGC 4350
CACATTTGATTTTCATTTTTGGAGGAGGGACCTCAGACTGCAAGGAGCTTGTCCTCAGGGCATTTCCAGAGAAGA 4425
TGCCCATGACCCAAGAATGTGTTGACTCTACTCTCTTTTCCATTCATTTAAAAGTCCTATATAATGTGCCCTGCT 4500
GTGGTCTCACTACCAGTTAAAGCAAAAGACTTTCAAACACGTGGACTCTGTCCTCCAAGAAGTGGCAACGGCACC 4575
TCTGTGAAACTGGATCGAATGGGCAATGCTTTGTGTGTTGAGGATGGGTGAGATGTCCCAGGGCCGAGTCTGTCT 4650
ACCTTGGAGGCTTTGTGGAGGATGCGGGCTATGAGCCAAGTGTTAAGTGTGGGATGTGGACTGGGAGGAAGGAAG 4725
GCGCAAGCCGTCCGGAGAGCGGTTGGAGCCTGCAGATGCATTGTGCTGGCTCTGGTGGAGGTGGGCTTGTGGCCT 4800
GTCAGGAAACGCAAAGGCGGCCGGCAGGGTTTGGTTTTGGAAGGTTTGCGTGCTCTTCACAGTCGGGTTACAGGC 4875
GAGTTCCCTGTGGCGTTTCCTACTCCTAATGAGAGTTCCTTCCGGACTCTTACGTGTCTCCTGGCCTGGCCCCAG 4950
GAAGGAAATGATGCAGCTTGCTCCTTCCTCATCTCTCAGGCTGTGCCTTAATTCAGAACACCAAAAGAGAGGAAC 5025
GTCGGCAGAGGCTCCTGACGGGGCCGAAGAATTGTGAGAACAGAACAGAAACTCAGGGTTTCTGCTGGGTGGAGA 5100
CCCACGTGGCGCCCTGGTGGCAGGTCTGAGGGTTCTCTGTCAAGTGGCGGTAAAGGCTCAGGCTGGTGTTCTTCC 5175
TCTATCTCCACTCCTGTCAGGCCCCCAAGTCCTCAGTATTTTAGCTTTGTGGCTTCCTGATGGCAGAAAAATCTT 5250
AATTGGTTGGTTTGCTCTCCAGATAATCACTAGCCAGATTTCGAAATTACTTTTTAGCCGAGGTTATGATAACAT 5325
CTACTGTATCCTTTAGAATTTTAACCTATAAAACTATGTCTACTGGTTTCTGCCTGTGTGCTTATGTT         5393
```

FLK-1 IS A RECEPTOR FOR VASCULAR ENDOTHELIAL GROWTH FACTOR

This is a division of application Ser. No. 08/193,829 filed Feb. 9, 1994, which is a continuation-in-part of 08/038,596 filed Mar. 26, 1993, abandoned, which is a continuation-in-part of 07/975,750 filed Nov. 13, 1992 abandoned.

1. INTRODUCTION

The present invention relates to the use of proteins, peptides and organic molecules capable of modulating FLK-1 receptor signal transduction in order to inhibit or promote angiogenesis and vasculogenesis. The invention is based, in part, on the demonstration that Flk-1 tyrosine kinase receptor expression is associated with endothelial cells and the identification of vascular endothelial growth factor (VEGF) as a high affinity ligand of Flk-1. These results indicate a major role for Flk-1 in the signaling system during vasculogenesis and angiogenesis. Engineering of host cells that express Flk-1 and the uses of expressed Flk-1 to evaluate and screen for drugs and analogs of VEGF involved in Flk-1 modulation by either agonist or antagonist activities is described.

The invention also relates to the use of FLK-1 ligands, including VEGF agonists and antagonists, in the treatment of disorders, including cancer, by modulating vasculogenesis and angiogenesis.

2. BACKGROUND OF THE INVENTION

Receptor tyrosine kinases comprise a large family of transmembrane receptors for polypeptide growth factors with diverse biological activities. Their intrinsic tyrosine kinase function is activated upon ligand binding, which results in phosphorylation of the receptor and multiple cellular substrates, and subsequently in a variety of cellular responses (Ullrich A. and Schlessinger, J., 1990, Cell 61:203–212).

A receptor tyrosine kinase cDNA, designated fetal liver kinase 1 (Flk-1), was cloned from mouse cell populations enriched for hematopoietic stem and progenitor cells. The receptor was suggested to be involved in hematopoietic stem cell renewal (Matthews et al., 1991, Proc. Natl. Acad. Sci. USA 88:9026–9030). Sequence analysis of the Flk-1 clone revealed considerable homology with the c-Kit subfamily of receptor kinases and in particular to the Flt gene product. These receptors all have in common an extracellular domain containing immunoglobulin-like structures.

The formation and spreading of blood vessels, or vasculogenesis and angiogenesis, respectively, play important roles in a variety of physiological processes such as embryonic development, wound healing, organ regeneration and female reproductive processes such as follicle development in the corpus luteum during ovulation and placental growth after pregnancy. Uncontrolled angiogenesis can be pathological such as in the growth of solid tumors that rely on vascularization for growth.

Angiogenesis involves the proliferation, migration and infiltration of vascular endothelial cells, and is likely to be regulated by polypeptide growth factors. Several polypeptides with in vitro endothelial cell growth promoting activity have been identified. Examples include acidic and basic fibroblastic growth factor, vascular endothelial growth factor and placental growth factor. Although four distinct receptors for the different members of the FGF family have been characterized, none of these have as yet been reported to be expressed in blood vessels in vivo.

While the FGFs appear to be mitogens for a large number of different cell types, VEGF has recently been reported to be an endothelial cell specific mitogen (Ferrara, N. and Henzel, W. J., 1989, Biochem. Biophys. Res. Comm. 161:851–858). Recently, the fms-like tyrosine receptor, flt, was shown to have affinity for VEGF (DeVries,C. et al. , 1992, Science 255:989–991).

3. SUMMARY OF THE INVENTION

The present invention relates to the use of peptides, proteins and organic molecules capable of modulating FLK-1 receptor signal transduction in order to inhibit or promote angiogenesis and/or vasculogenesis. The present invention is based, in part, on the discovery that the Flk-1 tyrosine kinase receptor is expressed on the surface of endothelial cells and the identification of vascular endothelial growth factor (VEGF) as a high affinity ligand of Flk-1. The role of endothelial cell proliferation and migration during angiogenesis and vasculogenesis indicate an important role for Flk-1 in these processes. The invention is described by way of example for the murine Flk-1, however, the principles may be applied to other species including humans.

Pharmaceutical reagents designed to inhibit the Flk-1/VEGF interaction may be useful in inhibition of tumor growth. VEGF and/or VEGF agonists may be used to promote wound healing. The invention relates to expression systems designed to produce Flk-1 protein and/or cell lines which express the Flk-1 receptor. Expression of soluble recombinant Flk-1 protein may be used to screen peptide libraries for molecules that inhibit the Flk-1/VEGF interaction. Engineered cell lines expressing Flk-1 on their surface may be advantageously used to screen and identify VEGF agonists and antagonists.

4. BRIEF DESCRIPTION OF THE FIGURES

FIG. 1. Comparison of the Flk-1 amino acid sequence with related RTKs. Amino acid sequence comparison of Flk-1 with human KDR and rat TKr-C. A section of the sequence which is known for all three receptors is compared and only differences to the Flk-1 sequence are shown.

FIGS. 2A and 2B. Northern blot analysis of Flk-1 gene expression. FIG. 2A. Expression of Flk-1 RNA in day 9.5 to day 18.5 mouse embryos. Samples (10 $\mu$g) of total RNA from whole mouse embryos were analyzed in each lane. Positions of 28S and 18S ribosomal RNAs are marked. FIG. 2B Expression of Flk-1 mRNA in postnatal day 4 and adult brain in comparison with capillary fragments from postnatal day 4 brain. 1 $\mu$g of poly (A$^+$) RNA was loaded on each lane. The 5' 2619 bp of the Flk-1 cDNA were used as a probe. Control hybridization with a GAPDH cDNA probe is shown in the lower panel.

Figure 3B:
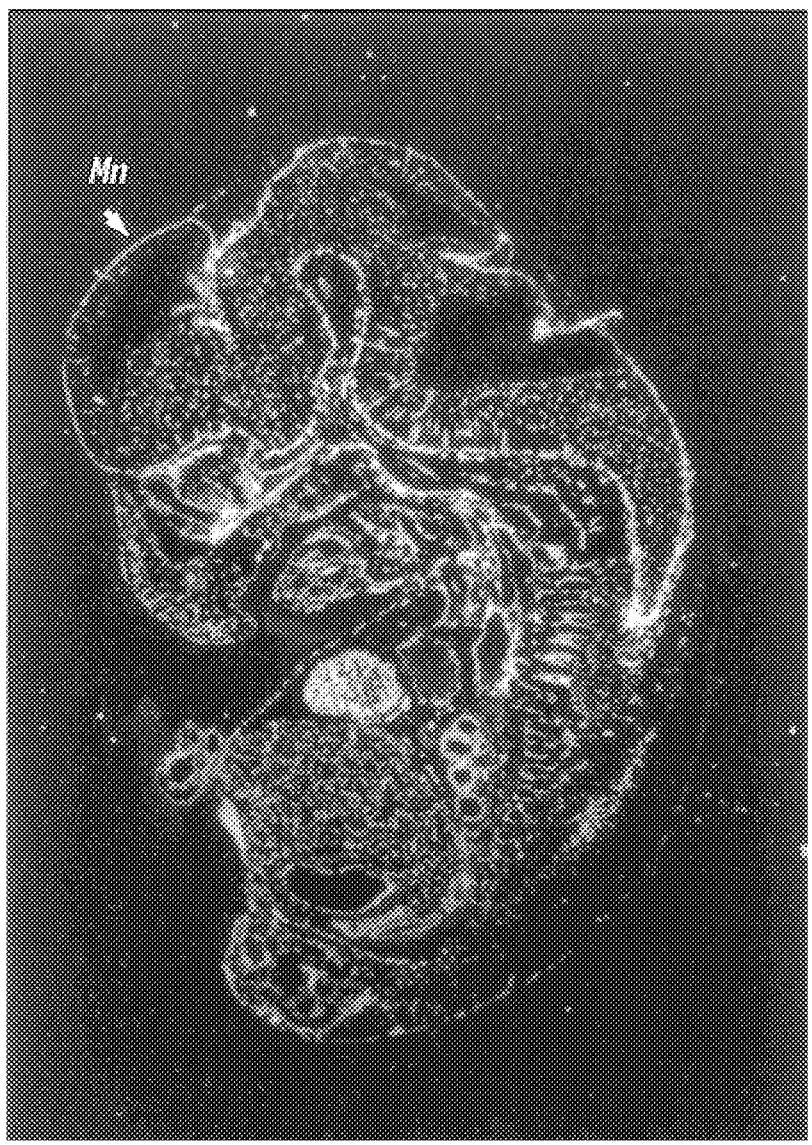
Figure 3C:

FIGS. 3A, 3B and 3C. Abundant Flk-1 gene expression in embryonic tissues. In situ hybridization analysis of Flk-1 expression in day 14.5 mouse embryo. FIG. 3A Bright field illumination of a parasagittal section through the whole embryo hybridized with a $^{35}$S-labeled antisense probe (5' 2619 bp). FIG. 3B Dark field illumination of the same section. FIG. 3C Control hybridization of an adjacent section with a sense probe. Abbreviations: Ao, aorta; At, atrium; L, lung; Li, liver; Ma, mandible; Mn, meninges; Ms. mesencephalon; T, telencephalon; V, ventricle; Vt, vertebrae.

Figure 4C:
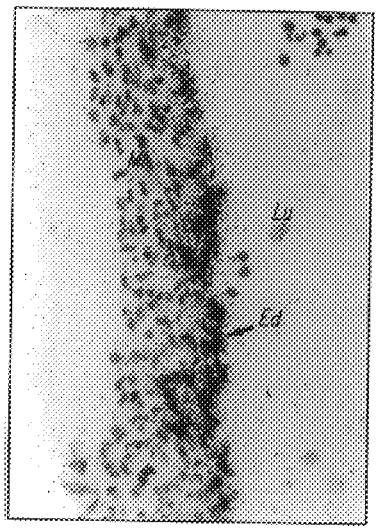
Figure 4D:
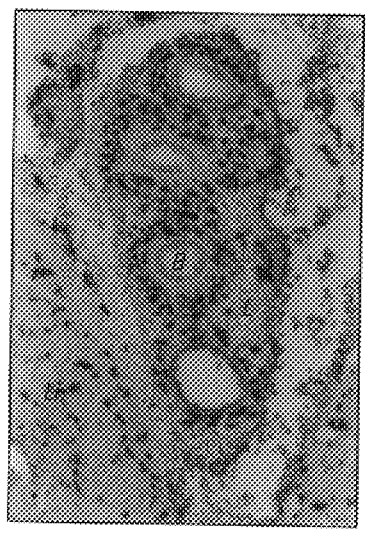
Figure 4E:

FIGS. 4A, 4B, 4C, 4D and 4E. Expression of Flk-1 RNA in embryonic organs is restricted to specific cells. Expression of Flk-1 RNA in a day 14.5 mouse embryo at higher magnification. FIG. 4A The heart region was probed with a $^{35}$S-labeled antisense probe. FIG. 4B Adjacent section hybridized with the sense probe. FIG. 4C Part of the aorta wall shown on the cellular level. The endothelial cell-layer is indicated by an arrow. FIG. 4D The lung, probed with the Flk-1 antisense probe. FIG. 4E Control hybridization of an adjacent section hybridized with the sense probe. Abbreviations: At, atrium; B, bronchus; Ed, endothelial cell layer; En, endocardium; L, lung, Li, liver; Lu, lumina of the aorta; Ml, muscular; My, myocardium.

Figure 5C:
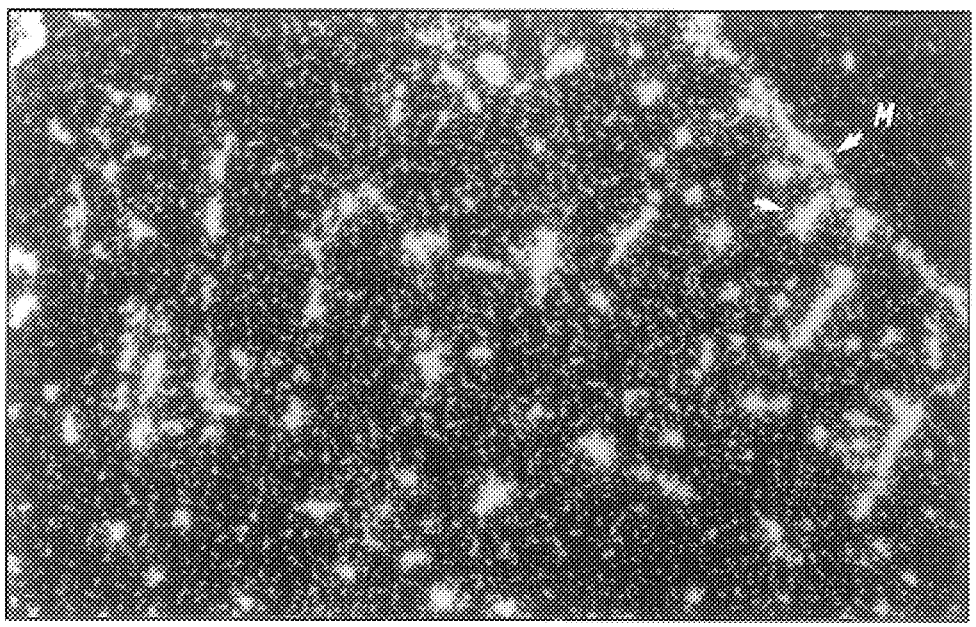
Figure 5D:
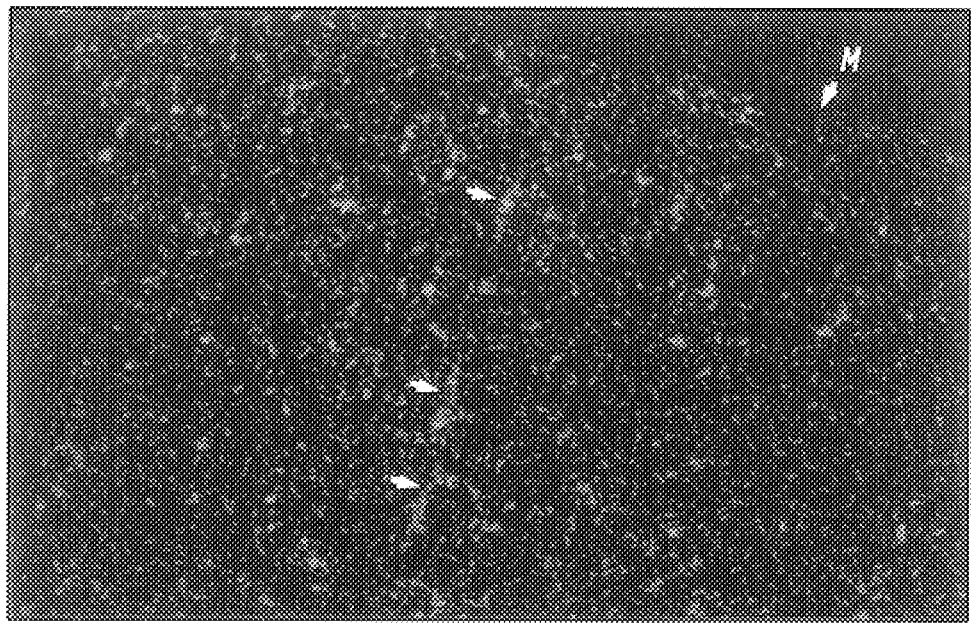

FIGS. 5A, 5B, 5C and 5D. Flk-1 gene expression in the brain of the developing mouse. In situ hybridization analysis of Flk-1 gene expression in the brain at different developmental stages. All sections were probed with the Flk-1 antisense probe. FIG. 5A Sagittal section of the telencephalon of a day 11.5 mouse embryo. A single blood vessel expressing Flk-1, which sprouts from the meninges into the neuroectoderm, is indicated by an arrow. FIG. 5B Sagittal sections of the brain of embryo day 14.5 and FIG. 5C of postnatal day 4. Shown are regions of the mesencephalon. Branching capillaries and blood vessels expressing Flk-1 are indicated by an arrow. FIG. D Sagittal section of an adult brain; a region of the mesencephalon is shown. Cells expressing Flk-1 are indicated by an arrow. Abbreviations: M, meninges; V, ventricle;

FIG. 6A and 6B. Expression of Flk-1 in the choroid plexus of adult brain. FIG. 6A Darkfield illumination of the choroid plexus of an adult mouse brain hybridized with Flk-1 antisense probe. FIG. 6B Choroid plexus shown at a higher magnification. Arrows indicate single cells, which show strong expression of Flk-1 Abbreviations: CP, choroid plexus; E, ependyme; Ep, epithelial cells; V, ventricle.

FIGS. 7A, 7B, 7C and 7D. Flk-1 is expressed in the glomeruli of the kidney. FIG. 7A Parasagittal section of a 4-day postnatal kidney, hybridized with the Flk-1 antisense probe. Hybridization signal accumulates in the glomeruli, as indicated by arrowheads. FIG. 7B Control hybridization of an adjacent section with the sense probe. FIG. 7C Sagittal section of an adult kidney probed with Flk-1. Arrowheads indicate glomeruli. FIG. 7D Glomerulus of an adult kidney at a higher magnification. The arrows in (A) and (D) indicate cells aligned in strands in the juxtaglomerular region expressing Flk-1.

Figure 8A:
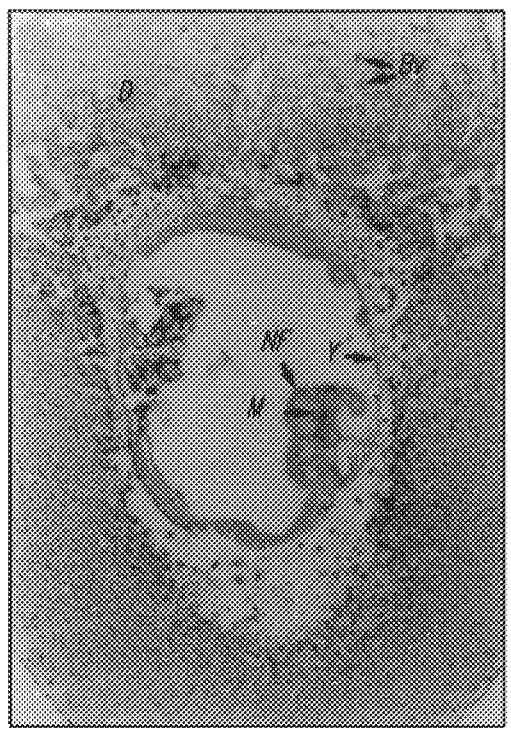
Figure 8B:
Figure 8C:
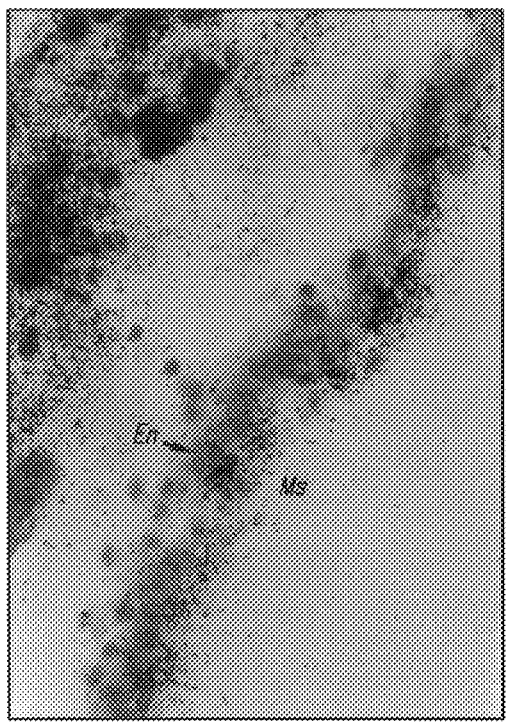
Figure 8D:
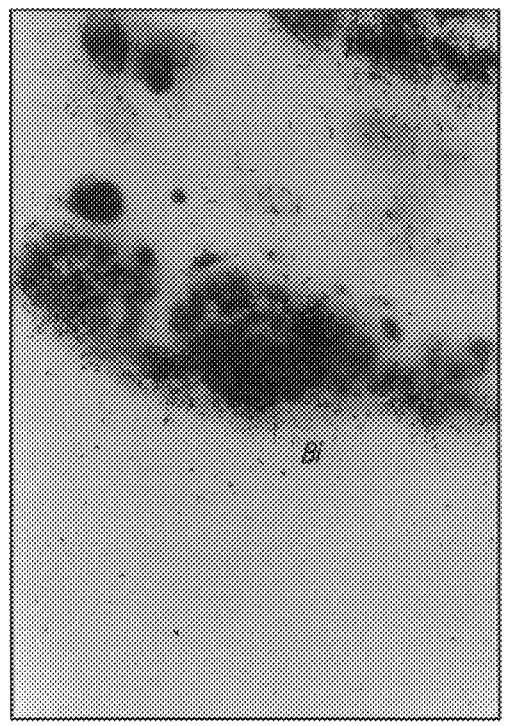

FIGS. 8A, 8b, 8C and 8D. In situ hybridization analysis of Flk-1 expression in early embryos and extraembryonic tissues. FIG. 8A Sagittal section of a day 8.5 mouse embryo in the maternal deciduum probed with Flk-1. FIG. 8B Higher magnification of the deciduum. Arrowheads indicate the endothelium of maternal blood vessels strongly expressing Flk-1 RNA. FIG. 8C High magnification of the yolk sac and the trophectoderm of a day 9.5 mouse embryo. FIG. 8D High magnification of a blood island. Abbreviations: A, allantois; Bi, blood island; Bv, maternal blood vessel; D, deciduum; En, endodermal layer of yolk sac; M, mesenchyme; Ms, mesodermal layer of yolk sac; NF, neural fold; T, trophoblast; Y, yolk sac.

Figure 9A:
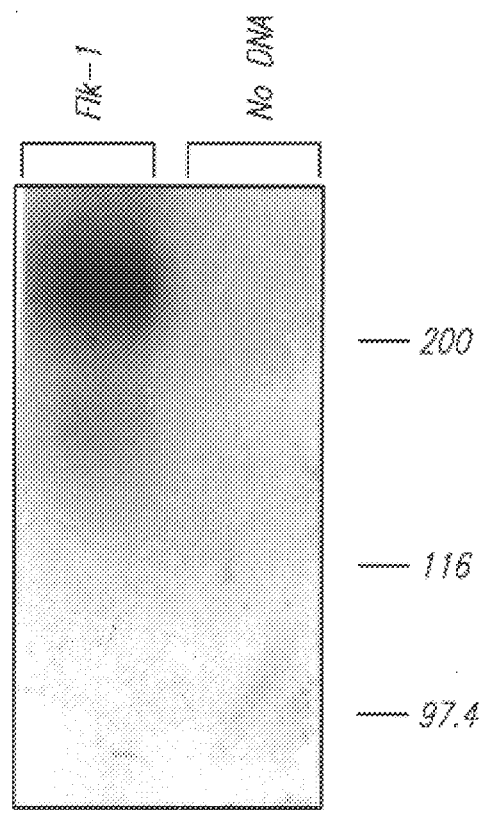
Figure 9B:
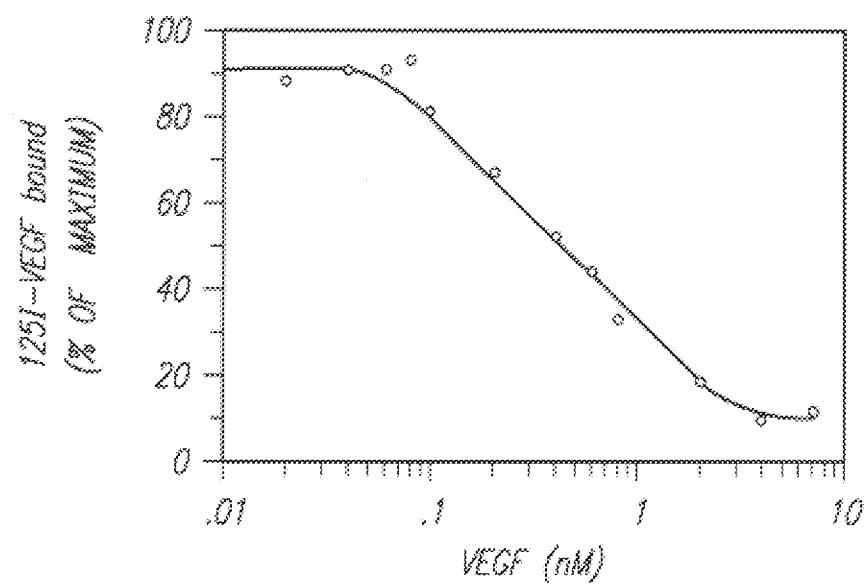

FIGS. 9A and 9B. Flk-1 is a receptor for VEGF. FIG. 9A Cross linking of $^{125}$I-VEGF to COS cells transiently expressing the Flk-1 receptor and control cells were incubated with $^{125}$I-VEGF at 4° C. overnight, then washed twice with phosphate buffered saline (PBS) and exposed to 0.5 mM of the cross linking agent DSS in PBS for 1 hour at 4° C. The cells were lysed, Flk-1 receptor immunoprecipitated, and analyzed by polyacrylamide gel electrophoresis followed by autoradiography. Molecular size markers are indicated in kilodaltons. FIG. 9B Specific binding of $^{125}$I-VEGF to COS cells expressing Flk-1. COS cells transiently expressing Flk-1 were removed from the plate and resuspended in binding medium (DMEM, 25 mM Hepes, 0.15% gelatin). Binding was performed at 15° C. for 90 minutes in a total volume of 0.5 ml containing $2 \times 10^5$ cells, 15,000 cpm $^{125}$I-VEGF, and the indicated concentrations of unlabeled ligand. The cells were washed twice with PBS / 0.1% BSA and counted in a gamma counter.

Figure 10:
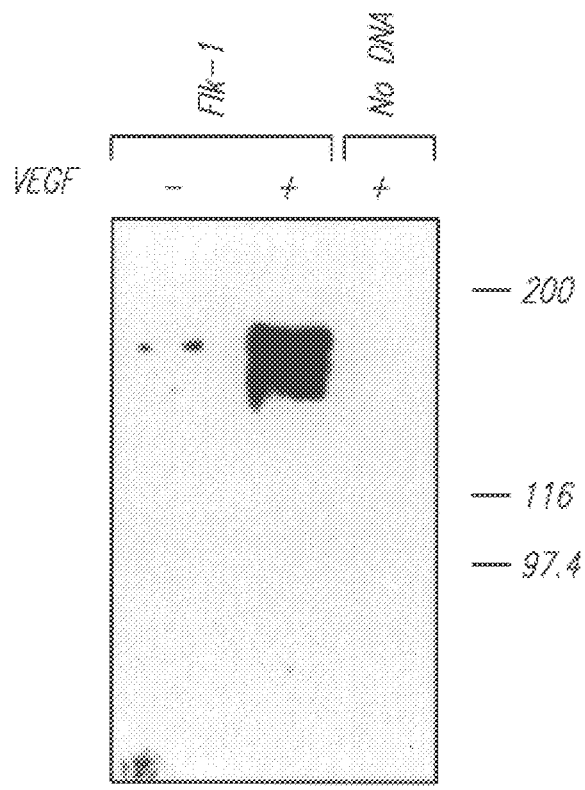

FIG. 10. VEGF-induced autophosphorylation of Flk-1. COS cells transiently expressing Flk-1 receptor and control cells were starved for 24 hours in DMEM containing 0.5% fetal calf serum and then stimulated with VEGF for 10 minutes as indicated. The cells were solubilized, Flk-1 receptor immunoprecipitated with a polyclonal antibody against its C-terminus, separated by polyacrylamide gel electrophoresis, and transferred to nitrocellulose. The blot was probed with antiphosphotyrosine antibodies (5B2). The protein bands were visualized by using a horseradish-peroxidase coupled secondary antibody and BCL™ (Amersham) detection assay.

FIGS. 11A and 11B. Nucleotide Sequence of Murine Flk-1.

Figure 12A:
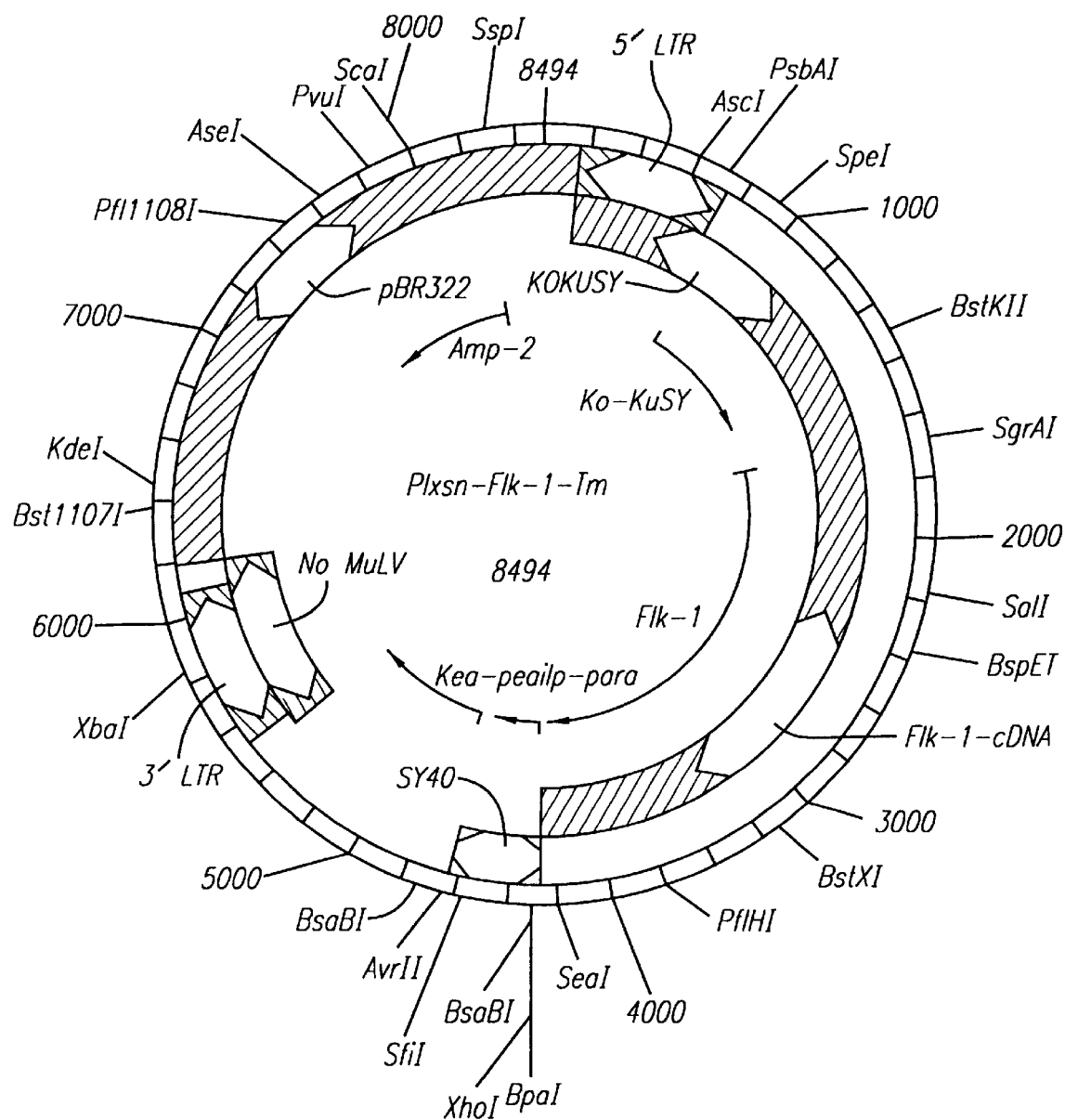
Figure 12B:
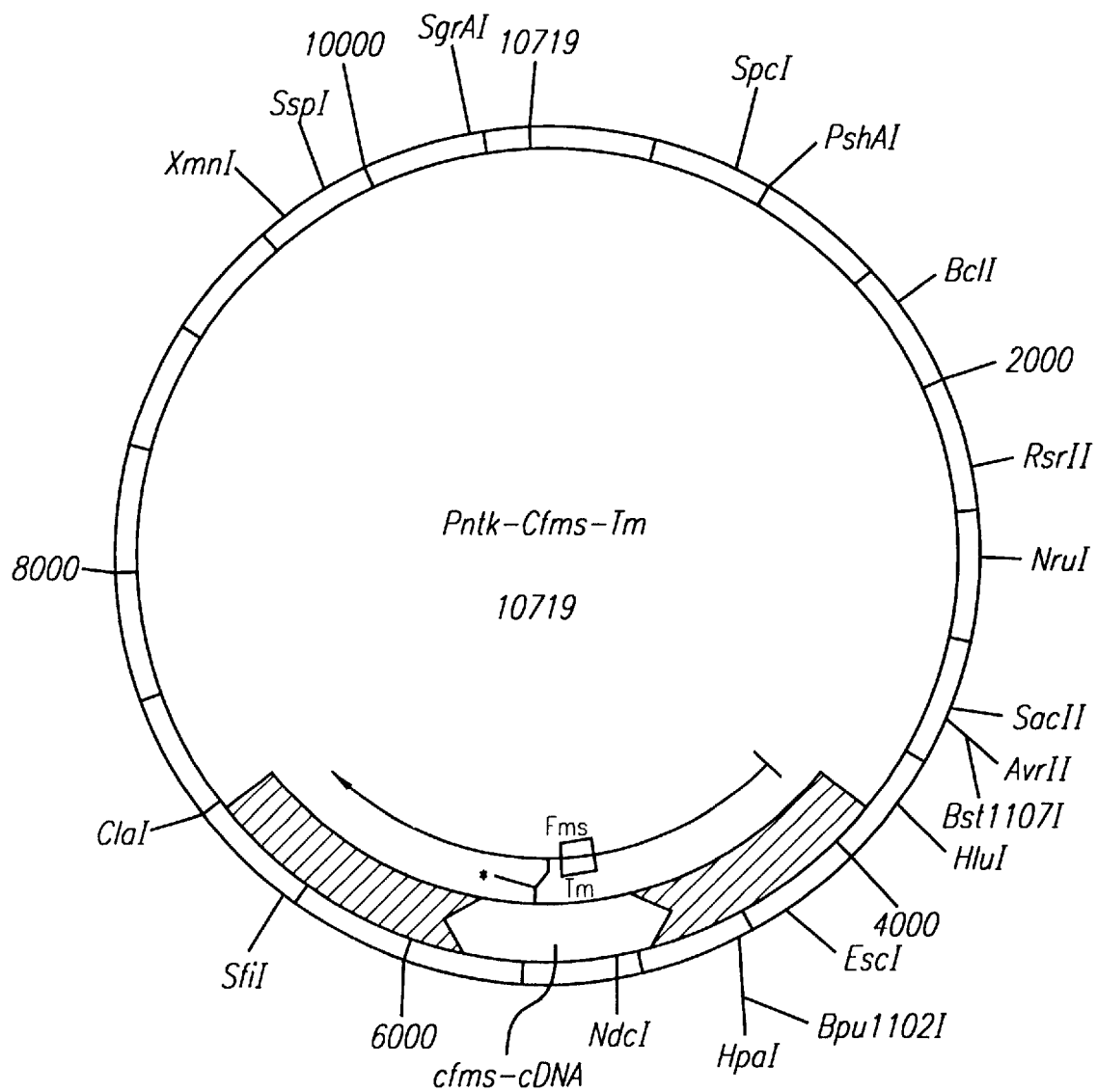

FIGS. 12A and 12B. Plasmid Maps of retroviral vector constructs. FIG. 12A. pLXSN Flk-1 TM cl.1 and pLXSN Flk-1 TM cl.3, clonal isolates of pLXSN Flk-1 TM, contain Flk-1 amino acids 1 through 806 and lack 561 C-terminal amino acids of the intracellular kinase domain. FIG. 12B. pNTK-cfms-TM contains the 541 N-terminal amino acids of the CSF-1 receptor/c-fms.

Figure 13:
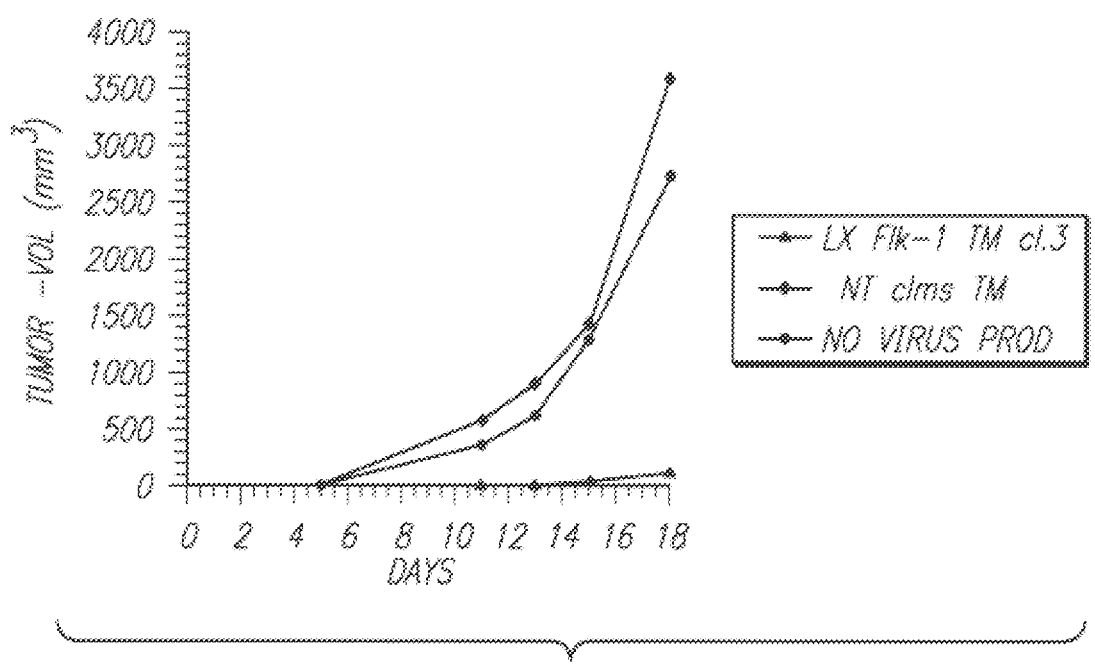

FIG. 13. Inhibition of C6 glioblastoma tumor growth by transdominant-negative inhibition of Flk-1. C6 cells were implanted either alone or coimplanted with virus-producing cells. Cell numbers are as indicated in each panel. Two different virus-producing cells lines were used: one expressing the Flk-1 TM (transdominant-negative) mutant and one expressing a transdominant-negative c-fms mutant (c-fms TM) as a control. Beginning at the time when the first tumors appeared, tumor volumes were measured every 2 to 3 days to obtain a growth curve. Each group is represented by four mice.

Figure 14:
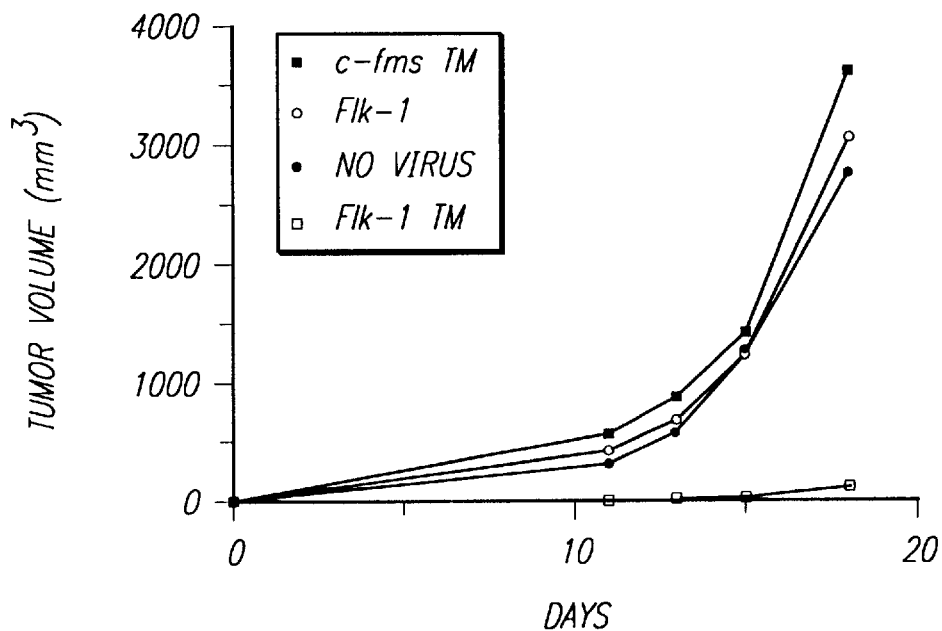

FIG. 14. A second experiment showing inhibition of C6 glioblastoma tumor growth by transdominant-negative inhibition of Flk-1 . C6 cells were implanted either alone or coimplanted with virus-producing cells. Cell numbers are as indicated in each panel. Two different virus-producing cell lines were used: one expressing the Flk-1 TM (transdominant-negative) mutant and one expressing a transdominant-negative c-fms mutant (cfms TM) as a control. Beginning at the time when the first tumor appeared, tumor volumes were measured every 2 to 3 days to obtain growth curve. Each group is represented by four mice.

Figure 15:
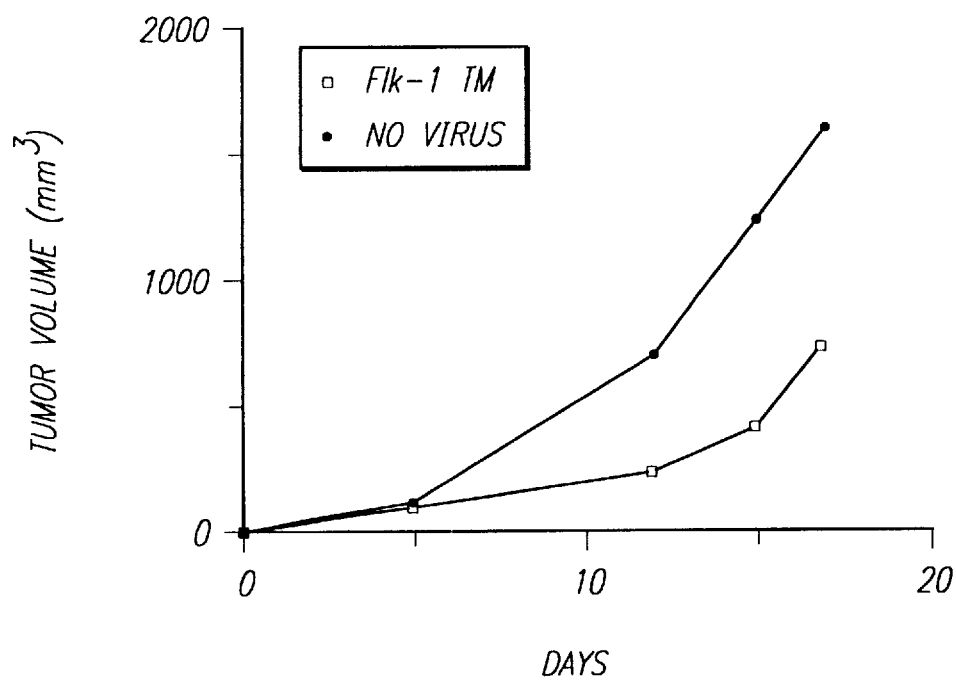

FIG. 15. Inhibition of C6 glioblastoma tumor growth by localized injection of retroviral supernatants. $1 \times 10^6$ cells were subcutaneously implanted in nude mice. Starting at day 5 after implantation (denoted by the arrow), the growing tumors were treated by injection of 100 $\mu$l retroviral supernatants (about 105 virus particles) into the site of tumor implantation. Tumor volumes were measured twice a week.

Figure 16A:
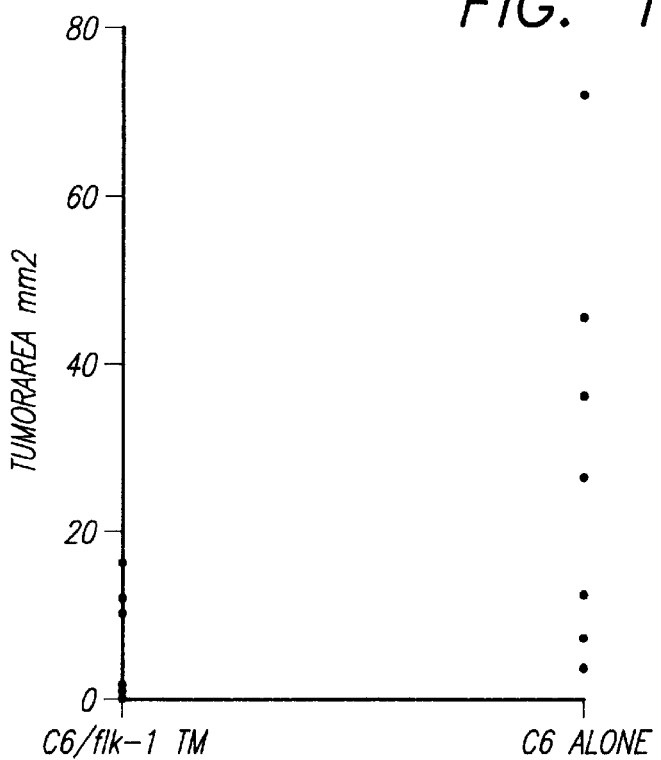
Figure 16B:
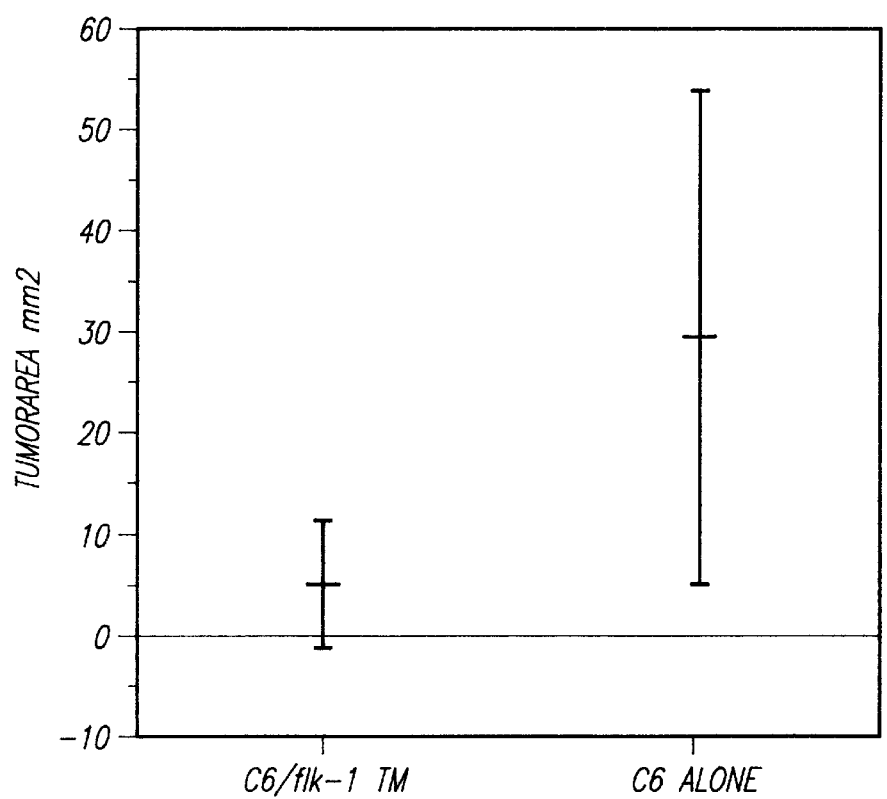

FIG. 16A and 16B. Inhibition of C6 glioblastoma tumor growth by localized injection of retroviral supernatants. C6 cells implanted intercranially in rats, either alone or co-implanted with virus producing cells expressing the Flk-1 TM (transdominant negative) mutant. Each group is represented by 8 rats. Cell numbers are as indicated in Example 6.1.13. FIG. 16A shows the distribution of tumor size in each rat. FIG. 16B shows the median tumor area for each of the two groups of rats.

Figure 17:
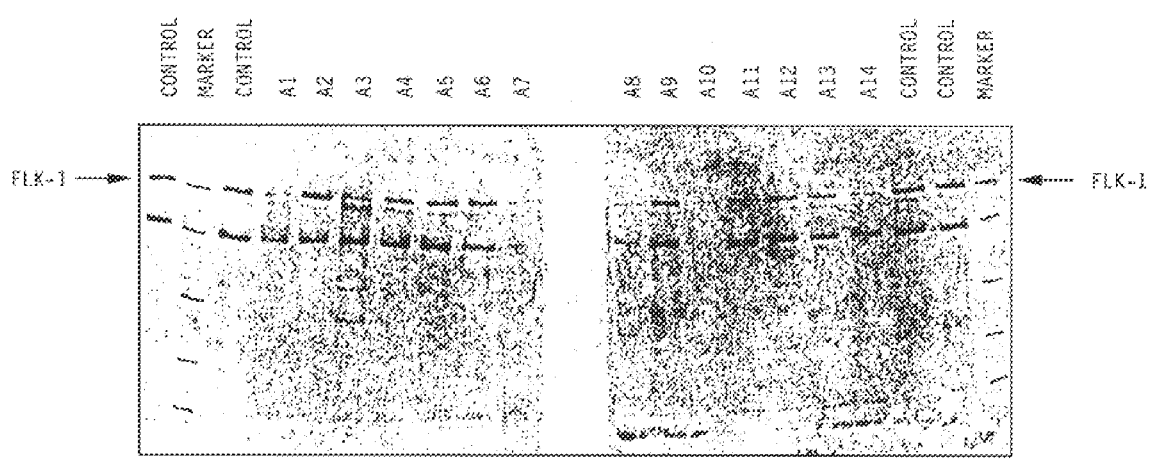

FIG. 17. Inhibition of VEGF stimulatory activity of Flk-1. Test compounds and VEGF were co-incubated on cells expressing the Flk-1 receptor. The level of tyrosine phosphorylation was measured in a Western blot format using an antiphosphotyrosine antibody. Compound A14 completely inhibited the ability of VEGF to stimulate autophosphorylation of Flk-1. (Compounds A7, A8, and A10 were toxic to these cells resulting in cell death.)

5. DETAILED DESCRIPTION OF THE INVENTION

The present invention relates to the use of peptides, proteins, and organic molecules capable of modulating FLK-1 receptor signal transduction in order to inhibit or promote angiogenesis and/or vasculogenesis. More specifically, the invention is directed to VEGF, a natural ligand for Flk-1, as well as VEGF agonists and antagonists, anti-VEGF and anti-Flk-1 antibodies, and VEGF and Flk-1 encoding polynucleotides, all of which may find use in modulating Flk-1 signal transduction. Another aspect of the invention relates to the use of Flk-1 expressing cells to evaluate and screen proteins, peptides, and organic compounds that may be involved in Flk-1 receptor activation, regulation and/or uncoupling. Such regulators of Flk-1 may be used therapeutically. For example, agonists of VEGF may be used in processes such as wound healing; in contrast, antagonists of VEGF may be used in-the treatment of tumors that rely on vascularization for growth.

The invention, is based, in part, on results from in situ-hybridization and Northern blot analyses indicating that Flk-1 is an endothelial cell specific RTK. In addition, cross-linking experiments have shown Flk-1 to be a high affinity receptor for vascular endothelial growth factor (VEGF), indicating that Flk-1 plays a crucial role in the development and differentiation of hemangioblast and in subsequent endothelial cell growth during vasculogenesis and angiogenesis.

The invention is based, also, on the discovery that expression of a transdominant-negative mutant form of the Flk-1 molecule can inhibit the biological activity of the endogenous wild type Flk-1. Experiments are described herein, in which tumor cells and cells expressing retrovirally-encoded truncated, signalling-incompetent Flk-1 receptor were injected into mice. In these experiments, the cells producing a recombinant retrovirus encoding a truncated Flk-1 receptor were either co-injected with the tumor cells or injected 5 days after injection of the tumor cells. Inhibition of vasculogenesis and growth of the injected tumor cells was observed in mice expressing the truncated form of the Flk-1 receptor. Inhibition of tumor growth observed when the truncated Flk-1 receptor was injected 5 days after injection of the tumor cells indicates that even established tumors may be suppressed by Flk-1 dominant-negative action. Thus, the invention provides a method of inhibiting the biological activity of signalling-competent Flk-1 receptors comprising introducing a signalling-incompetent Flk-1 receptor mutant into or in the vicinity of cells expressing such signalling-competent Flk-1 receptors. Accordingly, expression of transdominant negative forms of the Flk-1 molecule may be useful for treatment of diseases resulting from VEGF and/or Flk-1 mediated, abnormal proliferation of blood vessels, such as rheumatoid arthritis, retinopathies and growth of solid tumors.

As explained in the working examples, infra, the polymerase chain reaction (PCR) method was used to isolate new receptor tyrosine kinases specifically expressed in post-implantation embryos and endothelial cells. One such clone was found to encode a RTK that had almost identical sequence homology with the previously identified cDNA clone isolated from populations of cells enriched for hematopoietic cells and designated fetal liver kinase-1 (Flk-1) (Matthews et al., 1991, Proc. Natl. Acad Sci. U.S.A. 88:9026–9030) (FIGS. 11A and 11B).

For clarity of discussion, the invention is described in the subsections below by way of example for the murine Flk-1. However, the principles may be analogously applied to clone and express the Flk-1 of other species including humans.

5.1. THE Flk-1 CODING SEQUENCE

The nucleotide coding sequence and deduced amino acid sequence of the murine Flk-1 gene is depicted in FIGS. 11A and 11B (SEQ. ID NO. 1) and has recently been described in Matthews et al., 1991, Proc. Natl. Acad. Sci. U.S.A., 88:9026–9030. In accordance with the invention, the nucleotide sequence of the Flk-1 protein or its functional equivalent in mammals, including humans, can be used to generate recombinant molecules which direct the expression of Flk-1; hereinafter, this receptor will be referred to as "Flk-1", regardless of the species-from which it is derived.

In a specific embodiment described herein, the murine Flk-1 gene was isolated by performing a polymerase chain reaction (PCR) using two degenerate oligonucleotide primer pools that were designed on the basis of highly conserved sequences within the kinase domain of receptor tyrosine kinases (Hanks et al., 1988,) As a template, DNA from a λgt10 cDNA library prepared from day 8.5 mouse embryos, was used. In a parallel approach, similar primers were used to amplify RTK cDNA sequences from capillary endothelial cells that had been isolated from the brains of post-natal day 4–8 mice. This is a time when brain endothelial cell proliferation is maximal. Both approaches yielded cDNA sequences encoding the recently described fetal liver RTK, Flk-1 (Matthews et al., 1991). Based on amino acid homology, this receptor is a member of the type III subclass of RTKs (Ullrich and Schlessinger) which contain immunoglobulin-like repeats in their extracellular domains (FIG. 1).

The invention also relates to Flk-1 genes isolated from other species, including humans, in which Flk-1 activity exists. Members of the Flk-1 family are defined herein as those receptors that bind VEGF or fragments of the peptide. Such receptors may demonstrate about 80% homology at the amino acid level in substantial stretches of DNA sequence. A bacteriophage cDNA library may be screened, under conditions of reduced stringency, using a radioactively labeled fragment of the mouse Flk-1 clone. Alternatively the mouse Flk-1 sequence can be used to design degenerate or fully degenerate oligonucleotide probes which can be used as PCR probes or to screen bacteriophage cDNA libraries. A polymerase chain reaction (PCR) based strategy may be used to clone human Flk-1. Two pools of degenerate oligonucleotides, corresponding to a conserved motif between the mouse Flk-1 and receptor tyrosine kinases, may be designed to serve as primers in a PCR reaction. The template for the reaction is cDNA obtained by reverse transcription of mRNA prepared from cell lines or tissue known to express human Flk-1. The PCR product may be subcloned and sequenced to insure that the amplified sequences represent the Flk-1 sequences. The PCR fragment may be used to isolate a full length Flk-1 cDNA clone by radioactively labeling the amplified fragment and screening a bacteriophage cDNA library. Alternatively, the labeled fragment may be used to screen a genomic library. For a review of cloning strategies which may be used, see e.g., Maniatis, 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.)

Isolation of a human Flk-1 cDNA may also be achieved by construction of a cDNA library in a mammalian expression vector such as pcDNA1, that contains SV40 origin of replication sequences which permit high copy number expression of plasmids when transferred into COS cells. The expression of Flk-1 on the surface of transfected COS cells may be detected in a number of ways, including the use of a labeled ligand such as VEGF or a VEGF agonist labeled with a radiolabel, fluorescent label or an enzyme. Cells expressing the human Flk-1 may be enriched by subjecting transfected cells to a FACS (fluorescent activated cell sorter) sort.

In accordance with the invention, Flk-1 nucleotide sequences which encode Flk-1, peptide fragments of Flk-1, Flk-1 fusion proteins or functional equivalents thereof may be used to generate recombinant DNA molecules that direct the expression of Flk-1 protein or a functional equivalent thereof, in appropriate host cells. Alternatively, nucleotide sequences which hybridize to portions of the Flk-1 sequence may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the cloning and expression of the Flk-1 protein. Such DNA sequences include those which are capable of hybridizing to the murine Flk-1 sequence under stringent conditions.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the Flk-1 sequence, which result in a silent change thus producing a functionally equivalent Flk-1. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, analine; asparagine, glutamine; serine, threonine; phenylalanine, tyrosine. As used herein, a functionally equivalent Flk-1 refers to a receptor which binds to VEGF or fragments, but not necessarily with the same binding affinity of its counterpart native Flk-1.

The DNA sequences of the invention may be engineered in order to alter the Flk-1 coding sequence for a variety of ends including but not limited to alterations which modify processing and expression of the gene product. For example, mutations may be introduced using techniques which are well known in the art, e.g. site-directed mutagenesis, to insert new restriction sites, to alter glycosylation patterns, phosphorylation, etc. For example, in certain expression systems such as yeast, host cells may over glycosylate the gene product. When using such expression systems it may be preferable to alter the Flk-1 coding sequence to eliminate any N-linked glycosylation site.

In another embodiment of the invention, the Flk-1 or a modified Flk-1 sequence may be ligated to a heterologous sequence to encode a fusion protein. For example, for screening of peptide libraries it may be useful to encode a chimeric Flk-1 protein expressing a heterologous epitope that is recognized by a commercially available antibody. A fusion protein may also be engineered to contain a cleavage site located between the Flk-1 sequence and the heterologous protein sequence, so that the Flk-1 can be cleaved away from the heterologous moiety.

In an alternate embodiment of the invention, the coding sequence of Flk-1 could be synthesized in whole or in part, using chemical methods well known in the art. See, for example, Caruthers,-et al., 1980, Nuc. Acids Res. Symp. Ser. 7:215–233; Crea and Horn, 180, Nuc. Acids Res. 9(10):2331; Matteucci and Caruthers, 1980, Tetrahedron Letters 21:719; and Chow and Kempe, 1981, Nuc. Acids Res. 9(12):2807–2817. Alternatively, the protein itself could be produced using chemical methods to synthesize the Flk-1 amino acid sequence in whole or in part. For example, peptides can be synthesized by solid phase techniques, cleaved from the resin, and purified by preparative high performance liquid chromatography. (E.g., see Creighton, 1983, Proteins Structures And Molecular Principles, W. H. Freeman and Co., N.Y. pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49).

5.2. EXPRESSION OF Flk-1 RECEPTOR AND GENERATION OF CELL LINES THAT EXPRESS Flk-1

In order to express a biologically active Flk-1, the nucleotide sequence coding for Flk-1, or a functional equivalent as described in Section 5.1 supra, is inserted into an appropriate expression vector, i.e., a vector which contains the necessary elements for the transcription and translation of the inserted coding sequence. The Flk-1 gene products as well as host cells or cell lines transfected or transformed with recombinant Flk-1 expression vectors can be used for a variety of purposes. These include but are not limited to generating antibodies (i.e., monoclonal or polyclonal) that bind to the receptor, including those that competitively inhibit binding of VEGF and "neutralize" activity of Flk-1 and the screening and selection of VEGF analogs or drugs-that act via the Flk-1 receptor; etc.

5.2.1. EXPRESSION SYSTEMS

Methods which are well known to those skilled in the art can be used to construct expression vectors containing the Flk-1 coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the Flk-1 coding sequence. These include but are not limited to microorganisms such as bacteria transformed with recombinant bacteriophage DNA, plasmid DNA or cosmid DNA expression vectors containing the Flk-1 coding sequence; yeast transformed with recombinant yeast expression vectors containing the Flk-1 coding sequence; insect cell systems infected with recombinant virus expression vectors (e.g., baculovirus) containing the Flk-1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the Flk-1 coding sequence; or animal cell systems infected with recombinant virus expression vectors (e.g., adenovirus, vaccinia virus) including cell lines engineered to contain multiple copies of the Flk-1 DNA either stably amplified (CHO/dhfr)-or unstably amplified in double-minute chromosomes (e.g., murine cell lines).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the Flk-1 DNA SV40-, BPV- and EBV-based vectors may be used with an appropriate selectable marker.

In bacterial systems a number of expression vectors may be advantageously selected depending upon the use intended for the Flk-1 expressed. For example, when large quantities of Flk-1 are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., 1983, EMBO J. 2:1791), in which the Flk-1 coding sequence may be ligated into the vector in frame with the lac Z coding region so that a hybrid AS-lac Z protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the Flk-1 coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, N.Y., Section VIII, pp. 421–463; and Grierson & Corey, 1988, Plant Molecular Biology, 2d Ed., Blackie, London, Ch. 7–9.

An alternative expression system which could be used to express Flk-1 is an insect system. In one such system, *Autographa californica* nuclear polyhidrosis virus (AcNPV) is used as a vector to express foreign genes. The virus grows in *SpodoPtera frugiperda* cells. The Flk-1 coding sequence may be cloned into non-essential regions (for example the polyhedrin gene) of the virus and placed under control of an AcNPV promoter (for example the polyhedrin promoter). Successful insertion of the Flk-1 coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the Flk-1 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing Flk-1 in infected hosts. (E.g., See Logan & Shenk, 1984, Proc. Natl. Acad. Sci. (USA) 81:3655–3659). Alternatively, the vaccinia 7.5 K promoter may be used. (See, e.c., Mackett et al., 1982, Proc. Natl. Acad. Sci. (USA) 79:7415–7419; Mackett et al., 1984, J. Virol. 49:857–864; Panicali et al., 1982, Proc. Natl. Acad. Sci. 79:4927–4931).

Specific initiation signals may also be required for efficient translation of inserted Flk-1 coding sequences. These signals include the ATG initiation codon and adjacent sequences. In cases where the entire Flk-1 gene, including its own initiation codon and adjacent sequences, is inserted into the appropriate expression vector, no additional translational control signals may be needed. However, in cases where only a portion of the Flk-1 coding sequence is inserted, exogenous translational control signals, including the ATG initiation codon, must be provided. Furthermore, the initiation codon must be in phase with the reading frame of the Flk-1 coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express the Flk-1 may be engineered. Rather than using expression vectors which contain viral origins of replication, host cells can be transformed with the Flk-1 DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Flk-1 on the cell surface, and which respond to VEGF mediated signal transduction. Such engineered cell lines are particularly useful in screening VEGF analogs.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981), Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

5.2.2. IDENTIFICATION OF TRANSFECTANTS OR TRANSFORMANTS THAT EXPRESS THE Flk-1

The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of Flk-1 mRNA transcripts in the host cell; and (d) detection of the gene product as measured by immunoassay or by its biological activity.

In the first approach, the presence of the Flk-1 coding sequence inserted in the expression vector can be detected by DNA-DNA or DNA-RNA hybridization using probes comprising nucleotide sequences that are homologous to the Flk-1 coding sequence, respectively, or portions or derivatives thereof.

In the second approach, the recombinant expression vector/host system can be identified and selected based upon the presence or absence of certain "marker" gene functions (e.g, thymidine kinase activity, resistance to antibiotics, resistance to methotrexate, transformation phenotype, occlusion body formation in baculovirus, etc.). For example, if the Flk-1 coding sequence is inserted within a marker gene sequence of the vector, recombinants containing the Flk-1 coding sequence can be identified by the absence of the marker gene function. Alternatively, a marker gene can be placed in tandem with the Flk-1 sequence under the control of the same or different promoter used to control the expression of the Flk-1 coding sequence. Expression of the marker in response to induction or selection indicates expression of the Flk-1 coding sequence.

In the third approach, transcriptional activity for the Flk-1 coding region can be assessed by hybridization assays. For example, RNA can be isolated and analyzed by Northern blot using a probe homologous to the Flk-1 coding sequence or particular portions thereof. Alternatively, total nucleic acids of the host cell may be extracted and assayed for hybridization to such probes.

In the fourth approach, the expression of the Flk-1 protein product can be assessed immunologically, for example by Western blots, immunoassays such as radioimmunoprecipitation, enzyme-linked immunoassays and the like. The ultimate test of the success of the expression system, however, involves the detection of the biologically active Flk-1 gene product. A number of assays can be used to detect receptor activity including but not limited to VEGF binding assays; and VEGF biological assays using engineered cell lines as the test substrate.

5.3. USES OF THE Flk-1 RECEPTOR AND ENGINEERED CELL LINES

Angiogenesis, the growth of new blood capillary vessels, is required for a number of physiological processes ranging from wound healing, tissue and organ regeneration, placental formation after pregnancy and embryonic development. Abnormal proliferation of blood vessels is an important component of a variety of diseases such as rheumatoid arthritis, retinopathies, and psoriasis. Angiogenesis is also an important factor in the growth and metastatic activity of solid tumors that rely on vascularization. Therefore, inhibitors of angiogenesis may be used therapeutically for the treatment of diseases resulting from or accompanied by abnormal growth of blood vessels and for treatments of malignancies involving growth and spread of solid tumors.

In an embodiment of the invention the Flk-1 receptor and/or cell lines that express the Flk-1 receptor may be used to screen for antibodies, peptides, organic molecules or other ligands that act as agonists or antagonists of angiogenesis or vasculogenesis mediated by the Flk-1 receptor. For example, anti-Flk-1 antibodies capable of neutralizing the activity of VEGF, may be used to inhibit Flk-1 function. Additionally, anti-Flk-1 antibodies which mimic VEGF activity may be selected for uses in wound healing. Alternatively, screening of peptide libraries or organic compounds with recombinantly expressed soluble Flk-1 protein or cell lines expressing Flk-1 protein may be useful for identification of therapeutic molecules that function by inhibiting the biological activity of Flk-1.

In an embodiment of the invention, engineered cell lines which express the entire Flk-1 coding region or its ligand binding domain may be utilized to screen and identify VEGF antagonists as well as agonists. Synthetic compounds, natural products, and other sources of potentially biologically active materials can be screened in a number of ways. The ability of a test compound to inhibit binding of VEGF to Flk-1 may be measured using standard receptor binding techniques, such as those described in Section 6.1.9., or using any of the compound screening assays described in Section 5.3.2. and 6.1.14. The ability of agents to prevent or mimic, the effect of VEGF binding on signal transduction responses on Flk-1 expressing cells may be measured. For example, responses such as activation of Flk-1 kinase activity, modulation of second messenger production or changes in cellular metabolism may be monitored. These assays may be performed using conventional techniques developed for these purposes.

The ability of a test compound to modulate signal transduction through the VEGF-Flk-1 system may also be measured in vivo, in models such as those described in Section 6.1.12. and 6.1.13. The ability of agents to prevent the effect of VEGF binding on signal transduction responses of Flk-1 expressing cells may be measured. For example, responses such as inhibition of angiogenesis, inhibition of the development of solid tumors, or reduction of solid tumor size may be monitored.

5.3.1. SCREENING OF PEPTIDE LIBRARY WITH Flk-1 PROTEIN OR ENGINEERED CELL LINES

Random peptide libraries consisting of all possible combinations of amino acids attached to a solid phase support may be used to identify peptides that are able to bind to the ligand binding site of a given receptor or other functional domains of a receptor such as kinase domains (Lam, K. S. et al., 1991, Nature 354: 82–84). The screening of peptide libraries may have therapeutic value in the discovery of pharmaceutical agents that act to inhibit the biological activity of receptors through their interactions with the given receptor.

Identification of molecules that are able to bind to the Flk-1 may be accomplished by screening a peptide library with recombinant soluble Flk-1 protein. Methods for expression and purification of Flk-1 are described in Section 5.2.1 and may be used to express recombinant full length Flk-1 or fragments of Flk-1 depending on the functional domains of interest. For example, the kinase and extracellular ligand binding domains of Flk-1 may be separately expressed and used to screen peptide libraries.

To identify and isolate the peptide/solid phase support that interacts and forms a complex with Flk-1, it is necessary to label or "tag" the Flk-1 molecule. The Flk-1 protein may be conjugated to enzymes such as alkaline phosphatase or horseradish peroxidase or to other reagents such as fluorescent labels which may include fluorescein isothyiocynate (FITC), phycoerythrin (PE) or rhodamine. Conjugation of any given label, to Flk-1, may be performed using techniques that are routine in the art. Alternatively, Flk-1 expression vectors may be engineered to express a chimeric Flk-1 protein containing an epitope for which a commercially available antibody exist. The epitope specific antibody may be tagged using methods well known in the art including labeling with enzymes, fluorescent dyes or colored or magnetic beads.

The "tagged" Flk-1 conjugate is incubated with the random peptide library for 30 minutes to one hour at 22° C. to allow complex formation between Flk-1 and peptide species within the library. The library is then washed to remove any unbound Flk-1 protein. If Flk-1 has been conjugated to alkaline phosphatase or horseradish peroxidase the whole library is poured into a petri dish containing a substrates for either alkaline phosphatase or peroxidase, for example, 5-bromo-4-chloro-3-indoyl phosphate (BCIP) or 3,3',4,4"-diamnobenzidine (DAB), respectively. After incubating for several minutes, the peptide/solid phase-Flk-1 complex changes color, and can be easily identified and isolated physically under a dissecting microscope with a micromanipulator. If a fluorescent tagged Flk-1 molecule has been used, complexes may be isolated by fluorescent activated sorting. If a chimeric Flk-1 protein expressing a heterologous epitope has been used, detection of the peptide/Flk-1 complex may be accomplished by using a labeled epitope specific antibody. Once isolated, the identity of the peptide attached to the solid phase support may be determined by peptide sequencing.

In addition to using soluble Flk-1 molecules, in another embodiment, it is possible to detect peptides that bind to cell surface receptors using intact cells. The use of intact cells is preferred for use with receptors that are multi-subunits or labile or with receptors that require the lipid domain of the cell membrane to be functional. Methods for generating cell lines expressing Flk-1 are described in Sections 5.2.1. and 5.2.2. The cells used in this technique may be either live or fixed cells. The cells will be incubated with the random peptide library and will bind to certain peptides in the library to form a "rosette" between the target cells and the relevant solid phase support/peptide. The rosette can thereafter be isolated by differential centrifugation or removed physically under a dissecting microscope.

As an alternative to whole cell assays for membrane bound receptors or receptors that require the lipid domain of the cell membrane to be functional, the receptor molecules can be reconstituted into liposomes where label or "tag" can be attached.

5.3.2. SCREENING OF ORGANIC COMPOUNDS WITH Flk-1 PROTEIN OR ENGINEERED CELL LINES

Cell lines that express Flk-1 may be used to screen for molecules that modulate Flk-1 receptor activity or signal transduction. Such molecules may include small organic or inorganic compounds, or other molecules that modulate Flk-1 receptor activity or that promote or prevent the formation of Flk-1/VEGF complex. Synthetic compounds, natural products, and other sources of potentially biologically active materials can be screened in a number of ways.

The ability of a test molecule to interfere with VEGF-Flk-1 binding and/or Flk-1 receptor signal may be measured using standard biochemical techniques. Other responses such as activation or suppression of catalytic activity, phosphorylation or dephosphorylation of other proteins, activation or modulation of second messenger production, changes in cellular ion levels, association, dissociation or translocation of signalling molecules, or transcription or translation of specific genes may also be monitored. These assays may be performed using conventional techniques developed for these purposes in the course of screening.

Ligand binding to its cellular receptor may, via signal transduction pathways, affect a variety of cellular processes. Cellular processes under the control of the Flk-1/VEGF signalling pathway may include, but are not limited to, normal cellular functions, proliferation, differentiation, maintenance of cell shape, and adhesion, in addition to abnormal or potentially deleterious processes such as unregulated cell proliferation, loss of contact inhibition, blocking of differentiation or cell death. The qualitative or quantitative observation and measurement of any of the described cellular processes by techniques known in the art may be advantageously used as a means of scoring for signal transduction in the course of screening.

Various embodiments are described below for screening, identification and evaluation of compounds that interact with the Flk-1 receptor, which compounds may affect various cellular processes under the control of the Flk/VEGF receptor signalling pathway.

The present invention includes a method for identifying a compound which is capable of modulating signal transduction, comprising:

(a) contacting the compound with Flk-1, or a functional derivative thereof, in pure or semi-pure form, in a membrane preparation, or in a whole live or fixed cell;

(b) incubating the mixture of step (a) in the presence of VEGF, for an interval sufficient for the compound to stimulate or inhibit the signal transduction;

(c) measuring the signal transduction;

(d) comparing the signal transduction activity to that of Flk-1, incubated without the compound, thereby determining whether the compound stimulates or inhibits signal transduction.

Flk-1, or functional derivatives thereof, useful in identifying compounds capable of modulating signal transduction may have, for example, amino acid deletions and/or insertions and/or-substitutions as long as they retain significant signal transducing capacity. A functional derivative of Flk-1 may be prepared from a naturally occurring or recombinantly expressed Flk-1 by proteolytic cleavage followed by conventional purification procedures known to those skilled in the art. Alternatively, the functional derivative may be produced by recombinant DNA technology by expressing parts of Flk-1 which include the functional domain in suitable cells. Functional derivatives may also be chemically synthesized. Cells expressing Flk-1 may be used as a source of Flk-1, crude or purified, or in a membrane preparation, for testing in these assays. Alternatively, whole live or fixed cells may be used directly in those assays.

Flk-1 signal transduction activity may be measured by standard biochemical techniques or by monitoring the cellular processes controlled by the signal. To assess modulation of kinase activity, the test molecule is added to a reaction mixture containing Flk-1 and a substrate test. To assess modulation of kinase activity of the Flk-1 receptor, the test molecule is added to a reaction mixture containing the Flk-1 receptor. The kinase reaction is then initiated with the addition of VEGF and ATP. An immunoassay is performed on the kinase reaction to detect the presence or absence of the phosphorylated tyrosine residues on the substrate or to detect phosphorylated tyrosine residues on autophosphorylated Flk-1, and results are compared to those obtained for controls i.e., reaction mixtures not exposed to the test molecule. The immunoassay used to detect the phosphorylated substrate in the cell lysate or the in vitro reaction mixture may be carried out with an anti-phosphotyrosine antibody.

The invention further provides for a method of screening compounds that, upon interacting with Flk-1, elicit or trigger a signal mimicking the action of VEGF binding to the Flk-1 receptor. Signal transduction is mimicked if the cellular processes under the control of the signalling pathway are affected in a way similar to that caused by ligand binding. Such compounds may be naturally occurring or synthetically produced molecules that activate the Flk-1 receptor.

The invention also includes a method whereby a molecule capable of binding to Flk-1 in a chemical or biological preparation may be identified comprising:

(a) immobilizing Flk-1, or functional fragments thereof, to a solid phase matrix;

(b) contacting the chemical or biological preparation with the solid phase matrix produced in step (a), for an interval sufficient to allow the compound to bind;

(c) washing away any unbound material from the solid phase matrix;

(d) detecting the presence of the compound bound to the solid phase, thereby identifying the compound.

The above method may further include the step of:

(e) eluting the bound compound from the solid phase matrix, thereby isolating the compound.

The term "compound capable of binding to Flk-1" refers to a naturally occurring or synthetically produced molecule which interacts with Flk-1. Such a compound may directly or indirectly modulate Flk-1 signal transduction and may include molecules that are natively associated with the intracellular domain of Flk-1 inside a cell. Examples of such compounds are (i) a natural substrate of Flk-1; (ii) a naturally occurring molecule which is part of the signalling complex; and/or a naturally occurring signalling molecule produced by other cell types.

5.3.3. ANTIBODY PRODUCTION AND SCREENING

Various procedures known in the art may be used for the production of antibodies to epitopes of the recombinantly produced Flk-1 receptor. Such antibodies include but are not limited to polyclonal, monoclonal, chimeric, single chain, Fab fragments and fragments produced by an Fab expression library. Neutralizing antibodies i.e., those which compete for the VEGF binding site of the receptor are especially preferred for diagnostics and therapeutics.

Monoclonal antibodies that bind Flk-1 may be radioactively labeled allowing one to follow their location and distribution in the body after injection. Radioactivity tagged antibodies may be used as a non-invasive diagnostic tool for imaging de novo vascularization associated with a number of diseases including rheumatoid arthritis, macular degeneration, and formation of tumors and metastases.

Immunotoxins may also be designed which target cytotoxic agents to specific sites in the body. For example, high affinity Flk-1 specific monoclonal antibodies may be covalently complexed to bacterial or plant toxins, such as diptheria toxin, abrin or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate Flk-1 expressing endothelial cells.

For the production of antibodies, various host animals may be immunized by injection with the Flk-1 protein including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Monoclonal antibodies to Flk-1 may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce Flk-1-specific single chain antibodies.

Antibody fragments which contain specific binding sites of Flk-1 may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to Flk-1.

5.4. USES OF Flk-1 CODING SEQUENCE

The Flk-1 coding sequence may be used for diagnostic purposes for detection of Flk-1 expression. Included in the scope of the invention are oligoribonucleotide sequences, that include antisense RNA and DNA molecules and ribozymes that function to inhibit translation of Flk-1. In addition, mutated forms of Flk-1, having a dominant negative effect, may be expressed in targeted cell populations to inhibit the activity of endogenously expressed wild-type Flk-1.

5.4.1. USE OF Flk-1 CODING SEQUENCE IN DIAGNOSTICS AND THERAPEUTICS

The Flk-1 DNA may have a number of uses for the diagnosis of diseases resulting from aberrant expression of Flk-1. For example, the Flk-1 DNA sequence may be used in hybridization assays of biopsies or autopsies to diagnose abnormalities of Flk-1 expression; e.g., Southern or Northern analysis, including in situ hybridization assays.

The Flk-1 cDNA may be used as a probe to detect the expression of the Flk-1 MRNA. In a specific example described herein, the expression of Flk-1 mRNA in mouse embryos of different developmental stages was analyzed. Northern blot analysis indicated abundant expression of a major 5.5 kb mRNA between day 9.5 and day 18.5, with apparent decline towards the end of gestation (FIG. 2A). In post-natal day 4–8 brain capillaries Flk-1 mRNA was found to be highly enriched compared to total brain RNA (FIG. 2B), suggesting a role for Flk-1 in endothelial cell proliferation.

To obtain more detailed information about the expression of Flk-1 during embryonic development and during the early stages of vascular development in situ hybridization experiments were performed as described in Section 6.1.4. In situ hybridizations demonstrated that Flk-1 expression in vivo during embryonic mouse development is largely restricted to endothelial cells and their precursors (FIGS. 3A, 3B, 3C and FIGS. 4A, 4B, 4C, 4D and 4E). Flk-1 is expressed in endothelial cells during physiological processes that are characterized by endothelial cell proliferation and the temporal and spatial expression pattern found in the embryonic brain correlate precisely with the development of the neural vascular system as described by Bar (1980). Vascular sprouts originating in the perineural plexus grow radially into the neuroectoderm and branch there and these sprouts were found to express high amounts of Flk-1 mRNA (FIGS. 5A, 5B, 5C and 5D). In the early postnatal stages, endothelial cell proliferation is still evident and Flk-1 is expressed, whereas in the adult organism, after completion of the vascularization process, the decline in endothelial cell proliferation parallels a decrease in Flk-1 expression.

Also within the scope of the invention are oligoribonucleotide sequences, that include anti-sense RNA and DNA molecules and ribozymes that function to inhibit the translation of Flk-1 mRNA. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of the Flk-1 nucleotide sequence, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of Flk-1 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

5.4.2. USE OF DOMINANT NEGATIVE Flk-1 MUTANTS IN GENE THERAPY

Receptor dimerization induced by ligands, is thought to provide an allosteric regulatory signal that functions to couple ligand binding to stimulation of kinase activity. Defective receptors can function as dominant negative mutations by suppressing the activation and response of normal receptors through formation of heterodimers with wild type receptors wherein such heterodimers are signalling incompetent. Defective receptors can be engineered into recombinant veviral vectors and used in gene therapy in individuals that inappropriately express Flk-1.

The capability of Flk-1 TM to form signalling incompetent heterodimers with the 180 kD wild type Flk-1 is demonstrated in Section 6.1.12. The dominant-negative potential of Flk-1 TM used in gene therapy may be measured by examining its influence on the Flk-1/ VEGF mitogenic response or by measurement of suppression of Flk-1 transforming activity.

In an embodiment of the invention, mutant forms of the Flk-1 molecule having a dominant negative effect may be identified by expression in selected cells. Deletion or missense mutants of Flk-1 that retain the ability to form dimers with wild type Flk-1 protein but cannot function in signal transduction may be used to inhibit the biological activity of the endogenous wild type Flk-1. For example, the cytoplasmic kinase domain of Flk-1 may be deleted resulting in a truncated Flk-1 molecule that is still able to undergo dimerization with endogenous wild type receptors but unable to transduce a signal.

Abnormal proliferation of blood vessels is an important component of a variety of pathogenic disorders such as rheumatoid arthritis, retinopathies and psoriasis. Uncontrolled angiogenesis is also an important factor in the growth and metastases of solid tumors. Recombinant viruses may be engineered to express dominant negative forms of Flk-1 which may be used to inhibit the activity of the wild type endogenous Flk-1. These viruses may be used therapeutically for treatment of diseases resulting from aberrant expression or activity of Flk-1.

Expression vectors derived from viruses such as retroviruses, vaccinia virus, adeno-associated virus, herpes viruses, or bovine papilloma virus, may be used for delivery of recombinant Flk-1 into the targeted cell population. Methods which are well known to those skilled in the art can be used to construct recombinant viral vectors containing Flk-1 coding sequence. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. Alternatively, recombinant Flk-1 molecules can be reconstituted into liposomes for delivery to target cells.

In a specific embodiment of the invention, a deletion mutant of the Flk-1 receptor was engineered into a recombinant retroviral vector. Two clonal isolates of Flk-1 TM, designated pLXSN Flk-1 TM cl.1 and pLXSN Flk-1 TM cl.3, contain a truncated Flk-1 receptor containing Flk-1 amino acids 1 through 806 but lacking the 561 COOH-terminal amino acids of the intracellular kinase domain. These isolates retain transmembrane domain sequences and 23 residues of the cytoplasmic domain. To obtain virus producing cell lines, PA37 cells were transfected with the recombinant vectors and, subsequently, conditioned media containing virus were used to infect GPE cells.

To test whether expression of signaling-defective mutants inhibits endogenous Flk-1 receptor activity, C6 rat gliobastoma cells (tumor cells) and mouse cells producing the recombinant retroviruses were mixed and injected subcutaneously into nude mice. Normally, injection of tumor cells into nude mice would result in proliferation of the tumor cells and vascularization of the resulting tumor mass. Since Flk-1 is believed to be essential for formation of blood vessels, blocking Flk-1 activity by expression of a truncated receptor, might function to inhibit vascularization of the developing tumor and, thereby, inhibit its growth. As illustrated in FIGS. 13 and 14, coinjection of virus producing cells, expressing a truncated Flk-1 receptor, significantly inhibits the growth of the tumor as compared to controls receiving only tumor cells.

As illustrated in FIG. 15, a similar inhibitory effect on C6 glioma tumor growth was also observed when truncated Flk-1 receptor virus particle-containing producer cells were injected five days after implantation of $10^6$ tumor cells, indicating that even established tumors may be suppressed by Flk-1 dominant-negative action. For glioblastoma, a tumor with generally poor prognosis and resistance to all available therapies, retrovirus-mediated gene therapy may be advantageous, since non-mitotic brain tissues such as neurons, glia and quiescent endothelial cells would not be infected. Glioblastoma multiforme is the most common and most malignant tumor of astrocytic origin in human adults and accounts for more than half of all primary brain tumors (See, for example, Cecil Textbook of Medicine, Wyngaarden, Smith, Bennett (eds) WB Saunders, p.2220 (1992).

5.5. USE OF Flk-1 RECEPTOR OR LIGANDS

Receptor/ligand interaction between Flk-1 and VEGF is believed to play an important role in the signalling system during vascularization and angiogenesis. Abnormal proliferation of blood vessels is an important component of a number of diseases.

Expression of Flk-1 RNA correlates with the development of the brain and with endothelial cell proliferation suggesting that Flk-1 might be a receptor involved in mediation of signaling events in the neural vascularization process. VEGF has been shown to be a mitogenic growth factor known to act exclusively on endothelial cells (Ferrara, N. and Henzel, W. J., 1989, Biochem. Biophys. Res. Comm.

161:851–858). Cross-linking and ligand binding experiments were performed, as described in Sections 6.1.9 and 6.1.10 respectively, to determine whether VEGF is a ligand for Flk-1. The results indicate that Flk-1 is an authentic high affinity VEGF receptor (FIGS. 9A and 9B).

In one embodiment of the invention, ligands for Flk-1, the Flk-1 receptor itself, or a fragment containing its VEGF binding site, could be administered in vivo to modulate angiogenesis and/or vasculogenesis. For example, administration of the Flk-1 receptor or a fragment containing the VEGF binding site, could competitively bind to VEGF and inhibit its interaction with the native Flk-1 receptor in vivo to inhibit angiogenesis and/or vasculogenesis. Alternatively, ligands for Flk-1, including anti-Flk-1 antibodies or fragments thereof, may be used to modulate angiogenesis and/or vasculogenesis. Agonists of VEGF activity may be used to promote wound healing whereas antagonists of VEGF activity may be used to inhibit tumor growth.

The particular peptides, proteins, organic compounds or antibodies that modulate Flk-1 receptor signal transduction can be-administered to a patient either by itself, or in pharmaceutical compositions where it is mixed with suitable carriers or excipient(s).

Depending on the specific conditions being treated, these agents may be formulated and administered systemically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, or, in the case of solid tumors, directly injected into a solid tumor. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as., for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Compositions comprising a compound of the invention formulated in a compatible pharmaceutical carrier may be prepared, placed in an appropriate container, and labelled for treatment of an indicated condition. Suitable conditions indicated on the label may include treatment of a tumor, such as a glioma or glioblastoma; and inhibition of angiogenesis.

A preferred pharmaceutical carrier for hydrophobic compounds of the invention is a cosolvent system comprising benzyl alcohol, a nonpolar surfactant, a water-miscible organic polymer, and an aqueous phase. A preferred cosolvent system is the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as DMSO also may be employed, although usually at the cost of greater toxicity.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the Flk-1 receptor modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

For any compound used in the method of the invention, the therapeutically effective dose can be estimated initially from cell culture assays. For example, a dose can be formulated in animal models to achieve a circulating concentration range that includes the IC50 as determined in cell culture (i.e., the concentration of the test compound which achieves a half-maximal inhibition of the PTP activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1).

Dosage amount and interval may be adjusted individually to provide plasma levels of the active moiety which are sufficient to maintain the Flk-1 receptor-inhibitory effects. Usual patient dosages for systemic administration range from 1–2000 mg/day, commonly from 1–250 mg/day, and typically from 10–150 mg/day. Stated in terms of patient body weight, usual dosages range from 0.02–25 mg/kg/day, commonly from 0.02–3 mg/kg/day, typically from 0.2–1.5 mg/kg/day. Stated in terms of patient body surface areas, usual dosages range from 0.5–1200 mg/m$^2$/day, commonly from 0.5–150 mg/m$^2$/day, typically from 5–100 mg/m$^2$/day.

Dosage amount and interval may be adjusted individually to provide plasma levels of the active moiety which are sufficient to maintain the Flk-1 receptor-inhibitory effects. Usual average plasma levels should be maintained within 50–5000 μg/ml, commonly 50–1000 μg/ml, and typically 100–500 μg/ml Alternately, one may administer the compound in a local rather than systemic manner,-for example, via injection of the compound directly into a tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

In cases of local administration or selective uptake, the effective local concentration of the drug may not be related to plasma concentration.

6. EXAMPLE

CLONING AND EXPRESSION PATTERNS OF Flk-1, A HIGH AFFINITY RECEPTOR FOR VEGF

The subsection below describes the cloning and characterization of the Flk-1 cDNA clone. Northern blot and in situ hybridization analyses indicate that Flk-1 is expressed in endothelial cells. Cross-linking and ligand binding experiments further indicate that Flk-1 is a high affinity receptor for VEGF.

6.1. MATERIALS AND METHODS

6.1.1. CDNA CLONING OF Flk-1

DNA extracted from λgt10 cDNA library of day 8.5 mouse embryos (Fahrner et al., 1987, EMBO. J. 6:1497–1508) was used as template for polymerase chain reaction (PCR; Saiki, R. K. et al., 1985 Science 230:1350–1354). In an independent approach cDNA of capillary endothelial cells that had been isolated from the brain of postnatal day 4–8 mice was used for amplification (Risau, W., 1990 In: development of the Vascular System. Issues Biomed. Basel Karger 58–68 and Schnurch et al., unpublished) Degenerated primers were designed on the basis of high amino acid homologies within the kinase domain shared by all RTKs (Wilks, A. F., 1989, Proc. Natl. Acad. Sci. U.S.A. 86:1603–1607).

Full length cDNA clones of Flk-1 were isolated from another day 8.5 mouse embryo cDNA library, which had been prepared according to the method of Okayama and Berg (1983), and a day 11.5 mouse embryo λgt11 library (Clonetech) using the $^{32}$P-labeled (Feinberg, A. P. and Vogelstein, B. 1983 Anal. Biochem. 132:6–13) 210-bp PCR fragment.

6.1.2. MOUSE EMBRYOS

Balb/c mice were mated overnight and the morning of vaginal plug detection was defined as ½ day of gestation. For Northern blot analysis the frozen embryos were homogenized in 5M guanidinium thiocyanate and RNA was isolated as described (Ullrich, A. et al., 1985, Nature 313:756–761). For in situ hybridization, the embryos were embedded in Tissue-Tek (Miles), frozen on the surface of liquid nitrogen and stored at −70° C. prior to use.

6.1.3. PREPARATION OF PROBES

The 5'-located 2619 bp of the receptor cDNA were subcloned in the pGem3Z vector (Promega) as an EcoR1/BamH1 fragment. The probe for Northern blot hybridization was prepared by labelling the cDNA fragment with $\alpha$-$^{32}$PdATP (Amersham) by random hexanucleotide priming (Boehringer; Feinberg, A. P. and Vogelstein, B., 1983 Anal. Biochem. 132:6–13).

For in situ hybridization a single-strand antisense DNA probe was prepared as described by Schnurch and Risau (Development, 1991 111:1143–54). The plasmid was linearized at the 3' end of the cDNA and a sense transcript was synthesized using SP6 RNA polymerase (Boehringer). The DNA was degraded using DNAase (RNAase free preparation, Boehringer Mannheim). With the transcript, a random-primed cDNA synthesis with a $\alpha$-$^{35}$S dATP (Amersham) was performed by reverse transcription with MMLV reverse transcriptase (BRL). To obtain small cDNA fragments of about 100 bp in average suitable for in situ hybridization, a high excess of primer was used. Subsequently the RNA transcript was partially hydrolyzed in 100 mM NaOH for 20 minutes at 70° C., and the probe was neutralized with the same amount of HC1 and purified with a Sephadex C50 column. After ethanol precipitation the probe was dissolved at a final specific activity of 5×10$^5$ cpm. For control hybridization a sense probe was prepared with the same method.

6.1.4. RNA EXTRACTION AND NORTHERN ANALYSIS

Total cytoplasmic RNA was isolated according to the acidic phenol-method of Chromczynski and Sacchi (1987). Poly(A$^+$) RNA aliquots were electrophoresed in 1.2% agarose formaldehyde (Sambrook, J. et al., 1989 Molecular Cloning: A Laboratory Manual 2nd ed. Cold Spring Harbor Laboratory Press) gels and transferred to nitrocellulose membranes (Schleicher & Schuell), Hybridizations were performed overnight in 50% formamide, 5×SSC (750 mM sodium chloride, 75 mM sodium citrate), 5×Denhardt's (0.1% Ficoll 400, 0.1% polyvinylpyrrolidone, 0.1% BSA) and −0.5% SDS at 42° C. with 1–3×10$^6$ cpm-ml-$^1$ of $^{32}$P-Random primed DNA probe, followed by high stringency washes in 0.2×SSC, 0.5% SDS at 52° C. The filters were exposed for 4 to 8 days.

6.1.5. IN SITU HYBRIDIZATION

Subcloning postfixation and hybridization was essentially performed according to Hogan et al. (1986). 10 μm thick sections were cut at −18° C. on a Leitz cryostat. For prehybridization treatment no incubation with 0.2M HCl for removing the basic proteins was performed. Sections were incubated with the $^{35}$S-cDNA probe (5×10$^4$cpm/μ1) at 52° C. in a buffer containing 50% formamide, 300 mM NaCl, 10 mM Tris-HCl, 10 mM NaPO$_4$ (pH 6.8), 5 mM EDTA, 0.02% Ficoll 400, 0.01% polyvinylpyrrolidone, 0.02% BSA, 10 m /ml yeast RNA, 10% dextran sulfate, and 10 mM NaCl, 10 mM Tris-HCl, 10 mM NaPO$_4$ (pH 6.8), 5 mM EDTA, 10 Mm DTT at 52° C.). For autoradiography, slides were coated with Kodak NTB2 film emulsion and exposed for eight days. After developing, the sections were counterstained and toluidine blue or May-Grinwald.

6.1.6. PREPARATION OF ANTISERA

The 3' primed EcoRV/HindII fragment comprising the 128 C-terminal amino acids of Flk-1 was subcloned in the fusion protein expression vector pGEX3X (Smith, D. B. and Johnson, K. S., 1990 Gene. 67:31–40; Pharmacia). The fusion protein was purified as described and used for immunizing rabbits. After the second boost the rabbits were bled and the antiserum was used for immunoprecipitation.

6.1.7. TRANSIENT EXPRESSION OF Flk-1 IN COS-1 CELLS

Transfection of COS-1 cells was performed essentially as described by Chen and Okayama (1987 Mol. Cell. Biol. 7:2745–2752) and Gorman et al. (1989 Virology 171:377–385). Briefly, cells were seeded to a density of 1.0×10$^6$ per 10-cm dish and incubated overnight in DMEM containing 10% fetal calf serum (Gibco). 20 μg of receptor cDNA cloned into a cytomegalovirus promotor driven expression vector was mixed in 0.5 ml of 0.25M CaCa$_2$, 0.5 ml of 2×BBS (280 mM NaCl, 1.5 mM Na$_2$HPO$_4$, 50 mM BES, pH 6.96 and incubated for 30 min at room temperature. The calcium phosphate/DNA solution was then added to the cells, swirled gently, and incubated for 18 hours at 37° C. under 3% CO$_2$. For ligand binding experiments, the cells were removed from the plate and treated as described below.

To obtain VEGF conditioned media, cells were transfected in 15-cm dishes. Media was collected after 48 h and VEGF was partially purified by affinity chromatography using heparin High Trap TM columns (Pharmacia) and concentrated by ultrafiltration (Ferrara, N. and Henzel, W. J. 1989 Biochem. Biophys. Res. Comm. 161:851–858). The concentration of VEGF was determined by a ligand competition assay with bovine aortic endothelial cells.

For autophosphorylation assays, cells were seeded in 6-well dishes (2×10$^5$ cells per well), transfected as described above, and starved for 24 h in DMEM containing 0.5% fetal calf serum. The cells were then treated with 500 pM VEGF for 10 min. at 37° C. or left untreated and were subsequently lysed as described by Kris et al. (1985). Flk-1 was immunoprecipitated with an antiserum raised in rabbits against the C-terminus of the receptor. The immunoprecipitates were separated on a 7.5% SDS polyacrylamide gel, transferred to nitrocellulose, and incubated with a mouse monoclonal antibody directed against phosphotyrosine (5E2; Fendly, B. M. et al., 1990 Cancer Research 50:1550–1558). Protein bands were visualized using horseradish peroxidase coupled goat anti-mouse antibody and the ECL™ (Amersham) detection system.

6.1.8. RADIOIODINATION OF VEGF

Recombinant human VEGF (5 μg; generously provided by Dr. H. Weich) was dissolved in 110 μl sodium phosphate buffer pH 76, and iodinated by the procedure of Hunter and Greenwood (1962). The reaction products were separated from the labeled protein by passage over a sephadex G50 column, pre-equilibrated with phosphate buffered saline (PBS) containing 0.7% bovine serum albumin (BSA), and aliquots of the collected fractions were counted before and after precipitation with 20% trichloracetic acid. The purity of the iodinated product was estimated to be superior to 90%, as determined by gel electrophoresis, and the specific activity was 77000 cpm/ng. The bioactivity of the iodinated VEGF was confirmed by comparison with the bioactivities of native VEGF using the tissue factor introduction assay described by Clauss, M. et al. (1990 J. Exp. Med. 172:1535–1545).

6.1.9. CROSSLINKING OF VEGF TO Flk-1

COS-1 cells transiently expressing Flk-1 and untransfected COS-1 cells were incubated with 200 pM $^{125}$I-VEGF at 4° C. overnight, then washed twice with PBS and exposed to 0.5 mM disuccinimidyl suberate (DSS) in PBS for 1 h at 4° C. The cells were lysed, Flk-1 immunoprecipitated, and analyzed by electrophoresis on a 7% polyacrylamide gel followed by autoradiography.

6.1.10. VEGF BINDING

Ligand binding experiments were performed as described previously (Schumacher, R. et al., 1991, J. Biol. Chem. 266:19288–19295), COS-1 cells were grown in a 15-cm culture dish in DMEM for 48 h after transfection. Cells were then washed carefully with PBS and incubated with 5 ml of 25 mM EDTA in PBS for 10 min. Cells were then removed from the plate, washed once with binding buffer (DMEM, 25 mM HEPES, pH 7.5, 0.15% gelatin) and resuspended in 5 ml of binding buffer to determine the cell number. In a total volume of 500 μl this cell suspension was incubated for 90 min at 150° C. with 10 pM $^{125}$I-VEGF, and increasing concentration of unlabeled ligand (from 0 to $7\times10^{-9}$), which was partially purified from conditioned media of COS-1 cells transiently expressing VEGF (164 amino acid form; Breier et al., *Development* vol. 114 (2) pp. 521–532 (1992). Leung et al., (*Science* vol. 246 pp. 1306–9 (1989) disclose cDNA clones for bovine and human VEGF). After incubation, cells were washed with PBS 0.1% PBS in the cold. Free ligand was removed by repeated centrifugation and resuspension in binding buffer. Finally, the $^{125}$I radio-activity bound to the cells were determined in a gamma counter (Riastar). Data obtained were analyzed by the method of Munson, P. J. and Rodbard, D. (1980 Anal. Biochem. 107:220–235).

6.1.11. RETROVIRAL VECTORS ENCODING TRANSDOMINANT-NEGATIVE MUTANTS OF Flk-1

Recombinant retroviral vectors were constructed that contained the coding region for amino acids 1 through 806 of the Flk-1 receptor (pLX Flk-1 TM cl.1 and pLX Flk-1 TM cl.3, FIG. 12A). A recombinant virus containing the 541 N-terminal amino acids of the CSF-1 receptor/c-fms (pNTK cfms TM cl.7, FIG. 12B) was used as a control.

pLXSN Flk-1 TM was obtained by ligating the 5'located 2619 bp of the Flk-1 cDNA encoding amino acids 1 to 806 as a ClaI/BamHI fragment to a BglII/HpaI linker, thereby designing a stop-codon 23 amino acids following the transmembrane region (5' GTC ATG GAT CTT CGT TAA 3')(SEQ ID NO:3). In a second step, the ClaI/HpaI fragment was subcloned into the ClaI/HpaI site of the pLXSN vector. Stable GP+E-86 cell lines producing ecotropic retroviruses expressing the wild type and mutated receptor constructs were generated as described by Redemann et al. (*Mol. Cell Biol.* vol 12, p. 491–498 (1992)).

For generation of pNTK c-fms TM, a stop codon was introduced behind amino acids 541 downstream from the transmembrane region of the c-fms cDNA using the oligo-nucleotide 5' TTG TAC AAG TAT AAG TAG TAG CCC AGG TAC CAG 3'(SEQ ID NO:4). The mutated receptor was subcloned in the retroviral expression vector pNTK2 (Stewart et al., EMBO J., 6, 383–388 (1987). Stable GP+E-86 cell lines were obtained as described above.

6.1.12. THE CAPABILITY OF FLK-1 TM TO FORM SIGNALLING-INCOMPETENT HETERODIMERS

The capability of Flk-1 TM to form signalling incompetent heterodimers with the 180 kD wild type Flk-1 was demonstrated by coprecipitation of the truncated 130 kD receptor mutant with an antibody against the C-terminus of the intact receptor from lysates of COS cells transiently expressing both forms. Since the antibody could not recognize Flk-1 TM, coprecipitation was a consequence of heterdimerization.

To test the capability of Flk-1 TM to form signalling incompetent heterodimers with the wild-type Flk-1 in vivo, C6 gliobastoma tumor cells, available from the ATCC, accession number CCL 107, were implanted into nude mice either alone or coimplanted with virus producing cells. Injected cell numbers for the two sets of experiments are indicated below. Beginning at the time when the first tumors appeared, tumor volumes were measured every 2 to 3 days to obtain a growth curve. The results are discussed in Section 6.2.6 and shown in FIGS. 12 and 13.

| Experiment No. 1 | | | |
|---|---|---|---|
| Number of Mice | Number of C6 Cells | Virus-Producer Cell Line | Number of Virus-Cells |
| 4 | $5 \times 10^5$ | pLXSN Flk-1 TM cl.3 | $1 \times 10^7$ |
| 4 | $5 \times 10^5$ | None | 0 |
| 4 | $5 \times 10^5$ | pNTK cfms TM cl.7 | $5 \times 10^6$ |

| Experiment No. 2 | | | |
|---|---|---|---|
| Number of Mice | Number of C6 Cells | Virus-Producer Cell Line | Number of Virus-Cells |
| 4 | $2 \times 10^6$ | pLXSN Flk-1 TM cl.1 | $2 \times 10^7$ |
| 4 | $2 \times 10^6$ | pLXSN Flk-1 TM cl.3 | $2 \times 10^7$ |
| 4 | $2 \times 10^6$ | None | 0 |
| 4 | $2 \times 10^6$ | pNTK cfms TM cl.7 | $2 \times 10^7$ |

In another experiment, the same experimental conditions were performed except that the virus producing cells were injected five days after implantation of 106 tumor cells.

In another experiment, co-implantation of C6 glioblastoma cells was with different relative amounts of retroviral cells producing comparable titers ($1\times10^6$ cfu/ml) of recombinant retrovirus. The effect of the inhibition of tumor growth was dose-dependent, with maximum achieved when the virus-producing cells were in 20-fold excess over the tumor cells. To confirm that the inhibition of the C6 glioblastoma growth was caused by dominant-negative action of the retrovirally expressed constructs on endothelial cells, the tumors were resected and analyzed. Comparison of the whole mount specimens revealed striking differences: whereas the control tumors exhibited a reddish surface, as expected for well-vascularized tissue, the inhibited cell implants were very pale. Histological staining of frozed sections revealed that the control tumors consisted of a homogenous mass of viable cells. Only very few and small necroses could be detected. In contrast, the much smaller, growth-inhibited tumor cell implants had an onion-like histological appearance, which was characterized by different tissue layers: a large, central necrosis was surrounded by a dense layer of viable tumor cells. Invasion of this tumor had not progressed, as evidenced by the presence of natural structures of the skin, such as the muscular cell layer.

The distribution of capillaries and blood vessels in the tissue specimens was determined by incubating frozen tissue sections with a rat monoclonal antibody specific for the endothelial cell adhesion antigen PECAM (De Vries et al.,

*Science* vol. 255, pp. 989–991 (1992)). While the tumors coimplanted with the control virus-producing cells displayed the pattern of capillaries and vessels expected for well-vascularized tissue, the growth-inhibited tumor cell implant exhibited a large central tumor cell necrosis, which was surrounded by a layer of viable tumor cells lacking blood vessels or capillaries. The tumor cells in this layer showed a higher cell density than the control tumor suggesting a significant reduction in tumor-induced edema formation. Since VEGF appears to induce vascular permeability in vivo, and was therefore also designated vascular-permeability factor, inhibition of VEGF/Flk-1 interaction may inhibit tumor associated edema formation.

Flk-1 expression in proliferating endothelial cells of the tumor was confirmed by in situ hybridization of tissue sections with a $^{35}$S-labeled Flk-1 specific antisense cDNA probe and displayed the same distribution as immunostaining with endothelial cell-specific antibodies, indicating that proliferating endothelial cells expressed Flk-1. In situ hybridization with a neomycin resistance gene (neo$^r$) antisense probe confirmed the presence of retroviral sequences. The entire Flk-1 dominant-negative-inhibited tumor consisting of the retrovirus-producing and infected cells was neo$^r$-positive, a result that exactly matched that obtained with a Flk-1 specific probe. The morphology of tumors that had been coimplanted with control virus-producing cell was very similar, but the virus-producing cells were extensively infiltrated by infected tumor cells. In these tumors, which contained many capillaries and blood vessels, neo$^r$-positive signals were also found in endothelial cells.

C6 gliomas exhibit morphological characteristics of human glioblastoma multiforme such as necroses with palisading cells, a high degree of vascularization, and a similar expression pattern of VEGF and its receptors making this model an excellent tool to study anti-angiogenic therapy (Plate et al., Cancer Research vol. 53, pp. 5822–5827 (1993)).

6.1.13. INTRACEREBRAL GRAFTING OF GLIOMA CELLS

To test the capability of Flk-1 TM to form signalling incompetent heterodimers with the wild type Flk-1 in vivo, C6 glioma cells were transplanted intracranially into syngeneic rats with co-injection of a retrovirus-producing cell line.

To transplant glioma cells intracranially into rats, the rats (bodyweight 160–180 g) were anesthetized by i.p. injection of 100 mg/kg Ketamin (Ketaset®) plus 5 mg/kg (Xylazine (Rompun®). The dosage is dependent on the rat strain and should be determined before the experiments. Preanesthesia with isoflurane facilitates i.p. injection and onset of anesthesia. Approximately 3–10 minutes after i.p. injection, animals no longer respond to pain. If analgesia is not complete after 10 minutes, additional dose of 50 mg/kg Ketanest plus 2.5 mg/kg Rompun i.m. (50% of the initial i.p. dose) should be injected. The animals were adjusted in a commercially available small animal stereotactic apparatus. The skin was cleaned with alcohol and a median incision (approximately 1 cm in length) was performed over the skull using a sterile surgical blade. The skin was then slightly disattached from the skull. A burrhole was made using a dental driller on the right side of the hemisphere (coordinates: 2 mm lateral and 1 mm anterior to the bregma). Care was taken not to disrupt the meninges or to damage the brain (check via microscope). A hamilton syringe was placed in the burrhole at the level of the arachnoidea and then slowly lowered until the tip is 3 mm deep in the brain structure (the target point is the cauda-putamen, lateral to the frontal horn of the lateral ventricle). Two to twenty microliters of cells (depending of the amount of cells one wishes to graft) were slowly injected. The maximum volume rats tolerate is 20–25 microliters. If a higher volume is injected, the animal can die immediately due to increased intracranial pressure. After application of the cells, the syringe was not removed immediately in order to allow dissolution of the cells in the brain. After approximately 30 seconds, the syringe was removed slowly. Under these conditions no or very little liquid comes out of the burrhole. The skull was then cleaned and the animals did not bleed at the area operated (check via microscope). The skin was then closed with sutures. Approximately 20–30 minutes was needed for intracerebral grafting of tumor cells in one animal (plus anesthesia).

Animals are monitored for 18–22 days at which time surviving rats are sacrificed, their brains removed (quick frozen or fixed in formalin) and analyzed by standard techniques for measuring tumor volume.

| Experiment No. 1 | | | |
| --- | --- | --- | --- |
| Number of Rats | Number of C6 Cells | Virus-Producer Cell Line | Number of Virus-Cells |
| 8 | $5 \times 10^4$ | Flk-1 TM | $5 \times 10^6$ |
| 8 | $5 \times 10^6$ | 0 | 0 |

All cells were placed intracerebrally in a total volume of $\leq 25$ μl.

The results of this experiment are described in Section 6.2.6 and shown in FIGS. 16A and 16B.

6.1.14. ASSAY FOR AND IDENTIFICATION OF ORGANIC COMPOUNDS THAT MODULATE FLK-1 MEDIATED SIGNAL TRANSDUCTION

Organic compounds that modulate Flk-1 receptor mediated signal transduction can be assayed in a cellular Flk-1 assay wherein modulation of Flk-1 receptor autophosphorylation is measured using an antiphosphotyrosine antibody. In the example shown below, the results are analyzed using a Western blot of electrophoresed cell lysates. Levels of phosphorylation as be measured by other techniques known in the art.

NIH3T3 cells expressing high levels of Flk-1 were seeded in 12-well plates at 250,000 cells/well in DMEM+0.5% calf serum and incubated overnight at 37° C. plus or minus the test substance. Flk-1 tyrosine kinase was stimulated by the addition of 100–500 pM of VEGF/well for 5–10 minutes at 37° C. After stimulation, cells were washed with phosphate buffered saline (PBS) and then lysed with 200 μl of sample buffer (100 mM Tris pH 6.8, 5% glycerol, 1.75% SDS, 1.25 MM EDTA, 0.5 mM sodium vanadate, 2.5 mM sodium pyrophosphate, 1.25% 2-mercaptoethanol). Cell lysates were transferred to centrifuge tubes, boiled at 100° C. for 5 minutes, and then centrifuged at 16,000 G for 5 minutes. Supernatants were removed and stored at −80° C.

For the Western blot assay, forty microliters of saved supernatant per lane were loaded onto a 7.5% SDS-PAGE gel (10 lanes/gel, 1.5 mm thick) and run at 120 V until the dye reached the bottom of the gel. The running buffer used contains 20 mM Tris, 192 mM glycine and 0.1% SDS. Proteins were then transferred to nitrocellulose membrane (Bio-Rad) at 500 mA for 1 hour using ice-cold transblotting buffer containing 50% tank buffer, 20% methanol and 30% water. The nitrocellulose was then blocked with 5% nonfat milk in TBST (50 mM Tris, 150 mM NaCl, and 0.1% triton) for 1 hour or overnight, immunoblotted with a monoclonal antibody against phospho-tyrosine (UBI or Sigma, 1:3000) in TBST for 1 hour, followed by goat anti-mouse (Bio-Rad 1:3000) in TBST-buffer for another 1 hour. Protein bands were detected-by soaking the membrane in ECL chemiluminescence system (Amersham Corp., prepared by mixing equal volumes of reagent 1 and 2) for 1 minute and then exposing the film for about 1–10 minutes.

6.1.15. SYNTHESIS OF A 3-PHENYL-1, 4-DIAZA-ANTHRACENE

A preferred method of synthesis of AG1385 is as follows: 0.47 grams (3 mM) 2,3-diaminonaphthalene and 0.47 grams phenyl gloxal hydrate in 20 ml ethanol were refluxed 1.5 hour. Cooling and filtering gave 0.5 g (65%) of a light brown solid, mp 163° C. NMR CDCl3: δ 9.38 (1H, l.c., H2), 8.71, 8.67 (2H, 2d, H5,10), 8.25, 8.10 (4H, AA'BB'm, H6–9), 7.58 (5H, m, Ph). MS: +256 (M+, 100%), 229 (M—CN, 12%), 126 (71%) m/e.

6.2. RESULTS

6.2.1. ISOLATION OF Flk-1

To identify RTKs that are expressed during mouse development, PCR assays using two degenerate oligonucleotide primer pools that were designed on the basis of highly conserved sequences within the kinase domain of RTKs were performed (Hanks, S. K. et al. 1988, Science 241:42–52). DNA extracted from a λgt10 cDNA library of day 8.5 mouse embryos (Fahrner, K. et al., 1987, EMBO. J., 6:1497–1508), a stage in mouse development at which many differentiation processes begin was used as the template in the PCR assays. In a parallel approach, with the intention of identifying RTKs that regulate angiogenesis, similar primers were used for the amplification of RTK cDNA sequences from capillary endothelial cells that had been isolated from the brains of postnatal day 4–8 mice, a time at which brain endothelial cell proliferation is maximal (Robertson, P. L. et al., 1985, Devel. Brain Res. 23:219–223). Both approaches yielded cDNA sequences (FIG. 11, SEQ. ID NO.:) encoding the recently described fetal liver RTK, Flk-1 (Matthews, W. et al., 1991, Proc. Natl. Acad. Sci. U.S.A. 88:9026–9030). Based on amino acid homology, this receptor is a member of the type III subclass of RTKs (Ullrich, A. and Schlessinger, J. 1990, Cell 61:203–212) and is closely related to human fit, which also contains seven immunoglobin-like repeats in its extracellular domain in contrast to other RTKs of that subfamily, which contain only five such repeat structures (Matthews, W. et al., 1991, Proc. Natl. Acad Sci. U.S.A. 88:9026–9030). Sequence comparisons of Flk-1 with KDR (Terman, B. I. et al., 1991, Oncogene 6:1677–1683) and TKr-C (Sarzani, R. et al., 1992, Biochem. Biophys. Res. Comm. 186:706–714) suggest that these are the human and rat homologues of Flk-1, respectively (FIG. 1).

6.2.2 EXPRESSION OF Flk-1 MRNA DURING EMBRYONIC DEVELOPMENT

As a first step towards the elucidation of the biological function of Flk-1, the expression of Flk-1 mRNA was analyzed in mouse embryos at different development stages. Northern blot hybridization experiments indicated abundant expression of a major 5.5 kb tRNA between day 9.5 and day 18.5, with an apparent decline towards the end of gestation (FIG. 2A). In postnatal day 4–8 brain capillaries Flk-1 mRNA was found to be highly enriched compared to total brain mRNA (FIG. 2B).

In situ hybridization experiments were performed to obtain more detailed information about the expression of Flk-1 during different embryonal stages. A single-stranded antisense, 2619-nucleotide-long DNA probe comprising the Flk-1 extracellular domain was used as a probe because it generated the most specific hybridization signals. As an example, a parasagittal section of a day 14.5 embryo is shown in FIGS. 3A, 3b and 3C. High levels of hybridization were detected in the ventricle of the heart, the lung, and the meninges; other tissues such as brain, liver, and mandible appeared to contain fewer cells expressing Flk-1 mRNA. Thin strands of Flk-1 expression were also observed in the intersegmental regions of the vertebrae and at the inner surface of the atrium and the aorta. Higher magnification revealed that the expression of Flk-1 seemed to be restricted to capillaries and blood vessels. Closer examination of the heart, for example, showed positive signals only in the ventricular capillaries and endothelial lining of the atrium (FIG. 4A). In the lung, Flk-1 expression was detected in peribronchial capillaries, but was absent from bronchial epithelium (FIG. 4D). The aorta showed strong hybridization in endothelial cells, but not in the muscular layer (FIG. 4C).

6.2.3. EXPRESSION OF Flk-1 DURING ORGAN ANGIOGENESIS

The neuroectoderm in the telencephalon of a day 11.5 mouse embryo is largely avascular; the first vascular sprouts begin to radially invade the organ originating from the perineural vascular plexus (Bär, J., 1980, Adv. Anat. Embryol. Cell. Biol. 59:1–62; Risau, W. and Lemmon, V. 1988, Dev. Biol. 125:441–450). At this stage, expression of Flk-1 was high in the perineural vascular plexus and in invading vascular sprouts, as shown in FIG. 5A. These in situ hybridization analyses indicated that the proliferating endothelial cells of an angiogenic sprout expressed the Flk-1 mRNA. At day 14.5, when is the neuroectoderm is already highly vascularized, numerous radial vessels as well as branching vessels of the intraneural plexus contained large amounts of Flk-1 mRNA (FIG. 5B). At postnatal day 4, when sprouting and endothelial cell proliferation is at its highest, strong expression of Flk-1 mRNA was observed in endothelial cells (FIG. 5C). Conversely, in the adult brain when angiogenesis has ceased, Flk-1 expression was very low (FIG. 5D) and appeared to be restricted mainly to the choroid plexus (FIGS. 6A and 6B). In the choroid plexus, cells in the inner vascular layer expressed Flk-1 mRNA, while epithelial cells did not (FIG. 6A, 6B).

The embryonic kidney is vascularized by an angiogenic process (Ekblom, P. et al., 1982, Cell Diff. 11:35–39). Glomerular and peritubular capillaries develop synchronously with epithelial morphogenesis. In the postnatal day 4 kidney, in addition to other capillaries, prominent expression of Flk-1 was observed in the presumptive glomerular capillaries (FIG. 7A). This expression persisted in the adult kidney (FIG. 7C and 7D) and then seemed to be more confined to the glomerular compared to the early postnatal kidney.

6.2.4. Flk-1 EXPRESSION IN ENDOTHELIAL CELL PROGENITORS

To investigate the possible involvement of Flk-1 in the early stages of vascular development, analysis of embryos at different stages during blood island formation were performed. In a sagittal section of the deciduum of a day 8.5 mouse embryo, Flk-1 expression was detected on maternal blood vessels in the deciduum, in the yolk sac and in the trophectoderm. Flk-1 MRNA was also found in the allantois and inside the embryo, mainly located in that part where mesenchyma is found (FIG. 8A). At a higher magnification of the maternal deciduum, high levels of Flk-1 mRNA expression were found in the inner lining of blood vessels, which consist of endothelial cells (FIG. 8B). In the yolk sac, hybridization signals were confined to the mesodermal layer, in which the hemangioblasts differentiate (FIG. 8C). FIG. 8D shows a blood island at higher magnification, in which the peripheral angioblasts expressed a high level of Flk-1 MRNA.

6.2.5. Flk-1 IS A HIGH AFFINITY RECEPTOR FOR VEGF

Detailed examination of in situ hybridization results and comparison with those for VEGF recently reported by Breier, G. et al. (1992, Development 114:521–532) revealed a remarkable similarity in expression pattern. Furthermore, Flk-1 expression in the glomerular endothelium and VEGF in the surrounding epithelial cells (Breier, G. et al., 1992, Development 114:521–532) raised the possibility of a paracrine relationship between these cells types and suggested therefore a ligand-receptor relationship for VEGF and Flk-1, respectively. In order to test this hypothesis, the full-length Flk-1 cDNA was cloned into the mammalian expression vector pCMV, which contains transcriptional control elements of the human cytomegalovirus (Gorman, C. M. et al., 1989, Virology 171:377–385). For transient expression of the receptor, the Flk-1 expressing plasmid was then transfected into COS-1 fibroblasts.

Specific binding of VEGF to the Flk-1 RTK was demonstrated by crosslinking and competition binding experiments. Purified $^{125}$I-labeled VEGF was incubated with COS-1 cells transfected with the pCMV-Flk-1 expression vector crosslinking with DSS and subsequent analysis of immunoprecipitation, PAGE, and autoradiography revealed an approximately 220 kD band which was not detected in the control experiment with untransfected COS-1 cells and is likely to represent the VEGF/Flk-1 receptor complex (FIG. 9A). In addition, VEGF competed with $^{125}$I-VEGF binding to Flk-1 expressing COS-1 cells (FIG. 9B), whereas untransfected COS-1 cells did not bind $^{125}$I-VEGF. The interaction of VEGF with the receptor on transfected cells was specific, as PDGF-BB did not compete with binding of $^{125}$I-VEGF. Analysis of the binding data revealed a Kd of about $10^{-10}$M, suggesting that Flk-1 is a high affinity receptor of VEGF. This finding, together with the Flk-1 and VEGF in situ hybridization results strongly suggests that Flk-1 is a physiologically relevantly receptor for VEGF.

An autophosphorylation assay was performed to confirm the biological relevance of VEGF binding to the Flk-1 receptor. COS1 cells which transiently expressed Flk-1 were starved in DMEM containing 0.5% fetal calf serum for 24 h, stimulated with 0.5 mM VEGF, and lysed. The receptors were immunoprecipitated with the Flk-1 specific polyclonal antibody CT128, and then analyzed by SDS-PAGE and subsequent immunoblotting using the antiphosphotyrosine antibody 5E2 (Fendly, B. M. et al., 1990, Cancer Research 50:1550–1558). A shown in FIG. 10, VEGF stimulation of Flk-1 expressing cells led to a significant induction of tyrosine phosphorylation of the 180 kD Flk-1 receptor.

6.2.6. INHIBITION OF TUMOR GROWTH BY TRANSDOMINANT-NEGATIVE INHIBITION OF Flk-1

The Flk-1 receptor is believed to play a major role in vasculogenesis and angiogenesis. Therefore, inhibition of Flk-1 activity may inhibit vasculogenesis of a developing tumor, for example, and inhibit its growth.

The dominant-negative potential of Flk-1 TM was first examined by measuring its influence on the mitogenic response of Flk-1-expressing NIH 3T3 cells after superinfection with the Flk-1 TM virus. [$^3$H] thymidine incorporation in the 3T3 Flk-1 cell line was maximally stimulated by 500 pM VEGF, with an $EC_{50}$ of about 100 pM. After superinfection with the Flk-1 TM virus, the Flk-1/VEGF-mediated mitogenic response was dramatically suppressed even at a ligand concentration of 5 nM. While 3T3 Flk-1/Flk-1 TM cells expressed wild type Flk-1 levels equal to the parental line, they displayed, due to overexpression of Flk-1 TM, a 6-fold increase of cell surface receptors, as determined by $^{125}$I-VEGF binding. These results were further extended by Flk-1 TM virus-induced suppression of Flk-1 transforming activity and demonstrated not only that mutant and wild type Flk-1 physically associated, but also that this interaction generated signalling-incompetent heterodimers. The dominant-negative inhibitory effect which was achieved at a fivefold excess of Flk-1 TM could not be overcome by a 50 fold ligand excess relative to the $EC_{50}$ value for mitogenic activation. Moreover, Flk-1 TM did not interfere with the signal transduction of the α- and β-PDGF-receptors, demonstrating the specificity of its dominant-negative action.

To test the dominant-negative potential in vivo, tumor cells (C6 rat glioblastoma) and mouse cells producing a recombinant retrovirus encoding a truncated Flk-1 receptor were mixed and implanted subcutaneously into nude mice. The implanted C6 glioblastoma cells secrete VEGF which will bind to and activate the Flk-1 receptors expressed on the surface of mouse endothelial cells. In the absence of any inhibitors of vasculogenesis, the endothelial cells will proliferate and migrate towards the tumor cells. Alternatively, if at the time of injection, the tumor cells are co-injected with cells producing recombinant retrovirus encoding the dominant-negative Flk-1, or if the cells producing recombinant retrovirus are injected after the tumor cells, the endothelial cells growing towards the implanted tumor cells will become infected with recombinant retrovirus which may result in dominant-negative Flk-1 mutant expression and inhibition of endogenous Flk-1 signaling. Suppression of endothelial cell proliferation and migration will result in failure of the implanted tumor cells to become vascularized which will lead to inhibition of tumor growth. As shown in FIGS. 12, 13 and 15 tumor growth is significantly inhibited in mice receiving implantations of cells producing truncated Flk-1 indicating that expression of a truncated Flk-1 receptor can act in a dominant-negative manner to inhibit the activity of endogenous wild-type Flk-1.

As a control, any direct influence of the retroviruses on the growth of the tumor cells can be excluded by growing C6 cells in conditioned media of the different retrovirus-producing cell lines, without any effect on their growth behavior.

To test the role that Flk-1 receptor is believed to play in angiogenesis and vasculogenesis, and to identify potential inhibitors of the Flk-1 receptor, tumor cells (C6 rat glioblastoma) and mouse cells producing a recombinant retrovirus encoding a truncated Flk-1 receptor were mixed and implanted intracranially in rats. The implanted C6 glioblastoma cells secrete VEGF which will bind to and activate the Flk-1 receptors expressed on the surface of rat endothelial cells. Inhibition of Flk-1 receptor signal transduction is measured as inhibition of intracranially tumor growth as seen in rats co-injected with the Flk-1 TM.

Analogous experiments with a variety of other tumor types support the data obtained with the C6 glioblastoma nude mouse subcutaneous model and strongly demonstrate that inhibition of solid tumor growth can be effected by preventing angiogenesis. Angiogenesis a process that is normally regulated by VEGF, which when secreted by tumor cells attracts and stimulated in a paracrine fashion Flk-1-positive vascular endothelial cells.

6.2.7. IDENTIFICATION OF AN ORGANIC COMPOUND THAT INHIBITS FLK-1 RECEPTOR PHOSPHORYLATION

To identify organic compounds that inhibit Flk-1 receptor, organic compounds have been tested in the cellular assay described in Section 6.1.14 for their ability to inhibit Flk-1 receptor phosphorylation. Examples of some of the compounds tested are shown below.

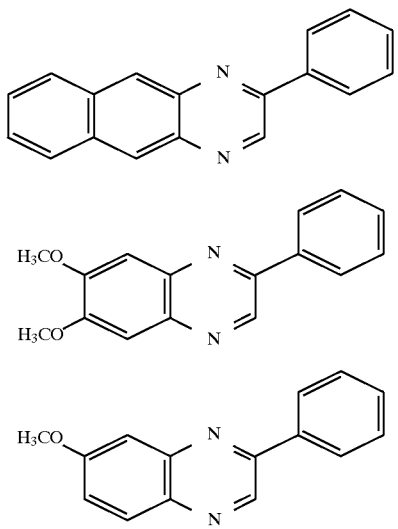

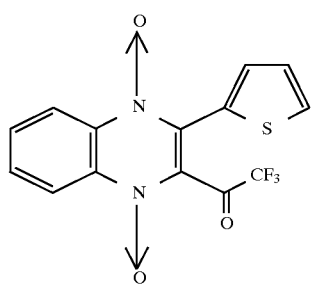

Compound A14 was shown to inhibit Flk-1 receptor phosphorylation almost completely at a test concentration of 100 μM (FIG. 17). Thus this is an example of a compound that could be useful for antagonizing Flk-1 receptor signal transduction and therefore may be useful for inhibiting the Flk-1 receptor mediated mitogenic signal. Accordingly, compound A14 may be therapeutically useful in the treatment of solid tumors by inhibiting angiogenesis.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

It is also to be understood that all base pair sizes given for nucleotides are approximate and are used for purposes of description.

All references cited herein are hereby incorporated by reference in their entirety.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 5470 base pairs
        ( B ) TYPE: nucleic acid
        ( C ) STRANDEDNESS: unknown
        ( D ) TOPOLOGY: unknown ( i i ) MOLECULE TYPE: DNA ( i x ) FEATURE:
        ( A ) NAME/KEY: CDS
        ( B ) LOCATION: 286..4386

( x i ) SEQUENCE DESCRIPTION: SEQ ID NO:1:

```
TATAGGCGA   ATTGGGTACG   GGACCCCCT   CGAGGTCGAC   GGTATCGATA   AGCTTGATAT        60

CGAATTCGGG  CCCAGACTGT   GTCCGCAGC   CGGGATAACC   TGGCTGACCC   GATTCCGCGG       120

ACACCGCTGA  CAGCCGCGGC   TGGAGCCAGG  GCGCCGGTGC   CCCGCGCTCT   CCCCGGTCTT       180
```

-continued

| | | | | | |
|---|---|---|---|---|---|
| GCGCTGCGGG GGCCATACCG CCTCTGTGAC TTCTTTGCGG GCCAGGGACG GAGAAGGAGT | | | | | 240 |
| CTGTGCCTGA GAAACTGGGC TCTGTGCCCA GGCGCGAGGT GCAGG ATG GAG AGC<br>Met Glu Ser<br>1 | | | | | 294 |

```
AAG GCG CTG CTA GCT GTC GCT CTG TGG TTC TGC GTG GAG ACC CGA GCC       342
Lys Ala Leu Leu Ala Val Ala Leu Trp Phe Cys Val Glu Thr Arg Ala
    5               10                  15

GCC TCT GTG GGT TTG ACT GGC GAT TTT CTC CAT CCC CCC AAG CTC AGC       390
Ala Ser Val Gly Leu Thr Gly Asp Phe Leu His Pro Pro Lys Leu Ser
20               25                  30                      35

ACA CAG AAA GAC ATA CTG ACA ATT TTG GCA AAT ACA ACC CTT CAG ATT       438
Thr Gln Lys Asp Ile Leu Thr Ile Leu Ala Asn Thr Thr Leu Gln Ile
                40                  45                  50

ACT TGC AGG GGA CAG CGG GAC CTG GAC TGG CTT TGG CCC AAT GCT CAG       486
Thr Cys Arg Gly Gln Arg Asp Leu Asp Trp Leu Trp Pro Asn Ala Gln
            55                  60                  65

CGT GAT TCT GAG GAA AGG GTA TTG GTG ACT GAA TGC GGC GGT GGT GAC       534
Arg Asp Ser Glu Glu Arg Val Leu Val Thr Glu Cys Gly Gly Gly Asp
        70                  75                  80

AGT ATC TTC TGC AAA ACA CTC ACC ATT CCC AGG GTG GTT GGA AAT GAT       582
Ser Ile Phe Cys Lys Thr Leu Thr Ile Pro Arg Val Val Gly Asn Asp
    85                  90                  95

ACT GGA GCC TAC AAG TGC TCG TAC CGG GAC GTC GAC ATA GCC TCC ACT       630
Thr Gly Ala Tyr Lys Cys Ser Tyr Arg Asp Val Asp Ile Ala Ser Thr
100                 105                 110                     115

GTT TAT GTC TAT GTT CGA GAT TAC AGA TCA CCA TTC ATC GCC TCT GTC       678
Val Tyr Val Tyr Val Arg Asp Tyr Arg Ser Pro Phe Ile Ala Ser Val
                120                 125                 130

AGT GAC CAG CAT GGC ATC GTG TAC ATC ACC GAG AAC AAG AAC AAA ACT       726
Ser Asp Gln His Gly Ile Val Tyr Ile Thr Glu Asn Lys Asn Lys Thr
            135                 140                 145

GTG GTG ATC CCC TGC CGA GGG TCG ATT TCA AAC CTC AAT GTG TCT CTT       774
Val Val Ile Pro Cys Arg Gly Ser Ile Ser Asn Leu Asn Val Ser Leu
        150                 155                 160

TGC GCT AGG TAT CCA GAA AAG AGA TTT GTT CCG GAT GGA AAC AGA ATT       822
Cys Ala Arg Tyr Pro Glu Lys Arg Phe Val Pro Asp Gly Asn Arg Ile
165                 170                 175

TCC TGG GAC AGC GAG ATA GGC TTT ACT CTC CCC AGT TAC ATG ATC AGC       870
Ser Trp Asp Ser Glu Ile Gly Phe Thr Leu Pro Ser Tyr Met Ile Ser
180                 185                 190                     195

TAT GCC GGC ATG GTC TTC TGT GAG GCA AAG ATC AAT GAT GAA ACC TAT       918
Tyr Ala Gly Met Val Phe Cys Glu Ala Lys Ile Asn Asp Glu Thr Tyr
                200                 205                 210

CAG TCT ATC ATG TAC ATA GTT GTG GTT GTA GGA TAT AGG ATT TAT GAT       966
Gln Ser Ile Met Tyr Ile Val Val Val Val Gly Tyr Arg Ile Tyr Asp
            215                 220                 225

GTG ATT CTG AGC CCC CCG CAT GAA ATT GAG CTA TCT GCC GGA GAA AAA      1014
Val Ile Leu Ser Pro Pro His Glu Ile Glu Leu Ser Ala Gly Glu Lys
        230                 235                 240

CTT GTC TTA AAT TGT ACA GCG AGA ACA GAG CTC AAT GTG GGG CTT GAT      1062
Leu Val Leu Asn Cys Thr Ala Arg Thr Glu Leu Asn Val Gly Leu Asp
245                 250                 255

TTC ACC TGG CAC TCT CCA CCT TCA AAG TCT CAT CAT AAG AAG ATT GTA      1110
Phe Thr Trp His Ser Pro Pro Ser Lys Ser His His Lys Lys Ile Val
260                 265                 270                     275

AAC CGG GAT GTG AAA CCC TTT CCT GGG ACT GTG GCG AAG ATG TTT TTG      1158
Asn Arg Asp Val Lys Pro Phe Pro Gly Thr Val Ala Lys Met Phe Leu
                280                 285                 290

AGC ACC TTG ACA ATA GAA AGT GTG ACC AAG AGT GAC CAA GGG GAA TAC      1206
Ser Thr Leu Thr Ile Glu Ser Val Thr Lys Ser Asp Gln Gly Glu Tyr
```

```
                          295                            300                             305
ACC  TGT  GTA  GCG  TCC  AGT  GGA  CGG  ATG  ATC  AAG  AGA  AAT  AGA  ACA  TTT         1254
Thr  Cys  Val  Ala  Ser  Ser  Gly  Arg  Met  Ile  Lys  Arg  Asn  Arg  Thr  Phe
          310                 315                      320

GTC  CGA  GTT  CAC  ACA  AAG  CCT  TTT  ATT  GCT  TTC  GGT  AGT  GGG  ATG  AAA         1302
Val  Arg  Val  His  Thr  Lys  Pro  Phe  Ile  Ala  Phe  Gly  Ser  Gly  Met  Lys
     325                      330                           335

TCT  TTG  GTG  GAA  GCC  ACA  GTG  GGC  AGT  CAA  GTC  CGA  ATC  CCT  GTG  AAG         1350
Ser  Leu  Val  Glu  Ala  Thr  Val  Gly  Ser  Gln  Val  Arg  Ile  Pro  Val  Lys
340                      345                      350                           355

TAT  CTC  AGT  TAC  CCA  GCT  CCT  GAT  ATC  AAA  TGG  TAC  AGA  AAT  GGA  AGG         1398
Tyr  Leu  Ser  Tyr  Pro  Ala  Pro  Asp  Ile  Lys  Trp  Tyr  Arg  Asn  Gly  Arg
                    360                      365                           370

CCC  ATT  GAG  TCC  AAC  TAC  ACA  ATG  ATT  GTT  GGC  GAT  GAA  CTC  ACC  ATC         1446
Pro  Ile  Glu  Ser  Asn  Tyr  Thr  Met  Ile  Val  Gly  Asp  Glu  Leu  Thr  Ile
               375                      380                      385

ATG  GAA  GTG  ACT  GAA  AGA  GAT  GCA  GGA  AAC  TAC  ACG  GTC  ATC  CTC  ACC         1494
Met  Glu  Val  Thr  Glu  Arg  Asp  Ala  Gly  Asn  Tyr  Thr  Val  Ile  Leu  Thr
          390                      395                      400

AAC  CCC  ATT  TCA  ATG  GAG  AAA  CAG  AGC  CAC  ATG  GTC  TCT  CTG  GTT  GTG         1542
Asn  Pro  Ile  Ser  Met  Glu  Lys  Gln  Ser  His  Met  Val  Ser  Leu  Val  Val
405                      410                      415

AAT  GTC  CCA  CCC  CAG  ATC  GGT  GAG  AAA  GCC  TTG  ATC  TCG  CCT  ATG  GAT         1590
Asn  Val  Pro  Pro  Gln  Ile  Gly  Glu  Lys  Ala  Leu  Ile  Ser  Pro  Met  Asp
420                           425                      430                     435

TCC  TAC  CAG  TAT  GGG  ACC  ATG  CAG  ACA  TTG  ACA  TGC  ACA  GTC  TAC  GCC         1638
Ser  Tyr  Gln  Tyr  Gly  Thr  Met  Gln  Thr  Leu  Thr  Cys  Thr  Val  Tyr  Ala
                         440                      445                      450

AAC  CCT  CCC  CTG  CAC  CAC  ATC  CAG  TGG  TAC  TGG  CAG  CTA  GAA  GAA  GCC         1686
Asn  Pro  Pro  Leu  His  His  Ile  Gln  Trp  Tyr  Trp  Gln  Leu  Glu  Glu  Ala
                    455                      460                      465

TGC  TCC  TAC  AGA  CCC  GGC  CAA  ACA  AGC  CCG  TAT  GCT  TGT  AAA  GAA  TGG         1734
Cys  Ser  Tyr  Arg  Pro  Gly  Gln  Thr  Ser  Pro  Tyr  Ala  Cys  Lys  Glu  Trp
               470                      475                      480

AGA  CAC  GTG  GAG  GAT  TTC  CAG  GGG  GGA  AAC  AAG  ATC  GAA  GTC  ACC  AAA         1782
Arg  His  Val  Glu  Asp  Phe  Gln  Gly  Gly  Asn  Lys  Ile  Glu  Val  Thr  Lys
          485                      490                      495

AAC  CAA  TAT  GCC  CTG  ATT  GAA  GGA  AAA  AAC  AAA  ACT  GTA  AGT  ACG  CTG         1830
Asn  Gln  Tyr  Ala  Leu  Ile  Glu  Gly  Lys  Asn  Lys  Thr  Val  Ser  Thr  Leu
500                      505                      510                           515

GTC  ATC  CAA  GCT  GCC  AAC  GTG  TCA  GCG  TTG  TAC  AAA  TGT  GAA  GCC  ATC         1878
Val  Ile  Gln  Ala  Ala  Asn  Val  Ser  Ala  Leu  Tyr  Lys  Cys  Glu  Ala  Ile
                         520                      525                      530

AAC  AAA  GCG  GGA  CGA  GGA  GAG  AGG  GTC  ATC  TCC  TTC  CAT  GTG  ATC  AGG         1926
Asn  Lys  Ala  Gly  Arg  Gly  Glu  Arg  Val  Ile  Ser  Phe  His  Val  Ile  Arg
               535                      540                      545

GGT  CCT  GAA  ATT  ACT  GTG  CAA  CCT  GCT  GCC  CAG  CCA  ACT  GAG  CAG  GAG         1974
Gly  Pro  Glu  Ile  Thr  Val  Gln  Pro  Ala  Ala  Gln  Pro  Thr  Glu  Gln  Glu
          550                      555                      560

AGT  GTG  TCC  CTG  TTG  TGC  ACT  GCA  GAC  AGA  AAT  ACG  TTT  GAG  AAC  CTC         2022
Ser  Val  Ser  Leu  Leu  Cys  Thr  Ala  Asp  Arg  Asn  Thr  Phe  Glu  Asn  Leu
565                      570                      575

ACG  TGG  TAC  AAG  CTT  GGC  TCA  CAG  GCA  ACA  TCG  GTC  CAC  ATG  GGC  GAA         2070
Thr  Trp  Tyr  Lys  Leu  Gly  Ser  Gln  Ala  Thr  Ser  Val  His  Met  Gly  Glu
580                      585                      590                           595

TCA  CTC  ACA  CCA  GTT  TGC  AAG  AAC  TTG  GAT  GCT  CTT  TGG  AAA  CTG  AAT         2118
Ser  Leu  Thr  Pro  Val  Cys  Lys  Asn  Leu  Asp  Ala  Leu  Trp  Lys  Leu  Asn
                    600                      605                      610

GGC  ACC  ATG  TTT  TCT  AAC  AGC  ACA  AAT  GAC  ATC  TTG  ATT  GTG  GCA  TTT         2166
Gly  Thr  Met  Phe  Ser  Asn  Ser  Thr  Asn  Asp  Ile  Leu  Ile  Val  Ala  Phe
```

```
                                615                            620                            625
CAG  AAT  GCC  TCT  CTG  CAG  GAC  CAA  GGC  GAC  TAT  GTT  TGC  TCT  GCT  CAA        2214
Gln  Asn  Ala  Ser  Leu  Gln  Asp  Gln  Gly  Asp  Tyr  Val  Cys  Ser  Ala  Gln
          630                      635                      640

GAT  AAG  AAG  ACC  AAG  AAA  AGA  CAT  TGC  CTG  GTC  AAA  CAG  CTC  ATC  ATC        2262
Asp  Lys  Lys  Thr  Lys  Lys  Arg  His  Cys  Leu  Val  Lys  Gln  Leu  Ile  Ile
     645                      650                      655

CTA  GAG  CGC  ATG  GCA  CCC  ATG  ATC  ACC  GGA  AAT  CTG  GAG  AAT  CAG  ACA        2310
Leu  Glu  Arg  Met  Ala  Pro  Met  Ile  Thr  Gly  Asn  Leu  Glu  Asn  Gln  Thr
660                      665                      670                      675

ACA  ACC  ATT  GGC  GAG  ACC  ATT  GAA  GTG  ACT  TGC  CCA  GCA  TCT  GGA  AAT        2358
Thr  Thr  Ile  Gly  Glu  Thr  Ile  Glu  Val  Thr  Cys  Pro  Ala  Ser  Gly  Asn
                    680                      685                      690

CCT  ACC  CCA  CAC  ATT  ACA  TGG  TTC  AAA  GAC  AAC  GAG  ACC  CTG  GTA  GAA        2406
Pro  Thr  Pro  His  Ile  Thr  Trp  Phe  Lys  Asp  Asn  Glu  Thr  Leu  Val  Glu
               695                      700                      705

GAT  TCA  GGC  ATT  GTA  CTG  AGA  GAT  GGG  AAC  CGG  AAC  CTG  ACT  ATC  CGC        2454
Asp  Ser  Gly  Ile  Val  Leu  Arg  Asp  Gly  Asn  Arg  Asn  Leu  Thr  Ile  Arg
          710                      715                      720

AGG  GTG  AGG  AAG  GAG  GAT  GGA  GGC  CTC  TAC  ACC  TGC  CAG  GCC  TGC  AAT        2502
Arg  Val  Arg  Lys  Glu  Asp  Gly  Gly  Leu  Tyr  Thr  Cys  Gln  Ala  Cys  Asn
     725                      730                      735

GTC  CTT  GGC  TGT  GCA  AGA  GCG  GAG  ACG  CTC  TTC  ATA  ATA  GAA  GGT  GCC        2550
Val  Leu  Gly  Cys  Ala  Arg  Ala  Glu  Thr  Leu  Phe  Ile  Ile  Glu  Gly  Ala
740                      745                      750                      755

CAG  GAA  AAG  ACC  AAC  TTG  GAA  GTC  ATT  ATC  CTC  GTC  GGC  ACT  GCA  GTG        2598
Gln  Glu  Lys  Thr  Asn  Leu  Glu  Val  Ile  Ile  Leu  Val  Gly  Thr  Ala  Val
                    760                      765                      770

ATT  GCC  ATG  TTC  TTC  TGG  CTC  CTT  CTT  GTC  ATT  GTC  CTA  CGG  ACC  GTT        2646
Ile  Ala  Met  Phe  Phe  Trp  Leu  Leu  Leu  Val  Ile  Val  Leu  Arg  Thr  Val
               775                      780                      785

AAG  CGG  GCC  AAT  GAA  GGG  GAA  CTG  AAG  ACA  GGC  TAC  TTG  TCT  ATT  GTC        2694
Lys  Arg  Ala  Asn  Glu  Gly  Glu  Leu  Lys  Thr  Gly  Tyr  Leu  Ser  Ile  Val
          790                      795                      800

ATG  GAT  CCA  GAT  GAA  TTG  CCC  TTG  GAT  GAG  CGC  TGT  GAA  CGC  TTG  CCT        2742
Met  Asp  Pro  Asp  Glu  Leu  Pro  Leu  Asp  Glu  Arg  Cys  Glu  Arg  Leu  Pro
     805                      810                      815

TAT  GAT  GCC  AGC  AAG  TGG  GAA  TTC  CCC  AGG  GAC  CGG  CTG  AAA  CTA  GGA        2790
Tyr  Asp  Ala  Ser  Lys  Trp  Glu  Phe  Pro  Arg  Asp  Arg  Leu  Lys  Leu  Gly
820                      825                      830                      835

AAA  CCT  CTT  GGC  CGC  GGT  GCC  TTC  GGC  CAA  GTG  ATT  GAG  GCA  GAC  GCT        2838
Lys  Pro  Leu  Gly  Arg  Gly  Ala  Phe  Gly  Gln  Val  Ile  Glu  Ala  Asp  Ala
                    840                      845                      850

TTT  GGA  ATT  GAC  AAG  ACA  GCG  ACT  TGC  AAA  ACA  GTA  GCC  GTC  AAG  ATG        2886
Phe  Gly  Ile  Asp  Lys  Thr  Ala  Thr  Cys  Lys  Thr  Val  Ala  Val  Lys  Met
               855                      860                      865

TTG  AAA  GAA  GGA  GCA  ACA  CAC  AGC  GAG  CAT  CGA  GCC  CTC  ATG  TCT  GAA        2934
Leu  Lys  Glu  Gly  Ala  Thr  His  Ser  Glu  His  Arg  Ala  Leu  Met  Ser  Glu
          870                      875                      880

CTC  AAG  ATC  CTC  ATC  CAC  ATT  GGT  CAC  CAT  CTC  AAT  GTG  GTG  AAC  CTC        2982
Leu  Lys  Ile  Leu  Ile  His  Ile  Gly  His  His  Leu  Asn  Val  Val  Asn  Leu
     885                      890                      895

CTA  GGC  GCC  TGC  ACC  AAG  CCG  GGA  GGG  CCT  CTC  ATG  GTG  ATT  GTG  GAA        3030
Leu  Gly  Ala  Cys  Thr  Lys  Pro  Gly  Gly  Pro  Leu  Met  Val  Ile  Val  Glu
900                      905                      910                      915

TTC  TGC  AAG  TTT  GGA  AAC  CTA  TCA  ACT  TAC  TTA  CGG  GGC  AAG  AGA  AAT        3078
Phe  Cys  Lys  Phe  Gly  Asn  Leu  Ser  Thr  Tyr  Leu  Arg  Gly  Lys  Arg  Asn
                    920                      925                      930

GAA  TTT  GTT  CCC  TAT  AAG  AGC  AAA  GGG  GCA  CGC  TTC  CGC  CAG  GGC  AAG        3126
Glu  Phe  Val  Pro  Tyr  Lys  Ser  Lys  Gly  Ala  Arg  Phe  Arg  Gln  Gly  Lys
```

|     |     |     |     |     | 935 |     |     |     |     | 940 |     |     |     |     | 945 |      |
|-----|-----|-----|-----|-----|-----|-----|-----|-----|-----|-----|-----|-----|-----|-----|-----|------|
| GAC | TAC | GTT | GGG | GAG | CTC | TCC | GTG | GAT | CTG | AAA | AGA | CGC | TTG | GAC | AGC | 3174 |
| Asp | Tyr | Val | Gly | Glu | Leu | Ser | Val | Asp | Leu | Lys | Arg | Arg | Leu | Asp | Ser |      |
|     |     |     | 950 |     |     |     | 955 |     |     |     | 960 |     |     |     |     |      |

```
ATC ACC AGC AGC CAG AGC TCT GCC AGC TCA GGC TTT GTT GAG GAG AAA    3222
Ile Thr Ser Ser Gln Ser Ser Ala Ser Ser Gly Phe Val Glu Glu Lys
    965             970             975

TCG CTC AGT GAT GTA GAG GAA GAA GCT TCT GAA GAA CTG TAC AAG        3270
Ser Leu Ser Asp Val Glu Glu Glu Ala Ser Glu Glu Leu Tyr Lys
980             985             990             995

GAC TTC CTG ACC TTG GAG CAT CTC ATC TGT TAC AGC TTC CAA GTG GCT    3318
Asp Phe Leu Thr Leu Glu His Leu Ile Cys Tyr Ser Phe Gln Val Ala
            1000            1005            1010

AAG GGC ATG GAG TTC TTG GCA TCA AGG AAG TGT ATC CAC AGG GAC CTG    3366
Lys Gly Met Glu Phe Leu Ala Ser Arg Lys Cys Ile His Arg Asp Leu
        1015            1020            1025

GCA GCA CGA AAC ATT CTC CTA TCG GAG AAG AAT GTG GTT AAG ATC TGT    3414
Ala Ala Arg Asn Ile Leu Leu Ser Glu Lys Asn Val Val Lys Ile Cys
        1030            1035            1040

GAC TTC GGC TTG GCC CGG GAC ATT TAT AAA GAC CCG GAT TAT GTC AGA    3462
Asp Phe Gly Leu Ala Arg Asp Ile Tyr Lys Asp Pro Asp Tyr Val Arg
1045            1050            1055

AAA GGA GAT GCC CGA CTC CCT TTG AAG TGG ATG GCC CCG GAA ACC ATT    3510
Lys Gly Asp Ala Arg Leu Pro Leu Lys Trp Met Ala Pro Glu Thr Ile
1060            1065            1070            1075

TTT GAC AGA GTA TAC ACA ATT CAG AGC GAT GTG TGG TCT TTC GGT GTG    3558
Phe Asp Arg Val Tyr Thr Ile Gln Ser Asp Val Trp Ser Phe Gly Val
            1080            1085            1090

TTG CTC TGG GAA ATA TTT TCC TTA GGT GCC TCC CCA TAC CCT GGG GTC    3606
Leu Leu Trp Glu Ile Phe Ser Leu Gly Ala Ser Pro Tyr Pro Gly Val
        1095            1100            1105

AAG ATT GAT GAA GAA TTT TGT AGG AGA TTG AAA GAA GGA ACT AGA ATG    3654
Lys Ile Asp Glu Glu Phe Cys Arg Arg Leu Lys Glu Gly Thr Arg Met
        1110            1115            1120

CGG GCT CCT GAC TAC ACT ACC CCA GAA ATG TAC CAG ACC ATG CTG GAC    3702
Arg Ala Pro Asp Tyr Thr Thr Pro Glu Met Tyr Gln Thr Met Leu Asp
        1125            1130            1135

TGC TGG CAT GAG GAC CCC AAC CAG AGA CCC TCG TTT TCA GAG TTG GTG    3750
Cys Trp His Glu Asp Pro Asn Gln Arg Pro Ser Phe Ser Glu Leu Val
1140            1145            1150            1155

GAG CAT TTG GGA AAC CTC CTG CAA GCA AAT GCG CAG CAG GAT GGC AAA    3798
Glu His Leu Gly Asn Leu Leu Gln Ala Asn Ala Gln Gln Asp Gly Lys
            1160            1165            1170

GAC TAT ATT GTT CTT CCA ATG TCA GAG ACA CTG AGC ATG GAA GAG GAT    3846
Asp Tyr Ile Val Leu Pro Met Ser Glu Thr Leu Ser Met Glu Glu Asp
        1175            1180            1185

TCT GGA CTC TCC CTG CCT ACC TCA CCT GTT TCC TGT ATG GAG GAA GAG    3894
Ser Gly Leu Ser Leu Pro Thr Ser Pro Val Ser Cys Met Glu Glu Glu
        1190            1195            1200

GAA GTG TGC GAC CCC AAA TTC CAT TAT GAC AAC ACA GCA GGA ATC AGT    3942
Glu Val Cys Asp Pro Lys Phe His Tyr Asp Asn Thr Ala Gly Ile Ser
    1205            1210            1215

CAT TAT CTC CAG AAC AGT AAG CGA AAG AGC CGG CCA GTG AGT GTA AAA    3990
His Tyr Leu Gln Asn Ser Lys Arg Lys Ser Arg Pro Val Ser Val Lys
1220            1225            1230            1235

ACA TTT GAA GAT ATC CCA TTG GAG GAA CCA GAA GTA AAA GTG ATC CCA    4038
Thr Phe Glu Asp Ile Pro Leu Glu Glu Pro Glu Val Lys Val Ile Pro
            1240            1245            1250

GAT GAC AGC CAG ACA GAC AGT GGG ATG GTC CTT GCA TCA GAA GAG CTG    4086
Asp Asp Ser Gln Thr Asp Ser Gly Met Val Leu Ala Ser Glu Glu Leu
```

|  |  |  |  |  | 1255 |  |  |  |  | 1260 |  |  |  |  | 1265 |  |  |
|---|---|---|---|---|---|---|---|---|---|---|---|---|---|---|---|---|---|
| AAA | ACT | CTG | GAA | GAC | AGG | AAC | AAA | TTA | TCT | CCA | TCT | TTT | GGT | GGA | ATG | | 4134 |
| Lys | Thr | Leu | Glu | Asp | Arg | Asn | Lys | Leu | Ser | Pro | Ser | Phe | Gly | Gly | Met | | |
| | | | 1270 | | | | 1275 | | | | | 1280 | | | | | |
| ATG | CCC | AGT | AAA | AGC | AGG | GAG | TCT | GTG | GCC | TCG | GAA | GGC | TCC | AAC | CAG | | 4182 |
| Met | Pro | Ser | Lys | Ser | Arg | Glu | Ser | Val | Ala | Ser | Glu | Gly | Ser | Asn | Gln | | |
| | | 1285 | | | | 1290 | | | | | 1295 | | | | | | |
| ACC | AGT | GGC | TAC | CAG | TCT | GGG | TAT | CAC | TCA | GAT | GAC | ACA | GAC | ACC | ACC | | 4230 |
| Thr | Ser | Gly | Tyr | Gln | Ser | Gly | Tyr | His | Ser | Asp | Asp | Thr | Asp | Thr | Thr | | |
| 1300 | | | | | 1305 | | | | | 1310 | | | | | | 1315 | |
| GTG | TAC | TCC | AGC | GAC | GAG | GCA | GGA | CTT | TTA | AAG | ATG | GTG | GAT | GCT | GCA | | 4278 |
| Val | Tyr | Ser | Ser | Asp | Glu | Ala | Gly | Leu | Leu | Lys | Met | Val | Asp | Ala | Ala | | |
| | | | | 1320 | | | | | 1325 | | | | | 1330 | | | |
| GTT | CAC | GCT | GAC | TCA | GGG | ACC | ACA | CTG | CAG | CTC | ACC | TCC | TGT | TTA | AAT | | 4326 |
| Val | His | Ala | Asp | Ser | Gly | Thr | Thr | Leu | Gln | Leu | Thr | Ser | Cys | Leu | Asn | | |
| | | | | 1335 | | | | | 1340 | | | | | 1345 | | | |
| GGA | AGT | GGT | CCT | GTC | CCG | GCT | CCG | CCC | CCA | ACT | CCT | GGA | AAT | CAC | GAG | | 4374 |
| Gly | Ser | Gly | Pro | Val | Pro | Ala | Pro | Pro | Pro | Thr | Pro | Gly | Asn | His | Glu | | |
| | | | 1350 | | | | | 1355 | | | | | 1360 | | | | |
| AGA | GGT | GCT | GCT | TAGATTTTCA | | AGTGTTGTTC | | TTTCCACCAC | | CCGGAAGTAG | | | | | | | 4426 |
| Arg | Gly | Ala | Ala | | | | | | | | | | | | | | |
| | | 1365 | | | | | | | | | | | | | | | |

| CCACATTTGA | TTTTCATTTT | TGGAGGAGGG | ACCTCAGACT | GCAAGGAGCT | TGTCCTCAGG | 4486 |
|---|---|---|---|---|---|---|
| GCATTTCCAG | AGAAGATGCC | CATGACCCAA | GAATGTGTTG | ACTCTACTCT | CTTTTCCATT | 4546 |
| CATTTAAAAG | TCCTATATAA | TGTGCCCTGC | TGTGGTCTCA | CTACCAGTTA | AAGCAAAAGA | 4606 |
| CTTTCAAACA | CGTGGACTCT | GTCCTCCAAG | AAGTGGCAAC | GGCACCTCTG | TGAAACTGGA | 4666 |
| TCGAATGGGC | AATGCTTTGT | GTGTTGAGGA | TGGGTGAGAT | GTCCCAGGGC | CGAGTCTGTC | 4726 |
| TACCTTGGAG | GCTTTGTGGA | GGATGCGGGC | TATGAGCCAA | GTGTTAAGTG | TGGGATGTGG | 4786 |
| ACTGGGAGGA | AGGAAGGCGC | AAGTCGCTCG | GAGAGCGGTT | GGAGCCTGCA | GATGCATTGT | 4846 |
| GCTGGCTCTG | GTGGAGGTGG | GCTTGTGGCC | TGTCAGGAAA | CGCAAAGGCG | GCCGGCAGGG | 4906 |
| TTTGGTTTTG | GAAGGTTTGC | GTGCTCTTCA | CAGTCGGGTT | ACAGGCAGT | TCCCTGTGGC | 4966 |
| GTTTCCTACT | CCTAATGAGA | GTTCCTTCCG | GACTCTTACG | TGTCTCCTGG | CCTGGCCCCA | 5026 |
| GGAAGGAAAT | GATGCAGCTT | GCTCCTTCCT | CATCTCTCAG | GCTGTGCCTT | AATTCAGAAC | 5086 |
| ACCAAAAGAG | AGGAACGTCG | GCAGAGGCTC | CTGACGGGGC | CGAAGAATTG | TGAGAACAGA | 5146 |
| ACAGAAACTC | AGGGTTTCTG | CTGGGTGGAG | ACCCACGTGG | CGCCCTGGTG | GCAGGTCTGA | 5206 |
| GGGTTCTCTG | TCAAGTGGCG | GTAAAGGCTC | AGGCTGGTGT | TCTTCCTCTA | TCTCCACTCC | 5266 |
| TGTCAGGCCC | CCAAGTCCTC | AGTATTTTAG | CTTTGTGGCT | TCCTGATGGC | AGAAAAATCT | 5326 |
| TAATTGGTTG | GTTTGCTCTC | CAGATAATCA | CTAGCCAGAT | TTCGAATTA | CTTTTTAGCC | 5386 |
| GAGGTTATGA | TAACATCTAC | TGTATCCTTT | AGAATTTTAA | CCTATAAAAC | TATGTCTACT | 5446 |
| GGTTTCTGCC | TGTGTGCTTA | TGTT | | | | 5470 |

( 2 ) INFORMATION FOR SEQ ID NO:2:

( i ) SEQUENCE CHARACTERISTICS:
        ( A ) LENGTH: 1367 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Glu | Ser | Lys | Ala | Leu | Leu | Ala | Val | Ala | Leu | Trp | Phe | Cys | Val | Glu |
|---|---|---|---|---|---|---|---|---|---|---|---|---|---|---|---|
| 1 | | | | 5 | | | | | 10 | | | | | 15 | |

```
Thr  Arg  Ala  Ala  Ser  Val  Gly  Leu  Thr  Gly  Asp  Phe  Leu  His  Pro  Pro
               20                  25                       30

Lys  Leu  Ser  Thr  Gln  Lys  Asp  Ile  Leu  Thr  Ile  Leu  Ala  Asn  Thr  Thr
          35                      40                       45

Leu  Gln  Ile  Thr  Cys  Arg  Gly  Gln  Arg  Asp  Leu  Asp  Trp  Leu  Trp  Pro
     50                       55                      60

Asn  Ala  Gln  Arg  Asp  Ser  Glu  Glu  Arg  Val  Leu  Val  Thr  Glu  Cys  Gly
65                       70                      75                           80

Gly  Gly  Asp  Ser  Ile  Phe  Cys  Lys  Thr  Leu  Thr  Ile  Pro  Arg  Val  Val
               85                       90                            95

Gly  Asn  Asp  Thr  Gly  Ala  Tyr  Lys  Cys  Ser  Tyr  Arg  Asp  Val  Asp  Ile
               100                      105                      110

Ala  Ser  Thr  Val  Tyr  Val  Tyr  Val  Arg  Asp  Tyr  Arg  Ser  Pro  Phe  Ile
          115                      120                      125

Ala  Ser  Val  Ser  Asp  Gln  His  Gly  Ile  Val  Tyr  Ile  Thr  Glu  Asn  Lys
     130                      135                      140

Asn  Lys  Thr  Val  Val  Ile  Pro  Cys  Arg  Gly  Ser  Ile  Ser  Asn  Leu  Asn
145                      150                      155                      160

Val  Ser  Leu  Cys  Ala  Arg  Tyr  Pro  Glu  Lys  Arg  Phe  Val  Pro  Asp  Gly
               165                      170                           175

Asn  Arg  Ile  Ser  Trp  Asp  Ser  Glu  Ile  Gly  Phe  Thr  Leu  Pro  Ser  Tyr
               180                      185                      190

Met  Ile  Ser  Tyr  Ala  Gly  Met  Val  Phe  Cys  Glu  Ala  Lys  Ile  Asn  Asp
          195                      200                      205

Glu  Thr  Tyr  Gln  Ser  Ile  Met  Tyr  Ile  Val  Val  Val  Val  Gly  Tyr  Arg
     210                      215                      220

Ile  Tyr  Asp  Val  Ile  Leu  Ser  Pro  Pro  His  Glu  Ile  Glu  Leu  Ser  Ala
225                      230                      235                      240

Gly  Glu  Lys  Leu  Val  Leu  Asn  Cys  Thr  Ala  Arg  Thr  Glu  Leu  Asn  Val
               245                      250                      255

Gly  Leu  Asp  Phe  Thr  Trp  His  Ser  Pro  Pro  Ser  Lys  Ser  His  His  Lys
               260                      265                      270

Lys  Ile  Val  Asn  Arg  Asp  Val  Lys  Pro  Phe  Pro  Gly  Thr  Val  Ala  Lys
          275                      280                      285

Met  Phe  Leu  Ser  Thr  Leu  Thr  Ile  Glu  Ser  Val  Thr  Lys  Ser  Asp  Gln
     290                      295                      300

Gly  Glu  Tyr  Thr  Cys  Val  Ala  Ser  Ser  Gly  Arg  Met  Ile  Lys  Arg  Asn
305                      310                      315                      320

Arg  Thr  Phe  Val  Arg  Val  His  Thr  Lys  Pro  Phe  Ile  Ala  Phe  Gly  Ser
               325                      330                      335

Gly  Met  Lys  Ser  Leu  Val  Glu  Ala  Thr  Val  Gly  Ser  Gln  Val  Arg  Ile
               340                      345                      350

Pro  Val  Lys  Tyr  Leu  Ser  Tyr  Pro  Ala  Pro  Asp  Ile  Lys  Trp  Tyr  Arg
          355                      360                      365

Asn  Gly  Arg  Pro  Ile  Glu  Ser  Asn  Tyr  Thr  Met  Ile  Val  Gly  Asp  Glu
     370                      375                      380

Leu  Thr  Ile  Met  Glu  Val  Thr  Glu  Arg  Asp  Ala  Gly  Asn  Tyr  Thr  Val
385                      390                      395                      400

Ile  Leu  Thr  Asn  Pro  Ile  Ser  Met  Glu  Lys  Gln  Ser  His  Met  Val  Ser
               405                      410                      415

Leu  Val  Val  Asn  Val  Pro  Pro  Gln  Ile  Gly  Glu  Lys  Ala  Leu  Ile  Ser
               420                      425                      430

Pro  Met  Asp  Ser  Tyr  Gln  Tyr  Gly  Thr  Met  Gln  Thr  Leu  Thr  Cys  Thr
```

-continued

|     |     |     |     |     | 435 |     |     |     |     | 440 |     |     |     |     | 445 |
| --- | --- | --- | --- | --- | --- | --- | --- | --- | --- | --- | --- | --- | --- | --- | --- |
| Val | Tyr | Ala | Asn | Pro | Pro | Leu | His | His | Ile | Gln | Trp | Tyr | Trp | Gln | Leu |
|     | 450 |     |     |     |     | 455 |     |     |     |     | 460 |     |     |     |     |
| Glu | Glu | Ala | Cys | Ser | Tyr | Arg | Pro | Gly | Gln | Thr | Ser | Pro | Tyr | Ala | Cys |
| 465 |     |     |     |     | 470 |     |     |     |     | 475 |     |     |     |     | 480 |
| Lys | Glu | Trp | Arg | His | Val | Glu | Asp | Phe | Gln | Gly | Gly | Asn | Lys | Ile | Glu |
|     |     |     |     | 485 |     |     |     |     | 490 |     |     |     |     | 495 |     |
| Val | Thr | Lys | Asn | Gln | Tyr | Ala | Leu | Ile | Glu | Gly | Lys | Asn | Lys | Thr | Val |
|     |     |     | 500 |     |     |     |     | 505 |     |     |     |     | 510 |     |     |
| Ser | Thr | Leu | Val | Ile | Gln | Ala | Ala | Asn | Val | Ser | Ala | Leu | Tyr | Lys | Cys |
|     |     | 515 |     |     |     |     | 520 |     |     |     |     | 525 |     |     |     |
| Glu | Ala | Ile | Asn | Lys | Ala | Gly | Arg | Gly | Glu | Arg | Val | Ile | Ser | Phe | His |
|     | 530 |     |     |     |     | 535 |     |     |     |     | 540 |     |     |     |     |
| Val | Ile | Arg | Gly | Pro | Glu | Ile | Thr | Val | Gln | Pro | Ala | Ala | Gln | Pro | Thr |
| 545 |     |     |     |     | 550 |     |     |     |     | 555 |     |     |     |     | 560 |
| Glu | Gln | Glu | Ser | Val | Ser | Leu | Leu | Cys | Thr | Ala | Asp | Arg | Asn | Thr | Phe |
|     |     |     |     | 565 |     |     |     |     | 570 |     |     |     |     | 575 |     |
| Glu | Asn | Leu | Thr | Trp | Tyr | Lys | Leu | Gly | Ser | Gln | Ala | Thr | Ser | Val | His |
|     |     |     | 580 |     |     |     |     | 585 |     |     |     |     | 590 |     |     |
| Met | Gly | Glu | Ser | Leu | Thr | Pro | Val | Cys | Lys | Asn | Leu | Asp | Ala | Leu | Trp |
|     |     | 595 |     |     |     |     | 600 |     |     |     |     | 605 |     |     |     |
| Lys | Leu | Asn | Gly | Thr | Met | Phe | Ser | Asn | Ser | Thr | Asn | Asp | Ile | Leu | Ile |
| 610 |     |     |     |     | 615 |     |     |     |     | 620 |     |     |     |     |     |
| Val | Ala | Phe | Gln | Asn | Ala | Ser | Leu | Gln | Asp | Gln | Gly | Asp | Tyr | Val | Cys |
| 625 |     |     |     |     | 630 |     |     |     |     | 635 |     |     |     |     | 640 |
| Ser | Ala | Gln | Asp | Lys | Lys | Thr | Lys | Lys | Arg | His | Cys | Leu | Val | Lys | Gln |
|     |     |     |     | 645 |     |     |     |     | 650 |     |     |     |     | 655 |     |
| Leu | Ile | Ile | Leu | Glu | Arg | Met | Ala | Pro | Met | Ile | Thr | Gly | Asn | Leu | Glu |
|     |     |     | 660 |     |     |     |     | 665 |     |     |     |     | 670 |     |     |
| Asn | Gln | Thr | Thr | Thr | Ile | Gly | Glu | Thr | Ile | Glu | Val | Thr | Cys | Pro | Ala |
|     |     | 675 |     |     |     |     | 680 |     |     |     |     | 685 |     |     |     |
| Ser | Gly | Asn | Pro | Thr | Pro | His | Ile | Thr | Trp | Phe | Lys | Asp | Asn | Glu | Thr |
|     | 690 |     |     |     |     | 695 |     |     |     |     | 700 |     |     |     |     |
| Leu | Val | Glu | Asp | Ser | Gly | Ile | Val | Leu | Arg | Asp | Gly | Asn | Arg | Asn | Leu |
| 705 |     |     |     |     | 710 |     |     |     |     | 715 |     |     |     |     | 720 |
| Thr | Ile | Arg | Arg | Val | Arg | Lys | Glu | Asp | Gly | Gly | Leu | Tyr | Thr | Cys | Gln |
|     |     |     |     | 725 |     |     |     |     | 730 |     |     |     |     | 735 |     |
| Ala | Cys | Asn | Val | Leu | Gly | Cys | Ala | Arg | Ala | Glu | Thr | Leu | Phe | Ile | Ile |
|     |     |     | 740 |     |     |     |     | 745 |     |     |     |     | 750 |     |     |
| Glu | Gly | Ala | Gln | Glu | Lys | Thr | Asn | Leu | Glu | Val | Ile | Ile | Leu | Val | Gly |
|     |     | 755 |     |     |     |     | 760 |     |     |     |     | 765 |     |     |     |
| Thr | Ala | Val | Ile | Ala | Met | Phe | Phe | Trp | Leu | Leu | Leu | Val | Ile | Val | Leu |
|     | 770 |     |     |     |     | 775 |     |     |     |     | 780 |     |     |     |     |
| Arg | Thr | Val | Lys | Arg | Ala | Asn | Glu | Gly | Glu | Leu | Lys | Thr | Gly | Tyr | Leu |
| 785 |     |     |     |     | 790 |     |     |     |     | 795 |     |     |     |     | 800 |
| Ser | Ile | Val | Met | Asp | Pro | Asp | Glu | Leu | Pro | Leu | Asp | Glu | Arg | Cys | Glu |
|     |     |     |     | 805 |     |     |     |     | 810 |     |     |     |     | 815 |     |
| Arg | Leu | Pro | Tyr | Asp | Ala | Ser | Lys | Trp | Glu | Phe | Pro | Arg | Asp | Arg | Leu |
|     |     |     | 820 |     |     |     |     | 825 |     |     |     |     | 830 |     |     |
| Lys | Leu | Gly | Lys | Pro | Leu | Gly | Arg | Gly | Ala | Phe | Gly | Gln | Val | Ile | Glu |
|     |     | 835 |     |     |     |     | 840 |     |     |     |     | 845 |     |     |     |
| Ala | Asp | Ala | Phe | Gly | Ile | Asp | Lys | Thr | Ala | Thr | Cys | Lys | Thr | Val | Ala |
|     | 850 |     |     |     |     | 855 |     |     |     |     | 860 |     |     |     |     |

```
Val  Lys  Met  Leu  Lys  Glu  Gly  Ala  Thr  His  Ser  Glu  His  Arg  Ala  Leu
865            870                 875                      880

Met  Ser  Glu  Leu  Lys  Ile  Leu  Ile  His  Ile  Gly  His  His  Leu  Asn  Val
               885                 890                           895

Val  Asn  Leu  Leu  Gly  Ala  Cys  Thr  Lys  Pro  Gly  Gly  Pro  Leu  Met  Val
          900                      905                           910

Ile  Val  Glu  Phe  Cys  Lys  Phe  Gly  Asn  Leu  Ser  Thr  Tyr  Leu  Arg  Gly
          915                      920                           925

Lys  Arg  Asn  Glu  Phe  Val  Pro  Tyr  Lys  Ser  Lys  Gly  Ala  Arg  Phe  Arg
930                      935                      940

Gln  Gly  Lys  Asp  Tyr  Val  Gly  Glu  Leu  Ser  Val  Asp  Leu  Lys  Arg  Arg
945                 950                      955                           960

Leu  Asp  Ser  Ile  Thr  Ser  Ser  Gln  Ser  Ser  Ala  Ser  Ser  Gly  Phe  Val
               965                 970                           975

Glu  Glu  Lys  Ser  Leu  Ser  Asp  Val  Glu  Glu  Glu  Ala  Ser  Glu  Glu
               980                 985                           990

Leu  Tyr  Lys  Asp  Phe  Leu  Thr  Leu  Glu  His  Leu  Ile  Cys  Tyr  Ser  Phe
          995                      1000                          1005

Gln  Val  Ala  Lys  Gly  Met  Glu  Phe  Leu  Ala  Ser  Arg  Lys  Cys  Ile  His
     1010                     1015                     1020

Arg  Asp  Leu  Ala  Ala  Arg  Asn  Ile  Leu  Leu  Ser  Glu  Lys  Asn  Val  Val
1025                     1030                     1035                     1040

Lys  Ile  Cys  Asp  Phe  Gly  Leu  Ala  Arg  Asp  Ile  Tyr  Lys  Asp  Pro  Asp
               1045                      1050                     1055

Tyr  Val  Arg  Lys  Gly  Asp  Ala  Arg  Leu  Pro  Leu  Lys  Trp  Met  Ala  Pro
               1060                      1065                     1070

Glu  Thr  Ile  Phe  Asp  Arg  Val  Tyr  Thr  Ile  Gln  Ser  Asp  Val  Trp  Ser
          1075                      1080                          1085

Phe  Gly  Val  Leu  Leu  Trp  Glu  Ile  Phe  Ser  Leu  Gly  Ala  Ser  Pro  Tyr
     1090                     1095                     1100

Pro  Gly  Val  Lys  Ile  Asp  Glu  Glu  Phe  Cys  Arg  Arg  Leu  Lys  Glu  Gly
1105                     1110                     1115                     1120

Thr  Arg  Met  Arg  Ala  Pro  Asp  Tyr  Thr  Thr  Pro  Glu  Met  Tyr  Gln  Thr
               1125                      1130                     1135

Met  Leu  Asp  Cys  Trp  His  Glu  Asp  Pro  Asn  Gln  Arg  Pro  Ser  Phe  Ser
               1140                      1145                     1150

Glu  Leu  Val  Glu  His  Leu  Gly  Asn  Leu  Leu  Gln  Ala  Asn  Ala  Gln  Gln
                    1155                     1160                1165

Asp  Gly  Lys  Asp  Tyr  Ile  Val  Leu  Pro  Met  Ser  Glu  Thr  Leu  Ser  Met
          1170                     1175                     1180

Glu  Glu  Asp  Ser  Gly  Leu  Ser  Leu  Pro  Thr  Ser  Pro  Val  Ser  Cys  Met
1185                     1190                     1195                     1200

Glu  Glu  Glu  Glu  Val  Cys  Asp  Pro  Lys  Phe  His  Tyr  Asp  Asn  Thr  Ala
               1205                     1210                     1215

Gly  Ile  Ser  His  Tyr  Leu  Gln  Asn  Ser  Lys  Arg  Lys  Ser  Arg  Pro  Val
          1220                     1225                     1230

Ser  Val  Lys  Thr  Phe  Glu  Asp  Ile  Pro  Leu  Glu  Glu  Pro  Glu  Val  Lys
               1235                     1240                     1245

Val  Ile  Pro  Asp  Asp  Ser  Gln  Thr  Asp  Ser  Gly  Met  Val  Leu  Ala  Ser
     1250                     1255                     1260

Glu  Glu  Leu  Lys  Thr  Leu  Glu  Asp  Arg  Asn  Lys  Leu  Ser  Pro  Ser  Phe
1265                     1270                     1275                     1280

Gly  Gly  Met  Met  Pro  Ser  Lys  Ser  Arg  Glu  Ser  Val  Ala  Ser  Glu  Gly
               1285                     1290                     1295
```

-continued

| Ser | Asn | Gln | Thr | Ser | Gly | Tyr | Gln | Ser | Gly | Tyr | His | Ser | Asp | Asp | Thr |
|||| 1300 |||| 1305 |||| 1310 |||

| Asp | Thr | Thr | Val | Tyr | Ser | Ser | Asp | Glu | Ala | Gly | Leu | Leu | Lys | Met | Val |
|||| 1315 |||| 1320 |||| 1325 |||

| Asp | Ala | Ala | Val | His | Ala | Asp | Ser | Gly | Thr | Thr | Leu | Gln | Leu | Thr | Ser |
|||| 1330 |||| 1335 |||| 1340 |||

| Cys | Leu | Asn | Gly | Ser | Gly | Pro | Val | Pro | Ala | Pro | Pro | Pro | Thr | Pro | Gly |
| 1345 |||| 1350 |||| 1355 |||| 1360 |

| Asn | His | Glu | Arg | Gly | Ala | Ala |
||||| 1365 |||

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:3:

GTCATGGATC TTCGTTAA                                        18

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:4:

TTGTACAAGT ATAAGTAGTA GCCCAGGTAC CAG                  33

( 2 ) INFORMATION FOR SEQ ID NO:5:

( i ) SEQUENCE CHARACTERISTICS:
        ( A ) LENGTH: 806 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

| Met | Glu | Ser | Lys | Ala | Leu | Leu | Ala | Val | Ala | Leu | Trp | Phe | Cys | Val | Glu |
| 1 |||| 5 |||| 10 |||| 15 ||

| Thr | Arg | Ala | Ala | Ser | Val | Gly | Leu | Thr | Gly | Asp | Phe | Leu | His | Pro | Pro |
|||| 20 |||| 25 |||| 30 |||

| Lys | Leu | Ser | Thr | Gln | Lys | Asp | Ile | Leu | Thr | Ile | Leu | Ala | Asn | Thr | Thr |
|||| 35 |||| 40 |||| 45 |||

| Leu | Gln | Ile | Thr | Cys | Arg | Gly | Gln | Arg | Asp | Leu | Asp | Trp | Leu | Trp | Pro |
|||| 50 |||| 55 |||| 60 |||

| Asn | Ala | Gln | Arg | Asp | Ser | Glu | Glu | Arg | Val | Leu | Val | Thr | Glu | Cys | Gly |
| 65 |||| 70 |||| 75 |||| 80 |

| Gly | Gly | Asp | Ser | Ile | Phe | Cys | Lys | Thr | Leu | Thr | Ile | Pro | Arg | Val | Val |
|||| 85 |||| 90 |||| 95 |||

| Gly | Asn | Asp | Thr | Gly | Ala | Tyr | Lys | Cys | Ser | Tyr | Arg | Asp | Val | Asp | Ile |
|||| 100 |||| 105 |||| 110 |||

-continued

```
Ala  Ser  Thr  Val  Tyr  Val  Tyr  Val  Arg  Asp  Tyr  Arg  Ser  Pro  Phe  Ile
          115                 120                 125

Ala  Ser  Val  Ser  Asp  Gln  His  Gly  Ile  Val  Tyr  Ile  Thr  Glu  Asn  Lys
130                      135                      140

Asn  Lys  Thr  Val  Val  Ile  Pro  Cys  Arg  Gly  Ser  Ile  Ser  Asn  Leu  Asn
145                      150                      155                      160

Val  Ser  Leu  Cys  Ala  Arg  Tyr  Pro  Glu  Lys  Arg  Phe  Val  Pro  Asp  Gly
               165                 170                      175

Asn  Arg  Ile  Ser  Trp  Asp  Ser  Glu  Ile  Gly  Phe  Thr  Leu  Pro  Ser  Tyr
               180                 185                      190

Met  Ile  Ser  Tyr  Ala  Gly  Met  Val  Phe  Cys  Glu  Ala  Lys  Ile  Asn  Asp
          195                 200                 205

Glu  Thr  Tyr  Gln  Ser  Ile  Met  Tyr  Ile  Val  Val  Val  Gly  Tyr  Arg
     210                 215                      220

Ile  Tyr  Asp  Val  Ile  Leu  Ser  Pro  Pro  His  Glu  Ile  Glu  Leu  Ser  Ala
225                      230                 235                      240

Gly  Glu  Lys  Leu  Val  Leu  Asn  Cys  Thr  Ala  Arg  Thr  Glu  Leu  Asn  Val
                    245                 250                      255

Gly  Leu  Asp  Phe  Thr  Trp  His  Ser  Pro  Ser  Lys  Ser  His  His  Lys
               260                 265                      270

Lys  Ile  Val  Asn  Arg  Asp  Val  Lys  Pro  Phe  Pro  Gly  Thr  Val  Ala  Lys
          275                 280                      285

Met  Phe  Leu  Ser  Thr  Leu  Thr  Ile  Glu  Ser  Val  Thr  Lys  Ser  Asp  Gln
     290                 295                      300

Gly  Glu  Tyr  Thr  Cys  Val  Ala  Ser  Ser  Gly  Arg  Met  Ile  Lys  Arg  Asn
305                      310                 315                      320

Arg  Thr  Phe  Val  Arg  Val  His  Thr  Lys  Pro  Phe  Ile  Ala  Phe  Gly  Ser
               325                 330                      335

Gly  Met  Lys  Ser  Leu  Val  Glu  Ala  Thr  Val  Gly  Ser  Gln  Val  Arg  Ile
               340                 345                      350

Pro  Val  Lys  Tyr  Leu  Ser  Tyr  Pro  Ala  Pro  Asp  Ile  Lys  Trp  Tyr  Arg
               355                 360                      365

Asn  Gly  Arg  Pro  Ile  Glu  Ser  Asn  Tyr  Thr  Met  Ile  Val  Gly  Asp  Glu
     370                 375                      380

Leu  Thr  Ile  Met  Glu  Val  Thr  Glu  Arg  Asp  Ala  Gly  Asn  Tyr  Thr  Val
385                      390                 395                      400

Ile  Leu  Thr  Asn  Pro  Ile  Ser  Met  Glu  Lys  Gln  Ser  His  Met  Val  Ser
               405                 410                      415

Leu  Val  Val  Asn  Val  Pro  Pro  Gln  Ile  Gly  Glu  Lys  Ala  Leu  Ile  Ser
               420                 425                      430

Pro  Met  Asp  Ser  Tyr  Gln  Tyr  Gly  Thr  Met  Gln  Thr  Leu  Thr  Cys  Thr
          435                 440                      445

Val  Tyr  Ala  Asn  Pro  Pro  Leu  His  His  Ile  Gln  Trp  Tyr  Trp  Gln  Leu
     450                 455                      460

Glu  Glu  Ala  Cys  Ser  Tyr  Arg  Pro  Gly  Gln  Thr  Ser  Pro  Tyr  Ala  Cys
465                      470                 475                      480

Lys  Glu  Trp  Arg  His  Val  Glu  Asp  Phe  Gln  Gly  Gly  Asn  Lys  Ile  Glu
               485                 490                      495

Val  Thr  Lys  Asn  Gln  Tyr  Ala  Leu  Ile  Glu  Gly  Lys  Asn  Lys  Thr  Val
               500                 505                      510

Ser  Thr  Leu  Val  Ile  Gln  Ala  Ala  Asn  Val  Ser  Ala  Leu  Tyr  Lys  Cys
          515                 520                      525

Glu  Ala  Ile  Asn  Lys  Ala  Gly  Arg  Gly  Glu  Arg  Val  Ile  Ser  Phe  His
530                      535                      540
```

| | | | | | | | | | | | | | | | |
|---|---|---|---|---|---|---|---|---|---|---|---|---|---|---|---|
| Val | Ile | Arg | Gly | Pro | Glu | Ile | Thr | Val | Gln | Pro | Ala | Ala | Gln | Pro | Thr |
| 545 | | | | | 550 | | | | | 555 | | | | | 560 |
| Glu | Gln | Glu | Ser | Val | Ser | Leu | Leu | Cys | Thr | Ala | Asp | Arg | Asn | Thr | Phe |
| | | | | | 565 | | | | 570 | | | | | | 575 |
| Glu | Asn | Leu | Thr | Trp | Tyr | Lys | Leu | Gly | Ser | Gln | Ala | Thr | Ser | Val | His |
| | | | 580 | | | | | 585 | | | | | 590 | | |
| Met | Gly | Glu | Ser | Leu | Thr | Pro | Val | Cys | Lys | Asn | Leu | Asp | Ala | Leu | Trp |
| | | | 595 | | | | 600 | | | | | 605 | | | |
| Lys | Leu | Asn | Gly | Thr | Met | Phe | Ser | Asn | Ser | Thr | Asn | Asp | Ile | Leu | Ile |
| | 610 | | | | | 615 | | | | | 620 | | | | |
| Val | Ala | Phe | Gln | Asn | Ala | Ser | Leu | Gln | Asp | Gln | Gly | Asp | Tyr | Val | Cys |
| 625 | | | | | 630 | | | | | 635 | | | | | 640 |
| Ser | Ala | Gln | Asp | Lys | Lys | Thr | Lys | Lys | Arg | His | Cys | Leu | Val | Lys | Gln |
| | | | | 645 | | | | | 650 | | | | | 655 | |
| Leu | Ile | Ile | Leu | Glu | Arg | Met | Ala | Pro | Met | Ile | Thr | Gly | Asn | Leu | Glu |
| | | | 660 | | | | | 665 | | | | | 670 | | |
| Asn | Gln | Thr | Thr | Thr | Ile | Gly | Glu | Thr | Ile | Glu | Val | Thr | Cys | Pro | Ala |
| | | | 675 | | | | | 680 | | | | | 685 | | |
| Ser | Gly | Asn | Pro | Thr | Pro | His | Ile | Thr | Trp | Phe | Lys | Asp | Asn | Glu | Thr |
| | 690 | | | | | 695 | | | | | 700 | | | | |
| Leu | Val | Glu | Asp | Ser | Gly | Ile | Val | Leu | Arg | Asp | Gly | Asn | Arg | Asn | Leu |
| 705 | | | | | 710 | | | | | 715 | | | | | 720 |
| Thr | Ile | Arg | Arg | Val | Arg | Lys | Glu | Asp | Gly | Gly | Leu | Tyr | Thr | Cys | Gln |
| | | | | 725 | | | | | 730 | | | | | 735 | |
| Ala | Cys | Asn | Val | Leu | Gly | Cys | Ala | Arg | Ala | Glu | Thr | Leu | Phe | Ile | Ile |
| | | | 740 | | | | | 745 | | | | | 750 | | |
| Glu | Gly | Ala | Gln | Glu | Lys | Thr | Asn | Leu | Glu | Val | Ile | Ile | Leu | Val | Gly |
| | | | 755 | | | | 760 | | | | | 765 | | | |
| Thr | Ala | Val | Ile | Ala | Met | Phe | Phe | Trp | Leu | Leu | Leu | Val | Ile | Val | Leu |
| | | | 770 | | | | 775 | | | | | 780 | | | |
| Arg | Thr | Val | Lys | Arg | Ala | Asn | Glu | Gly | Glu | Leu | Lys | Thr | Gly | Tyr | Leu |
| 785 | | | | | 790 | | | | | 795 | | | | | 800 |
| Ser | Ile | Val | Met | Asp | Pro | | | | | | | | | | |

( 2 ) INFORMATION FOR SEQ ID NO:6:

( i ) SEQUENCE CHARACTERISTICS:
        ( A ) LENGTH: 180 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

| | | | | | | | | | | | | | | | |
|---|---|---|---|---|---|---|---|---|---|---|---|---|---|---|---|
| Ile | Leu | Ile | His | Ile | Gly | His | His | Leu | Asn | Val | Val | Asn | Leu | Leu | Gly |
| 1 | | | | 5 | | | | | 10 | | | | | 15 | |
| Ala | Cys | Thr | Lys | Pro | Gly | Gly | Pro | Leu | Met | Val | Ile | Val | Glu | Phe | Cys |
| | | | 20 | | | | | 25 | | | | 30 | | | |
| Lys | Phe | Gly | Asn | Leu | Ser | Thr | Tyr | Leu | Arg | Gly | Lys | Arg | Asn | Glu | Phe |
| | | 35 | | | | | 40 | | | | | 45 | | | |
| Val | Pro | Tyr | Lys | Ser | Lys | Gly | Ala | Arg | Phe | Arg | Gln | Gly | Lys | Asp | Tyr |
| | 50 | | | | | 55 | | | | | 60 | | | | |
| Val | Gly | Glu | Leu | Ser | Val | Asp | Leu | Lys | Arg | Arg | Leu | Asp | Ser | Ile | Thr |
| 65 | | | | | 70 | | | | | 75 | | | | | 80 |
| Ser | Ser | Gln | Ser | Ser | Ala | Ser | Ser | Gly | Phe | Val | Glu | Glu | Lys | Ser | Leu |

|   |   |   | 85 |   |   |   |   | 90 |   |   |   | 95 |   |   |
|---|---|---|---|---|---|---|---|---|---|---|---|---|---|---|
| Ser | Asp | Val | Glu<br>100 | Glu | Glu | Glu | Ala | Ser<br>105 | Glu | Glu | Leu | Tyr | Lys<br>110 | Asp | Phe |
| Leu | Thr | Leu<br>115 | Glu | His | Leu | Ile | Cys<br>120 | Tyr | Ser | Phe | Gln | Val<br>125 | Ala | Lys | Gly |
| Met | Glu<br>130 | Phe | Leu | Ala | Ser | Arg<br>135 | Lys | Cys | Ile | His | Arg<br>140 | Asp | Leu | Ala | Ala |
| Arg<br>145 | Asn | Ile | Leu | Leu | Ser<br>150 | Glu | Lys | Asn | Val | Val<br>155 | Lys | Ile | Cys | Asp | Phe<br>160 |
| Gly | Leu | Ala | Arg | Asp<br>165 | Ile | Tyr | Lys | Asp | Pro<br>170 | Asp | Tyr | Val | Arg | Lys<br>175 | Gly |
| Asp | Ala | Arg | Leu<br>180 |   |   |   |   |   |   |   |   |   |   |   |   |

What is claimed is:

1. A pharmaceutical composition comprising
   (a) an expression vector containing a polynucleotide encoding a polypeptide having a functional FLK-1 extracellular and transmembrane domain, and a deleted or mutated cytoplasmic domain so that the encoded polypeptide is signaling-incompetent and renders endogenous wild-type FLK-1 unresponsive to VEGF, wherein said polynucleotide is operatively associated with a regulatory element that controls expression of said polynucleotide in a host cell; and
   (b) a pharmaceutically acceptable carrier.

2. The pharmaceutical composition of claim 1, wherein the expression vector is selected from the group consisting of a retroviral vector, an adeno-associated viral vector and a herpes viral vector.

3. The pharmaceutical composition of claim 2, wherein the expression vector is packaged in a viral particle.

4. The pharmaceutical composition of claim 2 or 3, wherein the polynucleotide encodes a FLK-1 polypeptide which is capable of dimerization but is signalling-incompetent.

5. The pharmaceutical composition of claim 2 or 3, wherein the polynucleotide encodes a FLK-1 polypeptide in which one or more amino acid residues of the cytoplasmic domain is deleted.

6. The pharmaceutical composition of claim 2 or 3, wherein the FLK-1 polypeptide is a human receptor.

7. The pharmaceutical composition of claim 2 or 3, wherein the FLK-1 polypeptide is a murine receptor.

8. The pharmaceutical composition of claim 7 wherein the polynucleotide encodes amino acid residue numbers 1 to 806 of SEQ I.D. NO:5.

9. A method of treating a disease state which is associated with VEGF and/or FLK-1 mediated proliferation of blood vessels in a mammal, comprising administering the pharmaceutical composition of claim 1 to the mammal.

10. A method for treating a subject with a tumor, comprising administering the pharmaceutical composition of claim 8 to the subject.

11. The method of claim 9, where said disease state is selected from the group consisting of rheumatoid arthritis, retinopathy and solid tumors.

12. A method for inhibiting VEGF-induced proliferation of an endothelial cell, comprising administering a compound which inhibits the enzymatic activity of FLK-1, wherein said compound is a polynucleotide encoding a polypeptide comprising a functional FLK-1 extracellular and transmembrane domain, and a deleted or mutated cytoplasmic domain so that the encoded polypeptide is signaling-incompetent.

13. The method of claim 12, wherein said polynucleotide is operatively associated with a regulatory element that controls expression of said polynucleotide in a host cell.

14. A method for inhibiting VEGF-induced proliferation of an endothelial cell, comprising administering the pharmaceutical composition of any of claims 1, 2, or 3.

15. A method for inhibiting signal transduction of FLK-1 in an endothelial cell, comprising administering a compound which inhibits the enzymatic activity of FLK-1, wherein said compound is a polynucleotide encoding a polypeptide comprising a functional FLK-1 extracellular and transmembrane domain, and a deleted or mutated cytoplasmic domain so that the encoded polypeptide is signaling-incompetent.

16. The method of claim 15, wherein said polynucleotide is operatively associated with a regulatory element that controls expression of said polynucleotide in a host cell.

17. The method of claim 15, wherein the polynucleotide encodes amino acid residue numbers 1 to 806 of SEQ I.D. NO:5.

18. A method for inhibiting signal transduction of FLK-1 in a subject, comprising administering to the subject the pharmaceutical composition of any of claims 1, 2, or 3.

19. A method for inhibiting angiogenesis and/or vasculogenesis, comprising administering to an endothelial cell a compound which inhibits the enzymatic activity of FLK-1, wherein said compound is a polynucleotide encoding a polypeptide comprising a functional FLK-1 extracellular and transmembrane domain, and a deleted or mutated cytoplasmic domain so that the encoded polypeptide is signaling-incompetent.

20. The method of claim 19, wherein said polynucleotide is operatively associated with a regulatory element that controls expression of said polynucleotide in a host cell.

21. The method of claim 12, 15, or 19, wherein the FLK-1 polypeptide is a human receptor.

22. The method of claim 12, 15, or 19, wherein the FLK-1 polypeptide is a murine receptor.

23. A method for inhibiting VEGF-induced proliferation of an endothelial cell, comprising administering the pharmaceutical composition of claim 4.

24. A method for inhibiting VEGF-induced proliferation of an endothelial cell, comprising administering the pharmaceutical composition of claim 5.

25. A method for inhibiting VEGF-induced proliferation of an endothelial cell, comprising administering the pharmaceutical composition of claim 6.

26. A method for inhibiting VEGF-induced proliferation of an endothelial cell, comprising administering the pharmaceutical composition of claim 7.

27. A method for inhibiting VEGF-induced proliferation of an endothelial cell, comprising administering the pharmaceutical composition of claim 8.

28. A method for inhibiting signal transduction of FLK-1 in a subject, comprising administering to the subject the pharmaceutical composition of claim 4.

29. A method for inhibiting signal transduction of FLK-1 in a subject, comprising administering to the subject the pharmaceutical composition of claim 5.

30. A method for inhibiting signal transduction of FLK-1 in a subject, comprising administering to the subject the pharmaceutical composition of claim 6.

31. A method for inhibiting signal transduction of FLK-1 in a subject, comprising administering to the subject the pharmaceutical composition of claim 7.

32. A method for inhibiting signal transduction of FLK-1 in a subject, comprising administering to the subject the pharmaceutical composition of claim 8.

* * * * *

UNITED STATES PATENT AND TRADEMARK OFFICE
CERTIFICATE OF CORRECTION

Page 1 of 3

PATENT NO. : 5,851,999
DATED : December 22, 1998
INVENTOR(S) : Ullrich et. al.

It is certified that error appears in the above-identified patent and that said Letters Patent is hereby corrected as shown below:

Column 2, the References Cited should include the following:

U.S. Patent No.5,185,438, Issued:2/9/93, by Lemischka

Risau et al., 1988, "Changes in the Vascular Extracellular Matrix During Embryonic Vasculogenesis and Angiogenesis," Development Biology 125:441-450

Ferrara et al., 1989, "Pituitary Follicular Cells Secrete a Novel Heparin-Binding Growth Factor Specific for Vascular Endothelial Cells," Biochem. Biophys. Res. Comm. 161:851-858

Gospodarowicz et al., 1989, "Isolation and Characterization of a Vascular Endothelial Cell Mitogen Produced by Pituitary-Derived Folliculo Stellate Cells," Proc. Natl. Acad. Sci. USA 86:7311-7315

Leung et al., 1989, "Vascular Endothelial Growth Factor Is a Secreted Angiogenic Mitogen," Science 246:1306-1309

Conn et al., 1990, "Purification of a Glycoprotein Vascular Endothelial Cell Mitogen From a Rat Glioma-derived Cell Line," Proc. Natl. Acad. Sci. USA 87:1323-1327

Ullrich et al., 1990, "Signal transduction by receptors with tyrosine kinase activity," Cell 61:203-212

Ferrara et al., 1991, "The Vascular Endothelial Growth Factor Family of Polypeptides," J. Cell Biochem. 47:211-218

Kashles et al., 1991, "A Dominant Negative Mutation Suppresses the Function of Normal Epidermal Growth Factor Receptors by Heterodimerization," Mol. Cell. Biol. 11:1454-1463

Klagsburn et al., 1991, "Regulators of Angiogenesis," Annu. Rev. Physiol. 53:217-39

Maglione et al., 1991, "Isolation of Human Placental cDNA Coding For a Protein Related to the Vascular Permeability Factor," Proc. Natl. Acad. Sci. USA 88:9267-9271

UNITED STATES PATENT AND TRADEMARK OFFICE
CERTIFICATE OF CORRECTION

PATENT NO. : 5,851,999

DATED : December 22, 1998

INVENTOR(S) : Ullrich et al.

It is certified that error appears in the above-identified patent and that said Letters Patent is hereby corrected as shown below:

Matthews et al., 1991, "A Receptor Tyrosine Kinase cDNA Isolated From a Population of Enriched Primative Hematopoietic Cells and Exhibiting Close Genetic Linkage to c-kit," Proc. Natl. Acad. Sci. USA 88:9026-9030

Mitchell et al., 1991, "Recombinant Expression and Characterization of the 121 Amino Acid Form of Vascular Endothelial Growth Factor (VEGF)," J. Cell. Biochem., Keystone Symposia on Molecular and Cellular Biology, Supplement 15C, Excerpt G207

Terman et al., 1991, "Identification of a New Endothelial Cell Growth Factor Receptor Tyrosine Kinase," Oncogene 6:1677-1683

Breier et al., 1992, "Expression of Vascular Endothelial Growth Factor During Embryonic Angiogenesis and Endothelial Cell Differentiation," Development 114:521-532

De Vries et al., 1992, "The fms-Like Tyrosine Kinase, a Receptor for Vascular Endothelial Growth Factor," Science 255:989-991

Sarzani et al., 1992, "A Novel Endothelial Tyrosine Kinase cDNA Homologous To Platelet-Derived Growth Factor Receptor cDNA," Biochem. Biophys. Res. Comm. 186:706-714

UNITED STATES PATENT AND TRADEMARK OFFICE
CERTIFICATE OF CORRECTION

PATENT NO. : 5,851,999
DATED : December 22, 1998
INVENTOR(S) : Ullrich et al.

It is certified that error appears in the above-identified patent and that said Letters Patent is hereby corrected as shown below:

Spivak-Kroizman *et al.*, 1992, "Heterodimerization of c-erbB2 With Different Epidermal Growth Factor Receptor Mutants Elicit Stimulatory or Inhibitory Responses," J. Biol. Chem. 267:8056-8063

Terman *et al.*, 1992, "Identification of the KDR Tyrosine Kinase as a Receptor for Vascular Endothelial Cell Growth Factor," Biochem. Biophys. Res. Comm. 187:1579-1586

Plate *et al.*, 1993, "Up-Regulation of Vascular Endothelial Growth Factor and Its Cognate Receptors in a Rat Glioma Model of Tumor Angiogenesis," Cancer Research 53:5822-5827

Livenh *et al.*, 1986, "Reconstitution of Human Epidermal Growth Factor Receptors and Its Deletion Mutants in Cultured Hamster Cells," J. Biol. Chem. 261:12490-12497

Prywes *et al.*, 1986, "Mutations in the Cytoplasmic domain of EGF receptor affect EGF binding and Receptor Internalization," EMBO Journal 5:2179-2190

Nicolas *et al.*, 1987, "Retroviral Vectors," Vectors, Chapter 25, pp. 493-44

Signed and Sealed this

Twentieth Day of July, 1999

*Attest:*

Q. TODD DICKINSON

*Attesting Officer*  Acting Commissioner of Patents and Trademarks